US007711671B2

(12) United States Patent
Meyers

(10) Patent No.: US 7,711,671 B2
(45) Date of Patent: May 4, 2010

(54) PROBLEM SOLVING PROCESS BASED COMPUTING

(76) Inventor: Kim C. Meyers, 1713 Central St., Evanston, IL (US) 60201

( * ) Notice: Subject to any disclaimer, the term of this patent is extended or adjusted under 35 U.S.C. 154(b) by 285 days.

(21) Appl. No.: 11/436,010

(22) Filed: May 17, 2006

(65) Prior Publication Data

US 2007/0011128 A1    Jan. 11, 2007

Related U.S. Application Data

(60) Provisional application No. 60/681,937, filed on May 17, 2005.

(51) Int. Cl.
*G06N 5/02*    (2006.01)
(52) U.S. Cl. .................................... 706/47
(58) Field of Classification Search ............... None
See application file for complete search history.

(56) References Cited

U.S. PATENT DOCUMENTS

| | | | |
|---|---|---|---|
| 6,904,432 B2 | 6/2005 | Charlot et al. | |
| 2004/0122704 A1* | 6/2004 | Sabol et al. | 705/2 |
| 2004/0249251 A1* | 12/2004 | Olschafskie | 600/300 |
| 2005/0027569 A1* | 2/2005 | Gollogly et al. | 705/3 |
| 2005/0108052 A1* | 5/2005 | Omaboe | 705/2 |
| 2005/0216503 A1 | 9/2005 | Charlot et al. | |

OTHER PUBLICATIONS

Weed, L.L., Medical Records That Guide and Teach, *New England Journal of Medicine*, Mar. 14, 1968, pp. 593-600, vol. 278, No. 11.

Meyers et al., The Importance of Cleaning Up Soap, *Academic Medicine*, Nov. 1997, pp. 933-934, vol. 72.
Rubin, Alan S., Another Way to Enhance Soap's Usefulness, *Academic Medicine*, May 1998, p. 445, vol. 73.
Meyers et al., Another Way to Enhance Soap's Usefulness—In Reply, *Academic Medicine*, May 1998, pp. 445-446, vol. 73.

(Continued)

*Primary Examiner*—David R Vincent
*Assistant Examiner*—Peter Coughlan
(74) *Attorney, Agent, or Firm*—Beem Patent Law Firm

(57) ABSTRACT

A computer implemented problem solving system utilizing an information storage infrastructure and a flexible development environment for data storage, includes a stored, user modifiable program including a problem solving rule set relevant to a problem to be solved, a stored, user modifiable set of vocabularies related to a problem to be solved, at least one stored, user modifiable knowledge set relevant to a problem to be solved, and stored, user modifiable individual user preferences relevant to a problem to be solved. A computer implemented problem solving method utilizing an information storage infrastructure and a flexible development environment for data storage, includes generating screen displays on a display screen, and entering a problem identified by an initial assessment to the computer at a designated place in one of the screen displays. The method further includes selecting from at least one of the screen displays at least one item from at least one of: a stored, user modifiable set of vocabularies related to a problem to be solved, at least one stored, user modifiable knowledge set relevant to a problem to be solved, and stored, user modifiable individual user preferences relevant to a problem to be solved and entering the at least one item to the computer at a designated place in one of the screen displays.

26 Claims, 70 Drawing Sheets

OTHER PUBLICATIONS

Meyers et al., The Follow-Up Note: Format and Requirements, Specifications for the Computerized Medical Record, AMIA Proceedings: Orlando, FL, 1997, pp. 1-5.

Dick, R.S. And Steen, E.B., The Computer-Based Patient Record, *Institute of Medicine*, 1997, Chapter 4: pp. 138-175, National Academy Press, Washington, D.C.

Kohn et al., To Err Is Human: Building a Safer Health System, *Institute of Medicine*, 2000, Chapter 2: pp. 26-48, Chapter 5: pp. 86-108, National Academy Press, Washington, D.C.

Wears et al., Computer Technology and Clinical Work: Still Waiting for Godot, *Journal of the American Medical Association (JAMA)*, Mar. 9, 2005, pp. 1261-1263, vol. 293, No. 10.

Han et al., Unexpected Increased Mortality After Implementation of a Commercially Sold Computerized Physician Order Entry System, *Pediatrics*, Dec. 2005, pp. 1506-1512, vol. 116, No. 6.

Poissant et al., The Impact of Electronic Health Records on Time Efficiency of Physicians and Nurses: A Systematic Review, *Journal of the American Medical Informatics Association*, Sep/Oct 2005, pp. 505-516, vol. 12, No. 5.

Shaw et al., Elements of a Theory of Human Problem Solving, *Psychological Review*, 1958, pp. 151-166, vol. 65, No. 3.

Simon et al., Decision Making and Problem Solving, Report of the Research Briefing Panel on Decision Making and Problem Solving, Research Briefings by the National Academy of Sciences, 1986, pp. 1-19, National Academy Press, Washington, D.C.

Problem Solving, *Wikipedia: The Free Online Encyclopedia*, Jun. 29, 2006, pp. 1-6, available at http://en.wikipedia.org/wiki/Problem_solving (last visited Jul. 5, 2006).

Naeymi-Rad et al., Expert Knowledge Base Designed Using EMR-Modeling Technique, 1986, pp. 1-6.

Zeng et al., A Knowledge-Based, Concept-Oriented View Generation System for Clinical Data, *Journal of Biomedical Informatics*, 2001, pp. 112-28, vol. 34.

Weed, L.L., Medical Records That Guide and Teach (Concluded), New England Journal of Medicine, Mar. 14, 1968, pp. 652-657, vol. 278, No. 11.

Meyers, et al., Problem Focused Knowledge Navigation. Implementing the Problem Focused Medical Record and the O-Heap Note, *Proceedings: AMIA Annual Symposium*, 1998, pp. 1-5, Hanley & Belfus, Inc., Philadelphia, PA.

\* cited by examiner

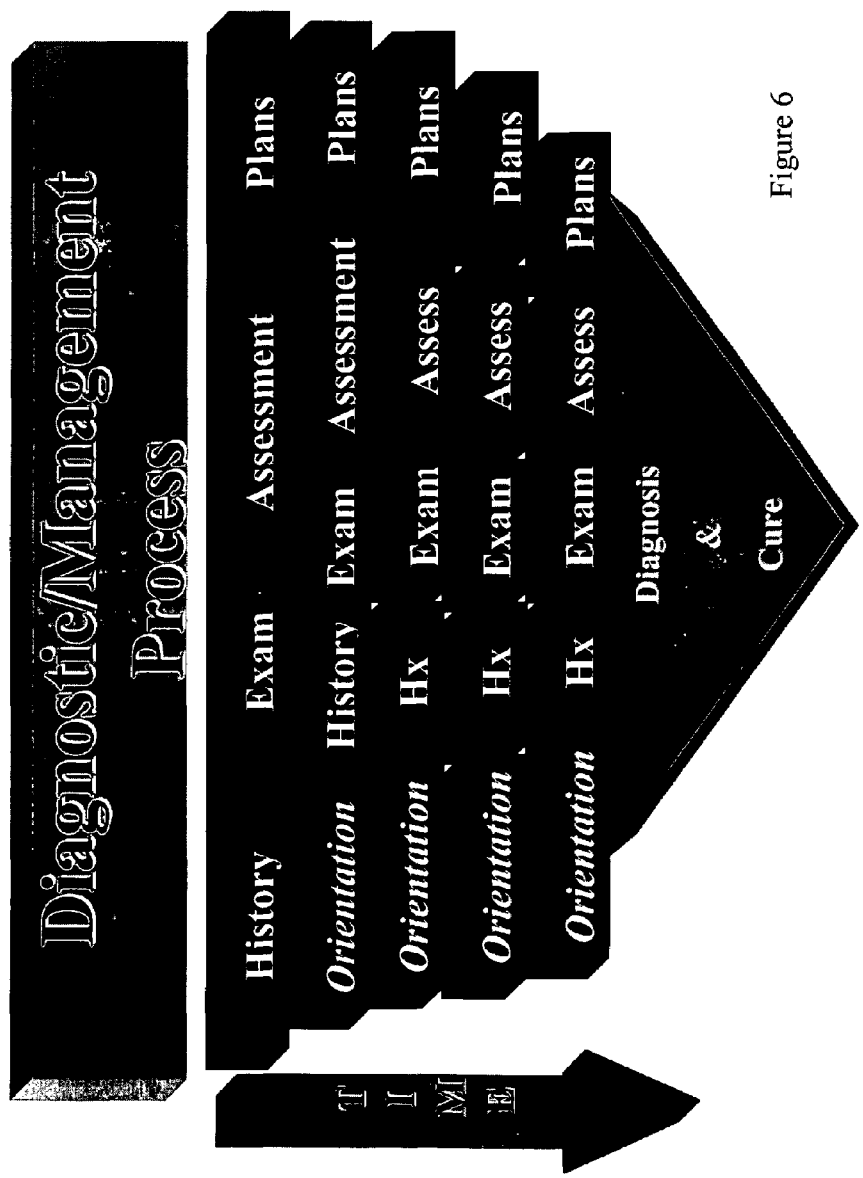
Figure 5b
Figure 6

The FACE SHEET is an amalgamation of General Facts about the Patient. This is an extremely useful View of a Patient's Problem in Context with other Problems and Personal Histories the patient has. Starting at 1 at the top of page, it shows the Patients name and other identifiers. 1.

Number 2 is the Problem List. This consists of all Active Problems the patient has. This is an essential component of all decisions made about 2. the patient. For example, a back pain in an 80 year old woman with a history of 2 Breast Cancers, has more potential for a serious underlying cause, then a back pain in a 24 year old woman with no Problems on her Problem List Vital Signs represent current Pulse, Blood Pressure etc.... 3.

Current Medications and Allergies are the 4th Component. The information 4. contained here needs to be considered against every treatment decision The History Tables are discussed on the next page 5.

Figure 62

PROBLEM SOLVING PROCESS BASED COMPUTING

This application claims the benefit of U.S. Provisional Application No. 60/681,937 filed on May 17, 2005.

BACKGROUND OF THE INVENTION

1. Field of the Invention

The present invention relates generally to a novel and improved problem solving process (PSP), and particularly, a problem solving process in relation to the medical field/domain

2. Description of the Related Art

Before disclosing the details of the problem solving process in relation to the medical field/domain, the applicant will synopsize the current state of computerized design in this area following 36 years of continued efforts. Medicine is a highly complex field/domain that takes years of training to become proficient in. It has the challenges of following data over decades, resolving acute and chronic conditions, documentation requirements with medical legal implications, and true life and death situations. It is also a field where adoption of computerized medical record systems has had extremely limited success despite decades of investment, research, and strong external pressures to computerize. Applicant contents that the entire field of medicine can be reduced to a PSP or Problem Solving Process Computing (PSP Computing). PSP Computing distills the entire field of medicine to the "Problem Solving Process," with all its necessary outputs or charting (documentation, prescriptions, orders, instructions, alerts, scheduling tasks, etc.) automatically produced as a by product of solving the problems.

Applicant contends that the same Problem Solving Process can do the same in any field/domain that solves problems over time. This application will primarily show this concept related to medicine, but will show screenshots of other fields/domains that could be converted using the same principles. Specifically, Applicant further claims that the exact same Process can be applied to any field/domain (i.e. law, consultancy, computer programming, detective work, etc.) that solve problems over time.

Before proceeding, the Applicant will discuss the difference between work of practicing ones profession (problem solving) and the work of documenting what occurred. Let us take as an example, a medical doctor (M.D.), physical therapist, or chiropractor performing a therapeutic maneuver or dispensing a prescription to relieve a patient's back pain. Solving the problem is the "real-" work or goal of the encounter. The client wants the professional/doctor to solve the problem. Solving the problem is what the professional has been trained to do. To most professionals, problem solving work can be exhilarating, as they are using their skills to accomplish a goal that makes them matter. If solving the problem provides a complete cure of the problem, never to recur, the quality of the documentation in that simple example would potentially be immaterial. Yet, in the medical field/domain, and majority of others, it is the documentation, or the "work-" work that becomes the major requirement of the visit for payment and medical legal reasons.

Since this documentation/paperwork has both financial and legal ramifications, software solutions have focused on duplicating the documentation requirements of medicine and other fields/domains, as they convert from the "paper world." Designed around the outputs of the fields/domains they computerize, they are fundamentally flawed. This form/output based design leads to greater documentation requirements, like proper formatting requirements. These requirements lead to steep learning curves and often more time documenting the encounter than time spent solving the problem. Computerized documentation requirements are often more cumbersome and time consuming than its "paper world" counterpart. This form/output based design increases the workload of the professional, and even with the many generic advantages of computers (like data analysis or location independence), will never lead to the efficiencies of a Problem Solving Process design.

Before disclosing the details of the Problem Solving Process in relation to the medical field/domain, Applicant will synopsize the current state of computerized design in this area following 36 years of continued efforts. For example, in the medical domain, designing around the charting process in Electronic Health Records (EHRs) or Electronic Medical Records (EMRs) has been the standard design since 1969. This approach has not had significant market penetration (currently reported at 5 to 13 percent of M.D.'s use EMRs despite billions of dollars in investments and extraordinary public, administrative, and payor pressure to computerize).

The "Paper World"

The original thrust to computerize the medical record came from Larry Weed's seminal work in 1969. See L. L. Weed, *Medical Records That Guide and Teach*, N. Eng. J. Med., 593-600 278:11 (1968). He correctly concluded that the medical record had no standard format. It was entirely at the whim of the individual practitioner regarding how much detail of the patient's complaints was put in the note. Prior to Weed, many practitioners had the complete history and physical records of their entire patient population on 5"×6" index cards. These index card medical records had an extremely filtered set of details about the patients' medical history. For prescriptions, the notes would often just have the date and the drug, such as "4/01/1960—Penicillin I.M.," with no indication of why the medication was given and what was the outcome of the intervention. Even in hospitalized patient records, the details of many problems were often meshed together in a single paragraph in a sloppy manner. If a problem such as chest pain led to an electrocardiogram (EKG) and a cardiology consultation, these "plans" were often not even linked to their source. Instead, they were simply listed at the end of the note, or they were not listed in the note at all and just ordered on an order sheet in a separate part of the chart. The outcome of these plans was generally not individually noted in the follow up. This entire record keeping process was very informal. It was not formalized as it was not a necessity or an advantage in the "paper world" to chart it.

Computerization of the Medical Note

Dr. Weed proposed a new format for the medical note around two fundamental concepts. These were the Problem Oriented Medical Record (P.O.M.R.) and the Subjective, Objective, Assessment, and Plan (S.O.A.P.) chart note. The P.O.M.R. elevated each of the patient's problems to the highest level in the chart and then organized the S.O.A.P. format as the means of reporting how the problem was doing in the follow-up visits. He also championed the use of flow sheets to follow the data that accumulated around the problems for simpler analysis.

The result of Weed's efforts led to "Problem Lists" as an organizational tool and the S.O.A.P. note as the formatted note structure underneath each problem. However, the patient could still be cared for without formally using any component of the Weed method. The M.D. might not be as organized or the documentation might seem less complete, but the patient could be cured nonetheless. The amount and form of documentation was still entirely up to the individual, despite Weed's New England Journal of Medicine article and the adoption of the P.O.M.R./S.O.A.P. method at some medical schools. Many M.D.s continued to write notes in their own format, and others used the P.O.M.R./S.O.A.P. style intermittently, and many were exclusively P.O.M.R./S.O.A.P. Even at the peak of its popularity, the P.O.M.R./S.O.A.P. format never reached even a 50 percent level of adoption in the medical record. See Letter of K. C. Meyers & H. J. Miller to Academy of Medicine, The *Importance of Cleaning up S.O.A.P.*, 72:9 933-4 (1997). See also Letter of A. S. Rubin to Academy of Medicine, *Another Way to Enhance S.O.A.P.'s Usefulness*, 73:445 (1998).

Despite this, when EMRs began to be developed post 1969, this was the only documentation standard in the medical field/domain that was available. A "standard" with less than a 50 percent adoption rate is fated to have issues, and such it has been for the Weed design. As time went on, the adoption of P.O.M.R./S.O.A.P. EMRs was underdeveloped. Adjustments were made with some EMRs still having a Problem List, but abandoned the requirement of using it for charting. Follow-up notes became an unstructured blank sheet of paper. Other EMRs completely abandoned a problem focus, but enhanced the blank sheet of paper with shortcut key strokes or templates. These EMRs are often described as "Encounter Based" mimicking the paper world format of not requiring an association between the plans of treatment with the problems they were ordered for. In spite of it's free form, the Encounter Based approach was more cumbersome than the paper record, as most physicians were not good typists and it interfered with the face to face contact that could be made with the Patient chart.

A comprehensive review of the designs of EMRs in the last 36 years can be classified into 3 views: (1) source-oriented (organizing the record into sections based on source of data, such as, x-ray, labs, notes), (2) time-oriented (organizing data chronologically), and (3) concept-oriented (the most famous example being the Weed P.O.M.R. or S.O.A.P. construct). An additional view is called the "Knowledge-based, Cconcept-oriented" view. This view was an attempt to decrease the information overload of current EMRs. It attempted to filter results based on predefined views, such as "show all pulmonary tests for CHF." The present invention is a new approach to EMRs/EHRs called "Problem Solving Process Computing." It is not a view, or a format, it is a process with major advantages over all of these concepts.

The Trouble with S.O.A.P.

The Weed design had a serious design defect, that was especially evident as one tried to computerize the paper record. This fundamental flaw was focusing first on "S" or "subjective" and looking at the "O" or "objective" second. Thus, the process is designed around the concept that the first thing you chart on a follow up visit is the "S"—how the patient feels about the state of the problem and any new related verbal information regarding the condition. Then, "S" is followed by the "O" which represents objective or measurable elements. This was defined by Weed as "Test Results and Physical Findings." The "A" is for the doctor's "assessment," and the "P" is for the "plans."

Working off of this standard was a major obstacle to designing an effective EMR. That is because it the S.O.A.P. method puts the "S" in front of the "O." This did not match the actual behavior of the physicians, making it an artificial construct. There was a disconnect between what was documented and the actual order of what was done. Worse, the subjective section is substantially changed by the "P" plan results. That is, the specific questions that are asked in the verbal exchange (subjective) part of the visit, is substantially altered by the plan results. This combination of asynchrony and the effect the plan results have on the subsequent questions, are the fatal flaw of the S.O.A.P. note when it comes to computerization.

In contrast to the S.O.A.P. methodology, practitioners first looked at the "objective" section that represented plan results, prior to asking any (subjective) questions. This objective analysis was routinely done by the practitioner before walking into a patients' room in a hospital or office. See K. C. Meyers et al., *The Follow up note: Format and Requirements, Specifications for the Computerized Medical Record*, AMIA Proceedings: Orlando, Fla. (1997). Even doctor-to-patient phone calls would be preceded by a brief chart review before telephoning the patient. This is because plan results always effect what questions that are asked in the "S" of the S.O.A.P. note. For example, if a patient complained of a headache and an MRI of the brain did not show a brain tumor, then the clinician would accept that the patient did not have a brain tumor based on the MRI. The clinician would not ask questions related to the possibility of brain tumor in the "S" section. Another example is a patient with a problem of abdominal pain. If the patient had a Computer Tomography Scan (CT scan, or CAT Scan) that showed Diverticulitis, the M.D. would emphasize questions in the "S" section related to peanuts, seeds, popcorn and other related items that could cause a flare of this illness.

The Institute of Medicine

The Institute of Medicine's (IOM) 1991 seminal work entitled *The Computer-Based Patient Record: An Essential Technology for Health Care* declared the need to computerize the medical record for healthcare. See R. S. Dick, E. B. Steen, *The Computer-Based Patient Record: An Essential Technology for Health Care*, Institute of Medicine Committee on Improving the Patient Record (1991). The goal was to computerize the medical record within 10 years. The IOM spun off the Computerized Patient Record Institute (CPRI) and the Nicholas Davies Award to pursue this goal. The CPRI promoted standards and adoption of EMRs, including a standard that listed 154 requirements of a satisfactory EMR. Eventually, the CPRI produced a document stating that if the specific 154 requirements of an EMR were accomplished, it would be successful. In 1999, after over 100 million dollars invested by HBOC, the Smart Medical Record was pulled from the market, having completed 140 of the CPRI 154 requirements, partially done with 10 others, and only had 4 requirements not addressed. This certainly brings up the issue of perceived requirements versus the "real" requirements. It is the Applicant's contention that all written requirements for EMRs, such as those proposed by the Institute of Medicine focus on the chart structure, and not the real work of the medical encounter.

Managed Care

During the 1990s, EMRs were heavily promoted by managed care companies which were transforming healthcare in their own right. This led to massive investment of venture capital into EMRs due to manage care's desire to measure the care delivered. This also led to additional "reasons" why the EMR was essential. Data measurement was needed if one was to apply more strict business principles to medicine. Goals included the elimination of the cost of paper records, legibility, HEDIS (Health Plan Employer Data and Information Set) scores (essentially healthcare report cards on the providers). Even these compelling business mandates did not prove compelling enough to overcome the basic usability problems of the chart-based EMR. Some of these same arguments are being proclaimed today by the Government and the Institute of Medicine as the reason EMRs should be adopted now.

The Internet

With the Internet emerging, some of these companies leveraged their stock valuations to temporarily reap billions of dollars of paper wealth on the prediction that the portability of the Internet was the essential technological development that would make EMRs successful. The Internet did not lead to adoption and these companies had a reversal of fortune. Application Service Providers (ASPs) were also promoted as the solution. The theory was that the cost of the application would be less if managed centrally over a DSL or T1 line, and that would convince M.D.s to change; it was not the solution. The market for EMRs temporarily crashed with the extraordinary amount of money lost in these ventures and the bursting of the internet bubble.

Electronic Health Record (EHR)

In 2000, the IOM released its next EMR report. See Linda T. Kohn et al., *To Err is Human—Building a Safer Health System*, Committee on Quality of Health Care in America, Institute of Medicine (2000). Specifically, this report claimed that nearly 100,000 deaths per year could be prevented by computerized information systems. They contended that these errors could be reduced by using information technology. The report was followed by an attempt to improve the marketability of the EMR by changing the name to EHR, or Electronic Health Record. Just as EMR had replaced the Computerized Patient Record (CPR) in the mid 1990s, it was hoped a change in name and slight change in focus would improve the marketability of these products.

The Government

The government became more directly involved due to 9/11 and the need for an EHR to be in place in the event of a terrorist attack utilizing biological agents. In addition to these national security issues, in the face of rising Medicare costs, the Government has become increasingly energized to seek healthcare savings from the touted efficiencies that EMRs could bring.

Employers

Managed care was the beginning of trying to lessen healthcare premiums to employers by measuring the quality and necessity of tests and procedures. The increasing pressure of globalization on businesses has put them squarely behind any initiatives that would increase the measurability of the services they are buying.

All of the above were compelling reasons as to why EMRs would be valuable to society. They addressed the societal advantage of computerization without thoughtfully addressing the usability issues facing the physician. Like the first car builders who thought the car should be steered with horse reins, the EMR was designed around the chart.

As noted before, the focus of all EMR designs has been on the chart and charting. There was no standard across physicians, even within the same specialties. The most common design for note writing was S.O.A.P. which was at best used by 50 percent of M.D.s, and therefore programs formatted on the S.O.A.P. Weed method required greater than 50 percent of M.D.s to change their habits. Many EMRs adopted problem-specific templates which were useful for first time visits but failed in follow-up notes. This failure was critical since the vast majority of visits are follow-up visits. Others adopted a blank text field and used short hand techniques to auto-generate text. As with the template-driven notes, the S.O.A.P. and free text with "short hand" failed miserably in the follow-up visits.

In addition, the structure of these conventions led to boiler plate, often bulky notes that either regularly repeated past text to the point that they were often inaccurate. To save time, some physicians just typed in terse free text notes that often do not provide sufficient detail to truly describe what the M.D. had just done. While the computer provides greater legibility, the narrative is often lost in the sameness or incompleteness of the note, i.e. a long note that says almost nothing new (for the third time in a row) or a short note that is bereft of detail.

Aside from poor market adoption, there has been provocative literature that questions designing EMRs around the chart structure. For instance, Edwin Tufte, an authority on the representation of data sets in logical patterns, has strongly spoken out against the design of the chart as a basis for an EMR. His quote, "the chart is a data dump, it was not designed with the care of the patient in mind" identifies the problem of designing an EMR around the chart. His solution of a graphical representation with differential weighting of data based on the time elements is not the correct solution, but it does identify the problem with standard chart based design head on.

In addition, The Journal of the American Medical Association (JAMA) published an editorial in March 2005 highly critical of the current chart based designs. See R. L. Wears & Marc Berg, *Computer Technology and Clinical Work Still Waiting for Godot*, J. Amer. Med. Ass'n, 293:1261-3 (2005). This article recognizes the problem that current designs create on physician workflow, and questioned claims that computerization of the note was having a net positive effect on patient errors. It appeared that the problems it solved were replaced with problems it created. Users were clearly hindered by the requirements of the system and its focus on the format/structure the program funneled them into, rather than funneling knowledge and workflow enhancements to the user.

This design can have serious, negative effects at the hospital bedside. This was illustrated in two publications in 2005. An article in Pediatrics from December 2005 questioned the safety improvements that computers are supposed to provide. In this article, an EMR was shown to actually increase the death rate in a pediatric intensive care unit (ICU). See Han et al., *Unexpected Increased Mortality after Implementation of a Commercially Sold Computer Order Entry System*, Pediatrics; 1506-12, Vol. 116 No. 6 (December 2005). As noted in the article, computerization has increased the time it takes to document the visit. This documentation time decreases doctor-patient time. In an ICU setting, where each minute counts, this can be the difference between life and death.

A second article addresses this time problem directly. A review from September 2005 analyzed the time physicians spent documenting notes and writing orders in all published reports on EMRs for the last 20 years. See L. Poissant, et al., *The Impact of Electronic Health Information Systems on Time Efficiency of Physicians and Nurses: A Systematic Review*, J. Am. Med Informatics Assoc., 505-16 Vol. 12 No. 5 (September/October 2005). This extensive review documented a range of increased work for physicians, from 98 to 328 percent per working shift. The average increase in time spent documenting the encounter and ordering necessary tests was 238 percent. This increase in documentation time logically effects doctor-patient time and helps explain the findings in the Pediatric article. It speaks volumes as to why there has been poor adoption of EMRs/EHRs.

Despite decades of efforts, billions of dollars of investments, government mandates, etc., the benefits that EMRs could provide patients and physicians have been minimized due to a serious design flaw. The flaw is that they are documentation- or chart-based.

In discovering and resolving this design flaw, the Applicant will advance the entire medical field/domain. Properly implementing Problem Solving Process Computing will have similar ramifications to all knowledge fields/domains.

SUMMARY OF THE INVENTION

In accordance with one aspect of the invention, a computer implemented problem solving system utilizing an information storage infrastructure and a flexible development environment for data storage, comprises a stored, user modifiable program including a problem solving rule set relevant to a problem to be solved, a stored, user modifiable set of vocabularies related to a problem to be solved, at least one stored, user modifiable knowledge set relevant to a problem to be solved, and stored, user modifiable individual user preferences relevant to a problem to be solved.

In accordance with another aspect of the invention, a computer implemented problem solving method utilizing an information storage infrastructure and a flexible development environment for data storage, comprises generating screen displays on a display screen; entering a problem identified by an initial assessment to said computer at a designated place in one of said screen displays; selecting from at least one of said screen displays at least one item from at least one of: a stored, user modifiable set of vocabularies related to a problem to be solved, at least one stored, user modifiable knowledge set relevant to a problem to be solved, and stored, user modifiable individual user preferences relevant to a problem to be solved and entering said at least one item to said computer at a designated place in one of said screen displays.

BRIEF DESCRIPTION OF THE SEVERAL VIEWS OF THE DRAWINGS

FIG. 5b is a diagram showing arrangement of problem bar tabs provides additional visual orientation.

FIG. 6 is a diagram showing how the process is repeated over time to solve problems.

FIG. 8 is a diagram showing an overview screen shot of the iEMR face sheet.

FIGS. 9-71 show screen shots of various iEMR functions and displays of data.

DETAILED DESCRIPTION

Introduction

Figure 1:
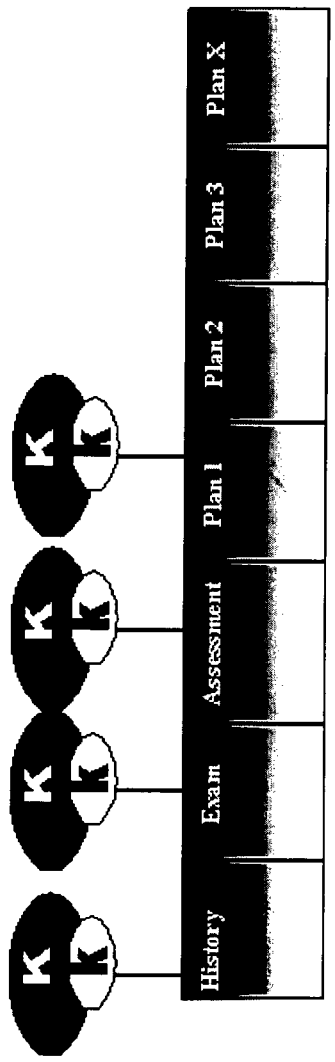
FIG. 1 is a diagram showing components of an initial medical encounter, with history, exam, assessment and plan(s).

The problem solving process across many fields/knowledge domains follows a definable set of rules that occur in all cases, without exception. Trained professionals, in many knowledge domains, routinely follow these rule sets; without formally recognizing the process. Problem solving process computing is a fundamental departure from current designs. Applied to the core level of program design, it will lead to efficiencies and interface enhancements not possible with current form/output designs. This will be especially evident and efficient in professional fields/domains that have specialized knowledge sets and solve problems over time.

In the "paper world," which preceded the computerized world of today, there was no obvious efficiencies from following a "problem solving rule set". Therefore, it was never formalized or taught. As computer programs have attempted to transform the "paper based world", the focus has been on computerizing the output of the problem solving process, i.e. the medical note, the legal file etc. On the surface, this seemed logical to the designers and consultants charged with the task, who surmised it would seem natural; even welcomed by the user.

This design effort has led to new types of inefficiencies and clumsy user interfaces, that provide generic more than specific computer workflow enhancements. This approach has led experts in the field, such as nobel laureate Herbert Simon to declare that real world problem solving—that is the common problems of every day life and professional work—is not the same across knowledge domains and fields. Newell A, Shaw J C, Simon H A. *Elements Of Theory Of Human Problem Solving. Psych Rev* 1956; 65:151-66; Simon H A et. al. *Decision Making and Problem Solving. Report of the Research Briefing Panel on Decision Making and Problem Solving. Research Briefings by the National Academy of Sciences*. National Academy Press 1986 It has also led to a definition of problem solving in the internet encyclopedia—Wikipedia—that agrees with that premise and even supports a view that problem solving in North America is different than in Europe. http://en.wikipedia.org/wiki/Problem_solving. The patent applicant contends that that all people solve problems the same way, regardless of field/domain or country of origin. Recognizing this, along with exactly how it is done, will have a fundamental effect on human—computer interfaces. computer interfaces will appear to "think like we think".

The patent applicant first noted this issue as a pilot test site for a computerized medical record. In using this chart/chart note designed electronic medical record (EMR), the patent applicant discovered that this design was inherently flawed. Faced with the inefficiencies that the chart based EMR design brought to the medical field, the applicant embarked on a deep analysis of the problem solving process that was being done, but not formally recognized, in the "pen and paper world". This discovery led to the patent applicant discovering the unique set of rules that drive the process of solving problems over time in all fields/domains.

Once discovered, it was postulated by the patent applicant that programming these rules would gain efficiencies not possible with other traditional computer programs and substantially advance the field of computerization and all fields that use computer programs. This was accomplished by "reducing" the field/domains to their basic work units: problem solving, vocabularies, knowledge sets and individual user preferences. In so doing, the software becomes scalable and naturally intuitive. To most practitioners, it will appear to be "the way they think," as they practice within their field/domain.

It is the patent applicant's contention that software programs designed around the problem solving process will provide a transformational technology that will enhance the productivity of all computer users, and most dramatically, knowledge workers who solve problems over time. To prove this postulate, the patent applicant embarked on applying it to the field/domain of medicine.

Medicine is a highly complex field/domain that takes years of training to become proficient in. It has the challenge of following data over decades; resolving acute and chronic conditions; documentation requirements with medical legal implications; and true life and death situations. It is also a field where adoption of computerized medical record systems has had extremely limited success despite decades of investment, research and strong external pressures to computerize. It will be shown that the entire field of medicine can be "reduced" to a "problem solving process" or problem solving process computing (PSP computing). PSP computing distills the entire field of medicine to the "problem solving process," with all its necessary outputs or charting (documentation/prescriptions/orders/instructions/alerts/scheduling/tasks) automatically produced as a by product of solving the problem(s).

In demonstrating this process working in such a difficult, diverse problem driven field/domain as medicine; the patent applicant contends that this same problem solving process can do the same in any field/domain that solves problems over time. The application will primarily show this concept related to medicine, but will show screenshots of other fields/domains that could be converted using the same principles. Specifically, we make further claims that the exact same process can be applied to any field/domain, i.e. law, real estate, consultancy, computer programming, detective work and many more) that solve problems over time.

The Problem Solving Process

The next section defines the rules of problem solving process programming. following these problem solving rules fundamentally changes the human-computer interaction focusing on the true work of the field/domain while automatically delivering any needed documentation.

PSP-based computing enables the user to be constantly in the "decision making mode" rather than the "data gathering, literature review, decision making, followed at the end by documentation mode" of standard paper and system designs currently available. The user has standard domain knowledge sets pre-populated around the problem sets the individual user sees in their practice. In addition, the invention inherently "learns" continually from the user what "domain subset of the universal knowledge around each problem" the user selects to solve the problems based on their own individual experiences and preferences. Aside from this, all they need to add is their "local knowledge," i.e. addresses and names of sub-specialists and other "plan providers" and "local knowledge around the client/patient" like pharmacy, insurance, formularies that affect the problem solving plan choices.

Why are computers difficult to use for most people? Current computer designs "think" like computers, not like humans. In the course of optimizing the PSP computing, it became obvious that computers were not just designed around the output of our work; they were designed around how computers organize and use information.

People think in neural nets of interconnected nodes that quickly tell us where we left off with people or things in our environment. In addition, human neural nets use this knowledge with goals in mind. These goals are either quickly reached or based on feedback, the person assesses that there is a problem, and redirects their thoughts with new plans to get the desired result. There are numerous examples of this in our day to day activities, in fact, it is happening constantly. There are very few processes in the human mind that do not go through the following:

A. A prompt of some sort sets off a neural net; this may prompt further nodes.

B. The nodes are evaluated, and trigger a goal directed action such as:
  1. More information needed, will look for more now or later, from either with more thinking or external sources, possibly queue for now.
  2. Action needs to be taken, physically, verbally, or mentally.
  3. No more information needed, goal is reached.
  4. Goal of current node less important than next node that has come up automatically or via interruption, and node is dismissed.

Even "automatic" functions go through a rapid fire assessment of the situation as a Plan is initiated. For example, if you were urinating, and someone knocked on the door, you would likely have a short decrease in urine output as you assessed this "unexpected interruption" of your plan to empty your bladder. You would quickly scan and assess that the door was locked; you would likely verbalize your presence, and in a matter of seconds, resume the "task" at hand. Or, when you are looking for a paper on your desk, you use prompts from your neural net that gives you an approximate idea of where you left the paper. As you page through the papers on your desk, your brain is rapidly, almost subliminally, going through a goal directed identification process saying "not it" to each paper you see. It does this until it reaches the paper you had set out to find.

Even in conversation, the goal is to make a point, tell a joke or express an emotion. An internal mental assessment of how well you are communicating your points to your colleagues or friends is going through a rapid feedback and adjustment process automatically. This leads to nearly automatic changes in your emphasis/facts brought forward/inflections/body language/and emotions as you try to reach your goal in the verbal interchange.

In contrast, computers "think" in terms of root-tree-branch-leaf-vein-node knowledge locations. The node is the last place they get to! Compounding this, they go to nodes one at a time with no "a priori" knowledge of how they are interconnected. They look at data as data; Goals are not inherent to computer programs. Their virtue is their exact recollection of the finest detail. Unfortunately, for humans to get at this detail, they are always forced to navigate some level of the root-to-node path. Even the best designed computer programs only collapse this structure to a small extent, getting you close to what you want some of the time.

As stated above, computer programming is not inherently goal directed as is human thinking. They only have goals to extent the programmer is able to understand and customize predetermined scenarios. If user customization is available, it is generally an additional job to do, situation by situation, rather than allowing customization on the fly, without intrusion.

To truly interface with humans at the highest level, especially in any form of knowledge work, a problem solving i.e. goal directed process, must be at the root level of computer design. The design needs to:

1. Incorporate the structure of nodal neural nets: "collapse the tree" by gathering for the human, the nodal information needed to prompt the person where they left off with the problem. In addition, it needs to provide all additional "orientation" to the problem in context, automatically.
2. "Learn" each individual's problem solving goals as the person uses the computer. The program needs to be able to "learn" how the user is interacting with the computer to solve problems. It needs to log what parts of the program they are using. Then it has to have an efficient trigger that allows the user to capture the knowledge and steps they used for that problem, so they can be more efficient the next time. This should be a fluid part of the process, not an extra step or an annoying prompt.
3. Bring forward problem specific problem solving tools/actions that the individual personally uses already, with access to additional problem specific tools/actions that the user has not personally used.
4. Have a status marker available to allow the person to individually assess the state they are leaving the problem in.

Currently, when you want something on a computer, computer programs make you adapt to their "thinking"structure. This is an inherent 20 and $21^{st}$ century computer programming design inefficiency which is eliminated with PSP programming. Instead of adapting to computer designed "efficiency" such as "phone menus," think nodal "thinking".

When you want something on a computer, computer programs make you adapt to their "thinking" structure. This is an inherent $20^{th}$- and $21^{st}$-century computer programming design inefficiency which is eliminated with PSP programming.

What does node level thinking mean? This might be best exemplified by looking at a simple example outside of the medical field. Consider a person who every week withdraws various sums from A.T.M. A PSP designed A.T.M. would be enabled to "learn" from the user what problem they are trying to solve, seamlessly. In this case, the problem is that 98% of the time the person goes to the A.T.M. to get exactly $200, $300, $500 or to make a deposit. Currently, the only "intelligence" offered is the ability to set up a single memorized withdrawal amount. Even this requires a separate job for you to do to set this up for future shortcut.

In most A.T.M. situations, you have to follow a somewhat "collapsed" tree structure to get the money. The human is forced to go through a process that mimics how the computer thinks about the transaction rather than the way the person does. In short, you drive up to the A.T.M. already knowing you want a particular sum of money based on your perceived cash needs in the next few days. This is based on other financial "nodes" that you run through quickly in your drive up to the A.T.M. These thought "nodes" are rapidly put through a goal directed problem solving process, subliminally, to determine the goal of the $ amount you calculate you will need). By arrival, the human knows the amount they want before they put their card in. Over time, these amounts tend to be just a few possibilities that the computer, if truly efficient, would learn from the human. Instead, except for the simplest of situations, the A.T.M. forces you to follow its instructions in a somewhat "collapsed" root-tree-branch-leaf-vein-node process to get what you want.

In this example, the current structure requires you to sign in and touch what type of transaction you want from a menu. In this case the user touches "withdrawal", the user is then presented with the branch, that is, a choice between checking and savings accounts; the leaf "checking" is selected. Then they pick from nodes representing "table of possible dollar amounts", and then click "done". This is followed by another branch that wants to know if you "need a receipt?"

Now, let's take a PSP approach to this simple human/computer interaction. The PSP approach would let the user "macrotize" any repetitive function they do around a problem they need to solve. In this case, the problem to be solved is getting out your money as quickly as possible from the A.T.M., not a dollar less or more than you want. The user would have the ability to set up "on the fly," a macro that accomplishes this. Following the same steps as above, the user is allowed to name the "process" of getting his or her "dollar amount" by naming these transactions at the completion of any A.T.M. withdrawal, if they desired. Over time, they would have as few, or many of such memorized transactions presented to them upon inserting their A.T.M. card.

Following the same steps as above, the user is allowed to name the "process" of getting his or her "dollar amount" by naming these transactions at the completion of any A.T.M. withdrawal, if they desired. Over time, they would have as few, or many of such memorized transactions presented to them upon inserting their A.T.M. card. With this design, in a very short while, the A.T.M. "would learn" how to interact with you in most cases, and present the following display soon as you put your card in:

Do you want
1. My usual $200. No receipt. Then close?
2. My usual $400. No receipt. Then close?
3. $500 with receipt. Then close?
3. Checking deposit. With receipt. Then close?

The person touches the $200 choice and is done. Less time with the A.T.M.; more time with your money!

If a trivial situation like this takes several clicks, imagine the situation an M.D. is faced with in root-tree-branch-leaf-vein-node structured ENMR's! Again, computers, by design, follow a root, tree, branch, leaf, vein, node mechanism to retrieve and write data. The differences in how humans and computers process information is the main reason why computers are perceived as difficult for so many people. With PSP design, the computer still processes information the way they always have; how they display it to the user is the difference. That is, with PSP computer programming, the computer can rapidly go through its root, tree, branch, leaf, vein, node process behind the scenes, and present only veins and nodes to the human. It can effectively collapse the tree or appear to turn the tree upside down. The computer screen will display node—node patterns, readily recognizable to humans. The effects will humanize the computer interface. Learning curves, and "computer design intimidation" will be a thing of the past.

The Four (4) Fundamentals

There are essentially four fundamentals to problem solving in all fields/domains that solve problems over time. The first point that must be recognized is that in almost all knowledge domains, the patient or client comes to the practitioner/consultant to have a problem or problems prevented or solved.

The second point is to recognize that all practitioners in all of these domains solve problems the same way. Specifically, these practitioners apply specialized knowledge sets learned in training and experience with each individual problem until that problem is prevented/resolved or at least improved. If unable to resolve the problem, they exhaust all reasonable remedies before it is mutually agreed upon to stop. To the extent that the practitioner/consultant is able to accomplish this is directly related to their professional reputation in their field.

The third point is that the process is programmable. The PSP follows rules that Applicant has discovered to be universal. The Applicant contends that the PSP is especially relevant to the field of medicine. See K. C. Meyers et al., *The Follow-Up Note: Format and Requirements, Specifications for the Computerized Medical Record*, AMIA Proceedings: Orlando, Fla. (1997).

The fourth point is that the "reduction" of these complex domains to their core work units leads to an extraordinary increase in efficiency, scalability, and flexibility.

This leads to the impression that the program is actually intelligent. It appears to learn from the doctor and over time appears to think like the doctor. This organically adaptive design will have a major impact on usability now and in the future. In fact, the organic nature of its design predicts that the longer one uses PSP Computing in their work, the smarter it becomes.

2. Rules of the Problem Solving Process

Introduction

Problems are solved over time. Only rarely are they completely solved in a single encounter. In the medical field, even a hang nail that is accurately diagnosed is not truly cured until the patient calls back in a week to confirm that it is gone and was not complicated by a secondary infection. The Problem Solving Process (PSP), universal to all problems solved over time, is best expressed in the diagrams and their related text. While these diagrams relate to the specifics of medical care, they can be easily applied to other domains simply by changing the knowledge sets and the names/vocabulary of the "methods" in which the practitioner uses to organize their information/documentation.

In medicine, those methods are a standardized organization of a visit into the following categories. These methods are well known conventions used to compartmentalize the note, and are not an element we are claiming in the invention. The methods include a History as an accumulator for the first person account of the problem and an interrogatory with the patient for relevant clues as to the etiology of the problem. The Exam is learned in the M.D.'s training to look for physical clues indicating health or illness related to the problems at hand. The Assessment summarizes the diagnostic possibilities of the causes of a given problem, and the "why" regarding the plans. The Plans are the final step of the initial visit of the patient and represent the universe of possible medications, treatments, tests or consultations that can be given for that specific problem. This method can be described by the acronym "H.E.A.P." which stands for History, Exam, Assessment, and Plans. FIG. 1 thus shows the initial H.E.A.P. for any problem.

The convention in medicine follows some additional organizational rules that are generally, but not universally applied or required. Generally, there is only one history for each problem, and one assessment for every problem. There is one exam per visit, though their will be problem emphasis within that exam. Even "doing nothing" is a plan, so there is always at least one plan, but their can be any number of plans ordered for a given problem.

Step 1: Knowledge Management

Figure 2:
FIG. 2 is a diagram showing how knowledge, both personal and universe of knowledge, is applied to each segment of the chart.

There is an intersection of the knowledge set around each individual problem that drives the problem specific history, exam, assessment, and plans. As depicted in FIG. 2, this consists of the universe of knowledge that can theoretically, with modern search mechanisms and evidence based standards, be made available for every problem. This universe of knowledge can then be filtered down to a practical list of personal knowledge that the practitioner commonly applies to the problem. This knowledge base can of course be codified to further enhance the value of the documentation that is automatically generated as a result of the problem solving process. This can be done in post visit and intra-visit data analysis and decision support. For sake of illustration, K=universe of knowledge, k=parts of that universe the practitioner values and uses in their own methods and decision making process. The M.D. filters personal knowledge for each problem from the universe of knowledge, influenced by training, talent, education, experience, and continuing education. This knowledge can be applied to each segment of the chart. The M.D. can "add to or subtract from" their personal knowledge sets at any time. Understanding exactly how professionals use knowledge to solve problems is fundamental to the PSP Computer Programming. By intuitively connecting the universe of codified problem specific knowledge to the problem, we add intelligence to the problem solving process. The experiences and judgment of the practitioner now are amplified by the program in every area. To be specific on this point, here are examples of problem specific knowledge as it is used in each section of the medical encounter:

History Section

Problem specific knowledge provides for key questions to be asked in the history section, questions that might be omitted if memory alone is relied upon. For example, asking "if the patient is breast feeding, has allergies or is possibly pregnant" can be life saving and is easily omitted by the human brain. Putting this type of problem specific key question knowledge in the history can prevent errors, especially those of omission. A secondary effect of this is the reduction of lawsuits.

Exam Section

Problem specific knowledge can provide problem specific exam lists in the exam section. This can save a lot of time and again provide safeguards against forgetting to document important negative exam findings. This has both patient safety and malpractice protection aspects.

Assessment Section

Problem specific knowledge is extremely important in the assessment. The assessment is the area that a physician's skill in problem solving is put "on the record". In a well written note, it reflects what the M.D. was thinking and explains why certain actions were taken. PSP computer programming has unique advantages by fully understanding and leveraging how the physician uses their own knowledge and the universe of knowledge in the problem solving process. With the internet, there is virtually no limit to the amount of knowledge available to the practioner at the point of care. In addition, this design allows the user to personalize this knowledge by summarizing what is known from the universe of knowledge about the problem and use it in their own personal knowledge lists or short/smart lists regarding the problem. This can be used to fully write the assessment/analysis of the problem and provide additional details as to the "why" behind the plans being ordered, with a single click of the mouse.

For instance, this can be used to summarize any segment of the available knowledge that the physician would use to analyze the diagnosis, management and potential complications of treatment for a given problem. Specifically, it can be used to discuss the possible complication rate of a recommended procedure, or the exact specificity/sensitivity data for each plan recommended to diagnose and treat a problem. It can be used to discuss the underlying cellular mechanisms, or even the genetic basis of the problem.

Plan Section

All sections in PSP computing utilize "nodal thinking" or "nodal data organization." Nodal thinking is most evident in the plan section. Here, the PSP designed program leverages nodal thinking and provides the M.D. With a problem specific, 'personalized' list of plans with all the details of how they order them. With one click, they can order single or complete sets of plan(s) down to the finest detail. For instance the MRI gives the type of MRI, the location of the test with written driving instructions, the reason for the test, checks for medical necessity and writes an order in one click.

This parallels and further amplifies the M.D.'s thinking at the node level. Specifically, the M.D. Has a patient with a headache that he wants to have an MRI done at one of the 3 hospitals he or she goes to. With one click the M.R.I. is ordered and clear instructions are written on how to schedule it and get to the testing facility; in addition, medical necessity is cleared, and any needed prescription is written. In PSP computer programming, this is automatically provided without additional steps. The M.D. solves the problem; all needed forms and documentation automatically occurs.

In this case, the nodal thinking of the practioner is not only matched by the program, but in providing all the aforementioned outputs, it is greatly enhanced. The M.D. Does not feel obligated to help find the phone number, recommend that the patient call for directions, etc. All of this is a "part of the problem solving process". What good is recommending a test if the patient does not find the facility, or finds out later that the insurance will not cover it? This marrying of "human nodal thinking" with "computer nodal thinking" will create efficiencies and insights not possible with current designs.

Step 2: Minimum Work of the Follow-Up Visit and "Orientation"

The minimum work (as defined by K. C. Meyers et al., *The Follow up note: Format and Requirements, Specifications for the Computerized Medical Record*, AMIA Proceedings: Orlando, Fla. (1997)) is placed in the orientation section in all follow-up visits. This fundamental rule, for every problem, is as follows:

1. The M.D. Must review their last assessment and plan(s) for the problem
2. The M.D. Must review the plan results for that problem that have completed since the last visit
3. The M.D. Must inquire about, or evaluate the current status of the problem Once this is done, if the problem status is resolved/cured, the visit would be complete for that problem even if nothing else is done. Hence the name "minimum work of the visit".

If the problem is not cured, then the M.D. will minimally make a new assessment and plan. If necessary, the M.D. will do an interim history and exam (PX—short for physical exam), on the patient in relation to the problem. As expressed by this author in his article (K. C. Meyers et al., supra), these steps are crucial to the solving of problems over time. Together they are called "orientation". The author contends that this orientation process is not unique to medicine and is used in all problem solving done in all fields/domains that solve problems over time.

As expressed by this author in the article, *The Follow-Up Note: Format and Requirements, Specifications for the Computerized Medical Record*, the three steps of the "Orientation" section are crucial to the solving of problems over time. The author contends that this orientation process is not unique to medicine and is used in all problem solving done in all fields/domains that solve problems over time.

Figure 3:
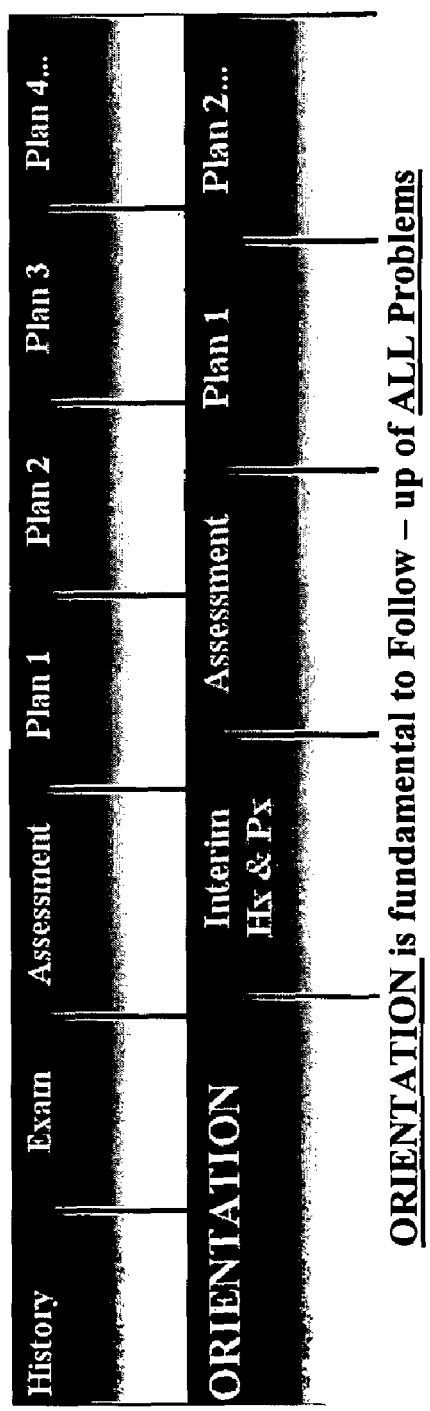
FIG. 3 is a diagram showing orientation is fundamental to follow-up of all problems and includes review assessment and plans, evaluate status and make new assessment.

FIG. 3 depicts a diagram of an initial visit followed by another visit showing the position that orientation takes in the follow-up visit.

Step 3: The Process Repeats Until the Goals of the Problem Solving Process are Reached It is very important to realize that the above process repeats itself, ad infinitum if necessary, to reach the mutual goal of the patient and doctor to stabilize/cure the patient. The orientation, which can be viewed as a standardized way of "starting where you left off", is a critical piece of programming that needs to be in every computerized problem solving process engine to be effective. It matches the logic stream and process of the M.D. Who is seeing the patient and completely eliminates the need for the building of clumsy templates for the 2nd, 3rd, 4th, . . . nth visit for each individual problem type.

Step 4: Orientation Beyond the Individual Problem—the Face Sheet and Problem Solving Tools Important adjuncts to "orientation" around a problem includes the ability to instantaneously get a complete view of the problem in relation to past assessments and plans for the problem, other problems, the severity of the individual problems, historical tables, allergies etc. At the time of the orientation along with the timeline of the problem. This is accomplished by creating a face sheet around all the problems and providing problem views that include prior assessments and plans.

Figure 7:
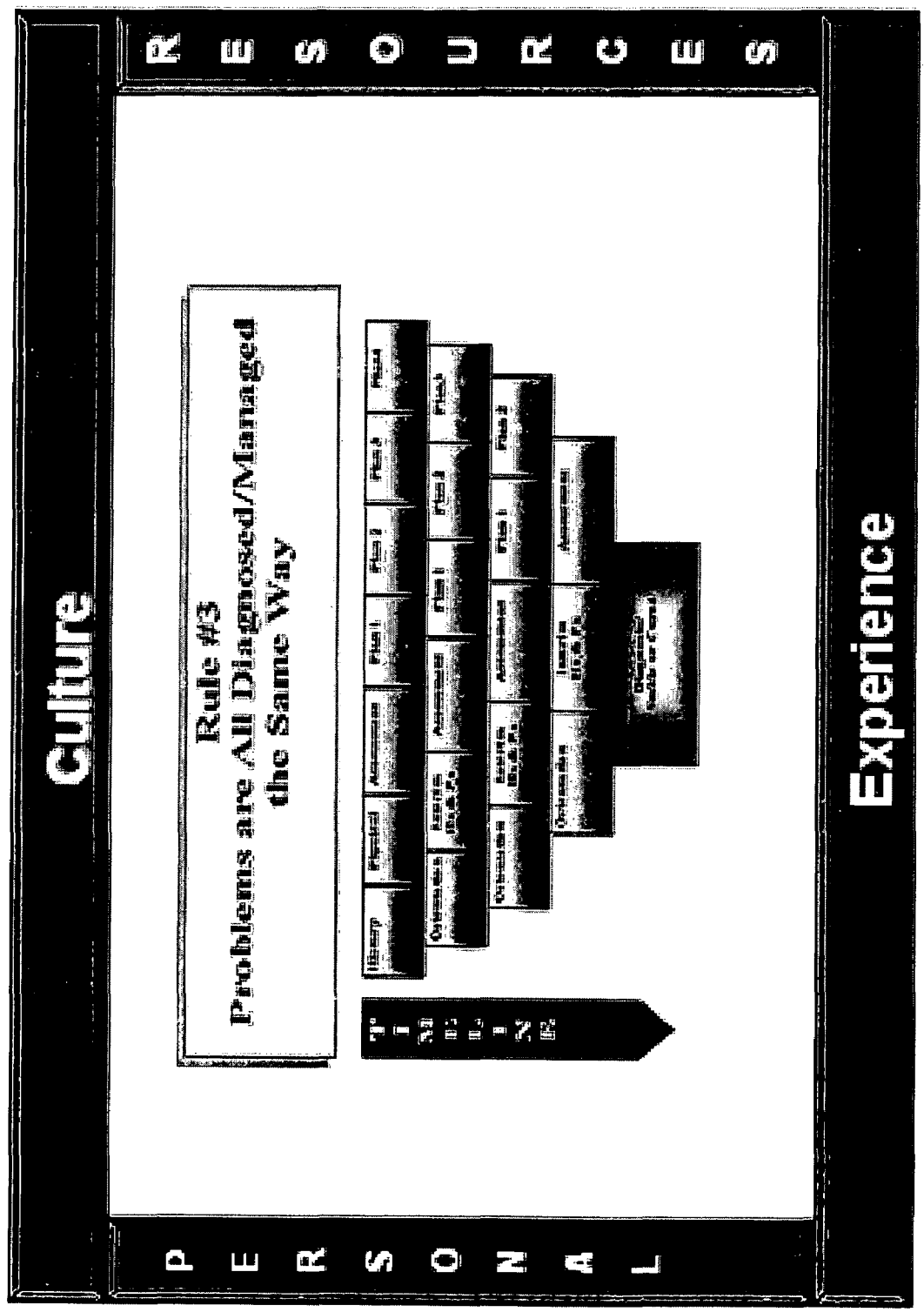
FIG. 7 is a diagram showing the four frames that affect problem definition and decision making.

The face sheet (see e.g. FIG. 7) gives you additional orientation by presenting information on other unique properties this patient has in addition to the problem currently focused on. The M.D.s then adjust their diagnostic and management strategies based on how these elements, along with other plan results, influence the problem's resolution. For example, chest pain in heavy smoker over age 60 with diabetes will dictate a different strategy than a patient who is a nonsmoker, age 30 who also has chest pain.

In addition, problem solving tools are all the possible things the M.D. Will use to prevent/diagnose, stabilize/cure a problem. This includes plans, literature, free text, and other forms of knowledge which are attached to each problem from the M.D.'s personal knowledge list (which he or she obtained from the universe of knowledge available to this problem). In the aforementioned chest pain, the differential diagnosis of chest pain could be added to the note with a single click and the plans for treating and diagnosing the chest pain (such as stress test, cardiac enzymes, cardiology consultation), with all needed documentation would be available in a single click.

Figure 4:
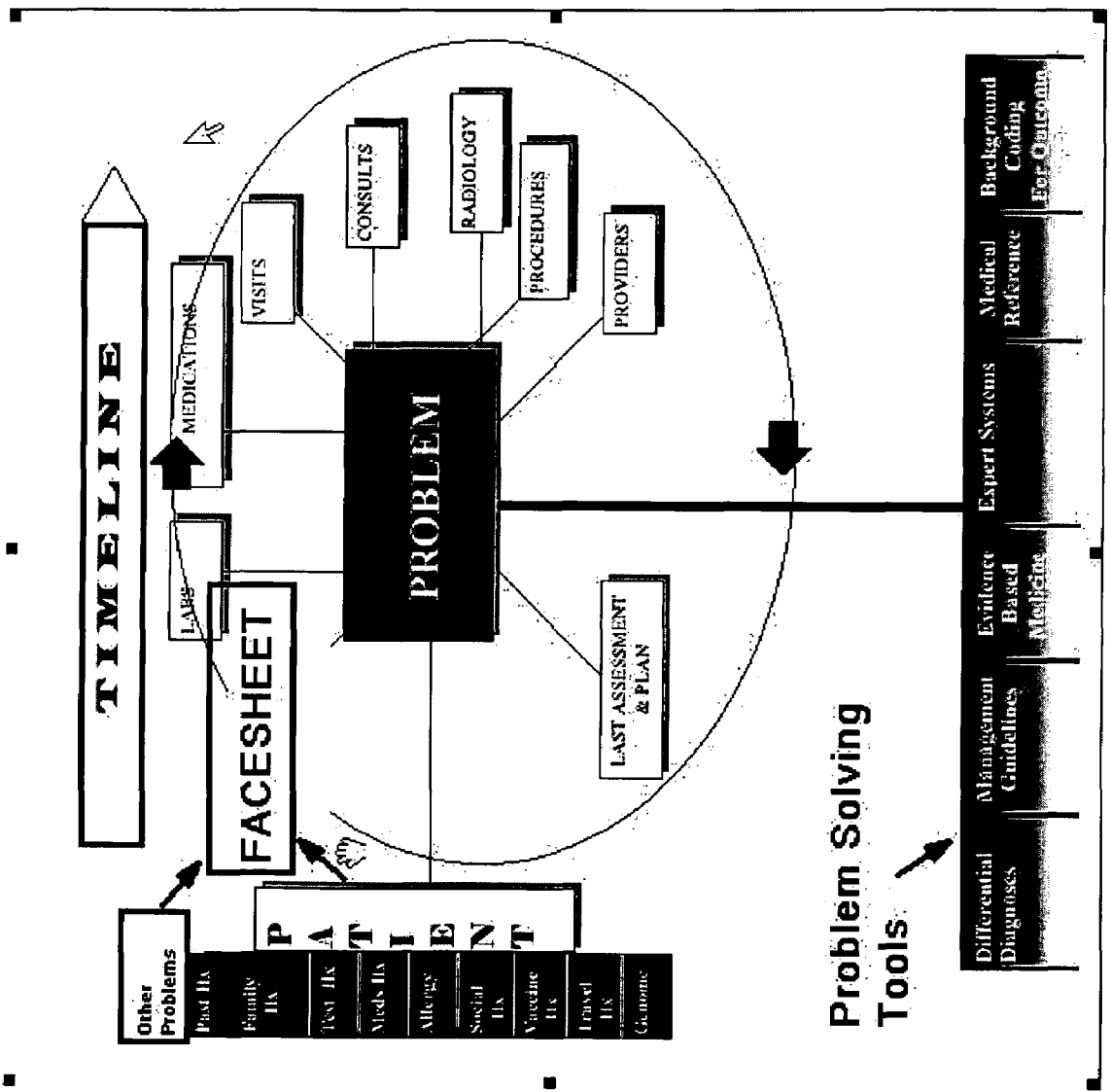
FIG. 4 is a diagram showing the components of the face sheet, used in the process as a contextual orientor, with problem specific tools available to help solve problems.
Figure 5A:
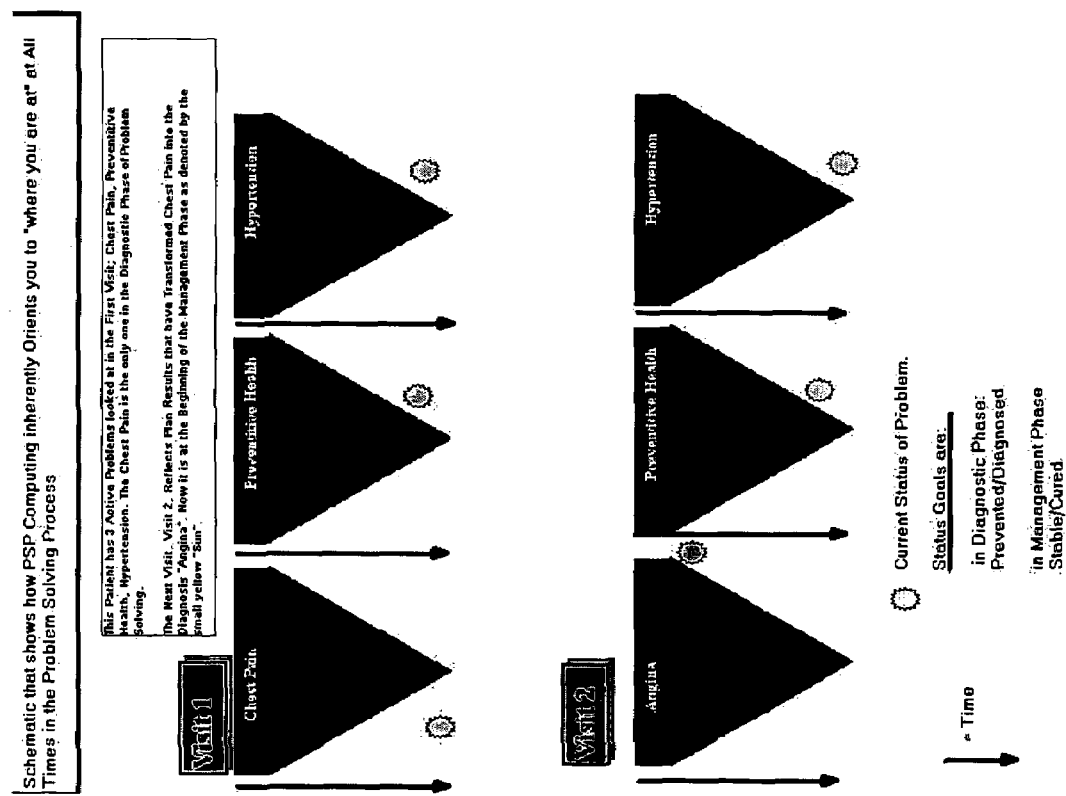
FIG. 5a is a diagram showing the status of each problem denoted by a "sun," graphically summarizing the status of all problems.

The diagram of FIG. 4 illustrates problem solving tools connected to the problem along with all other necessary information to consider the problem in context while seeing a patient for the problem. FIG. 5a is a schematic that shows how PSP computing inherently orients the user to where you are at in the Process at all times. As shown in FIG. 5, the patient has three active problems looked at in the first visit: chest pain, preventive health, and hypertension. The chest pain is the only one in the diagnostic phase of problem solving. The next visit (Visit 2) reflects Plan results that have transformed chest pain into the diagnosis "angina." Now it is at the beginning of the management phase as denoted by the sunburst symbol. In FIG. 5a, the status of each problem is denoted by a "sun" graphically summarizing the status of all problems.

Step 5: Timeline

Problems are "prevented/diagnosed" and "stabilized/cured" over time. This implies there is an onset of the problem. This needs to be captured and relayed to the M.D. as part of the orientation process. In addition to an onset date, the timeline will also display when the M.D. first and last saw the patient for this problem. Furthermore, the timeline signifies the reality that the M.D. is often not personally seeing the patient at the onset of the problem. There are many instances that the M.D. is seeing the patient later in the course of the problem. The patient has already has had evaluations and treatments for the problem. This fact further complicates template-driven EMRs as they try to build a one size fits all template for most problems.

Step 6: Stages of the Problem

Some problems in other domains are clearly identifiable at the onset and are only managed until they are resolved. For example, an accountant may be doing your taxes and interacts with you two to four times until your return is done. This is all problem solving done in the management phase. In medicine, the problem always goes through two phases. The first is a "diagnostic phase" where the problem is diagnosed with a high degree of certainty using the process just described. The second is "management phase," where again the same process is used until it is resolved.

In addition, every problem, like a book, has a beginning, middle, and an end. Recognizing this concept allows for more detailed programming of the problem solving process. We contend that we are additionally unique in recognizing this. In so doing, the program is further able to assist the M.D. By nesting knowledge not just by the problem, but also based on what stage the problem is in. For example, the knowledge used for breast cancer early in the management phase just after a lumpectomy and irradiation is different then the knowledge used in the same patient with breast cancer after they are later in the management phase and they have failed 3 different chemotherapy regimens. This has implications in all knowledge fields/domains.

Step 7: The Orientation Effect of "Problem Status"

The status of the problem is a powerful orientor in itself. Our focus on the problem solving process has given us unique insights in creating prompts that give maximum usability and data organization by design.

Figure 8:
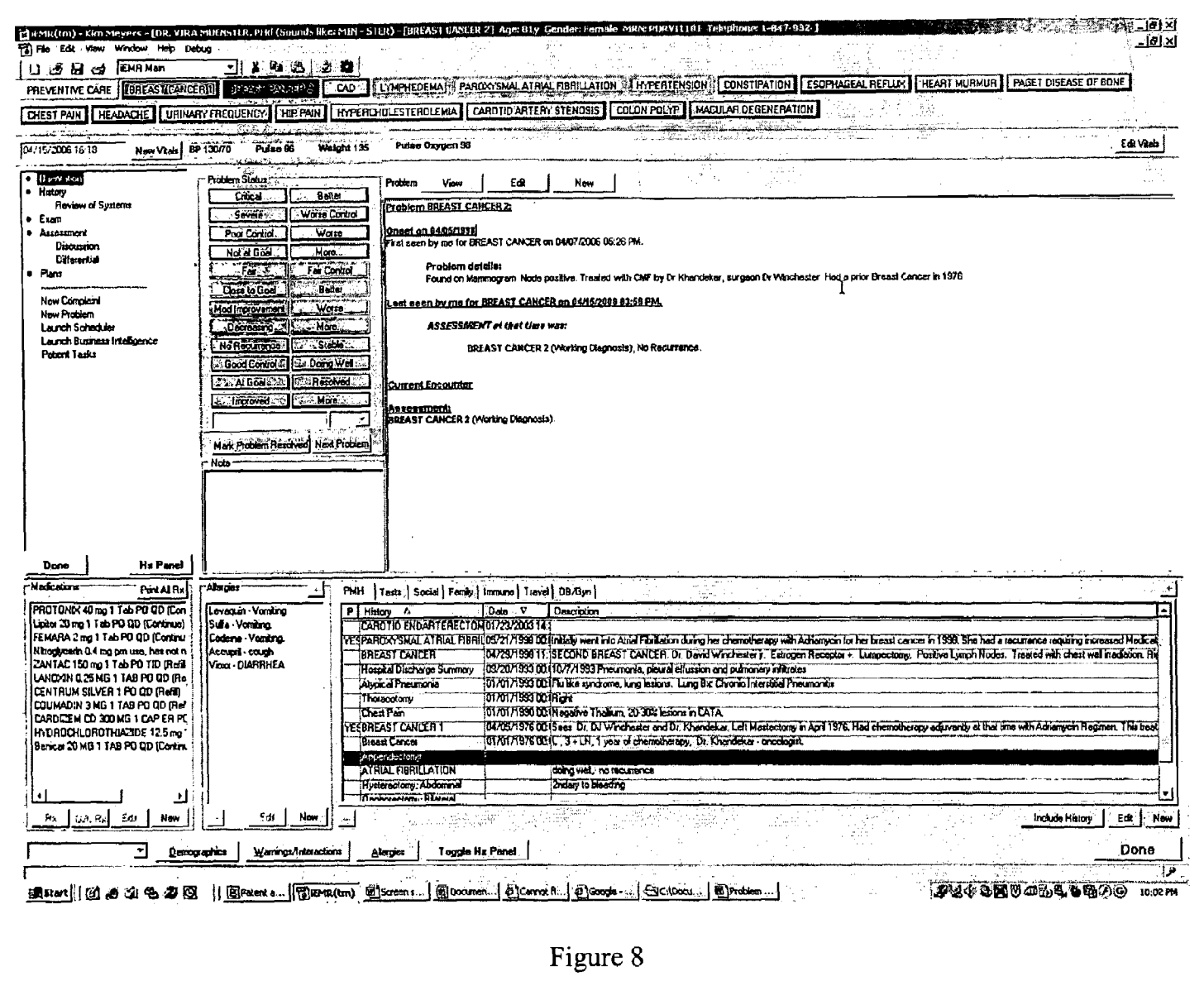

Referring for example to FIG. 8, we use a unique problem bar, where the problems are prominent, individual tabs across the top of the page (elevating them to the highest level of attention). One insight was devising a simple color scheme, red, yellow and green (shown in FIG. 5*b*) to clearly delineate the importance/severity of the problems, as more fully discussed below. This elegantly tells the M.D. where the problem is in terms of the diagnosis/management process This is a powerful orientation tool. By design and organization, the physician instantly knows what to focus their attention on. This is especially useful in patients with multiple problems where it is not immediately clear where one should start. The author has personally tended to patients with greater than 25 active problems. This design was critical to efficiently caring for them.

Step 8: Management Principles

This process is also unique in recognizing that every problem in the management phase has three principles to monitor and bring knowledge to the M.D. that is, the M.D. is primarily interested in the management of the problem, but also must constantly be aware of the complications of the problem and in addition the complications of the plans/treatments used to stabilize/cure the problem.

This is supported again by clustering knowledge around these principles throughout the management phase of each problem. An example would be a patient with diabetes and renal insufficiency secondary to the diabetes, getting a CT scan with dye infusion. This has a high risk of worsening the patient's kidney function and potentially causing permanent renal failure. A PSP EMR would have knowledge of the associated complications of diabetes such as renal failure. It would also have knowledge of what are the possible complications of the CT scan with infusion. Pulling this together the M.D. could be alerted to this and have treatments such as extra intravenous fluids and acetylcysteine brought forward for ordering to help prevent worsening of the renal insufficiency.

In short, the knowledge that could be loaded in the PSP would "know" the possible complications of disease and plans/tests. It would also "know" potential "antidotes" and bring those "antidotes" forward for immediate, single click entry. In so doing, it would efficiently protect the patient, prompt the physician and save time.

Step 9: Problem Solving Goals

The goal of all problem solving, medical or otherwise, is to resolve the problem. In the medical world, this resolution goes through two stages, diagnosis phase and management phase. The processes described above are repeated over time until a diagnosis is made. Some management is done during the diagnosis phase, as a tentative, interim diagnosis is often stated to guide initial treatment. Once the diagnosis is precisely made, the management phase is begun in earnest.

For most problems, beginning the management phase leads to a new, often more detailed evaluation in terms of treatment considerations with a goal of stabilization or cure. The process repeats as clearly described above until that goal is reached or it becomes clear that the goal is not attainable. Even though "cure" is the ultimate goal, a minimum goal of "stable" is often accepted when the state of the art of problem solving for the illness does not lend itself to a cure; for example, type 1 diabetes, hypertension, or metastatic cancers. In these cases, the problems will remain on the problem list with continued attempts to make them as stable as possible. Ultimately in all humans, some problem is not solvable, and it leads to the demise of the patient.

The PSP thus is universal for all problems from birth to death in the medical field/domain. It is also universal in all fields/domains that solve problems over time.

The elements just described are depicted in FIG. 6. The Problem Solving Process is repeated over time with each problem until they are diagnosed. The PSP is again used in the management phase the exact same way with the relentless goal of problem resolution or at least stability. Again, this process is not unique to medicine and it is broadly applicable to all problem solving disciplines and will provide great efficiencies to all domains it is applicable to.

Thus, by "reducing" the complexity of medicine to these elements, each problem is solved and the clinical charting "automatically occurs" as a by-product.

Framing the Problem

Aside from following the above rules of problem solving, the patent applicant has recognized the importance of "framing" in regards to problem solving. This is a significant reason that the problem solving process has not been recognized as common to all problems and professions. It explains why problem solving appears to be different between North America and Europe and between different religious groups. It is the problem framing that these groups apply that differs, not the problem solving process.

Problem framing reveals that there are external constraints on all problems that effect both "what is considered to be the problem" and "decision making". This has led to a focus on programming all the constraint variables rather than recognize and leverage the problem solving process. Instead of utilizing the innate problem solving process that all humans use throughout their day, "artificial intelligence" programs try to anticipate all possible constraints that effect decision making. This is exceedingly difficult to do, and a nightmare to completely personalize for all the states a problem can be in. The patent applicant has accounted for the effects of framing on problem solving and contends that these constrains are external to the problem solving process, and do not change its function. It only changes the exact decisions made, based on the influences of framing. Problem framing is exemplified as follows:

There are essentially four frames that guide the PSP: (1) culture, (2) experience, (3) personal, and (4) resources. The "culture" frame accounts for external constraints such as religious, national, ethnic, corporate, legal, etc. The "personal" frame accounts for external constraints such as motivation, desire, energy, talent, gender etc. The "experience" frame accounts for external constraints such as knowledge, quantity, or quality of past experience. The "resources" frame accounts for external constraints such as personnel, cost, and equipment.

Each frame has individually-defined, variable effects on the problem definition and decisions made. This is why artificial intelligence programs have great difficulty replacing the "human factor." Even right and wrong have personal/cultural underpinnings. Each person has to balance these constraints as they are presented with any problem. The influence of each frame can be immense. However, once a problem is defined, the impact of the framing will then be on the actual decisions made over time but not the PSP.

EXAMPLE 1

Cultural Constraints

As an example of how framing works, let us take the example of how an M.D. views the problem of a hemorrhaging patient, who happens to be a Jehovah's Witness. From their training and experience, the M.D. will know that in order to stabilize this bleeding patient, the M.D. will need to be given the patient more blood. When the M.D. tells the patient that he or she needs blood, as there is a high likelihood of bleeding to death, the patient frames the issue in a personal/cultural way that places religious constraints on the possible plans available to solve the problem. The patient actually views the problem not just as a life-threatening gastro-intestinal bleed. The Jehovah's Witness view of the doctor's recommendation is a far greater problem due to these framing effects. It is viewed as "eternal damnation" if the M.D. proceeds along their normal problem solving mode.

The patient views the situation in a much different view than the M.D. The Jehovah's Witness patient frames the situation with the personal and cultural (religious) constraints and believes that if blood is given, survival likelihood is increased but the patient will have to endure eternal damnation. Thus, the patient refuses treatment. The M.D. is forced to take the most common solution to this uncontrolled bleeding off of the possible solutions list for this individual patient. The M.D., then, would review the prior law on the situation, reflect on the Hippocratic Oath and decide that blood transfusion is not an option. Instead, the M.D. would use increased resources to try to capture the patient's own blood for auto-transfusion.

EXAMPLE 2

Corporate Constraints

How an individual may solve a problem is often subjugated by corporate rules (culture) and financial constraints (resources). These constraints affect what is defined as the problem, and it affects the available plan options, but not the PSP. In the corporate setting, corporate culture will generally overrule the personal frame and sometimes even knowledge as to what decision is made. In addition, financial resources are often a significant restraint.

EXAMPLE 3

Experience and Training

Problem solving in any field/domain that requires training can be much more efficient if the client sees an expert with proper training and vast experience. These also frame the problem and greatly effect decision making. If this is combined with personal framing factors such as empathy, motivation, communication skills, etc. it can lead to outstanding problem solving outcomes for the client/patient in record time. Still, the PSP is not affected. With professionals, lawyers, scientists, M.D.s, etc. the "experience" and "knowledge" along with personal drive tend to have the largest impact on problem solving. This often leads to rapid problem solving which benefits clients and secures reputation of the practitioner.

4. The Intelligent Electronic Medical Record: I.E.M.R.

To display all of the concepts just discussed, the author has programmed an electronic medical record completely around the problem solving process. No matter what problem the M.D. is trying to diagnose or resolve, the process is the same. PSP computing dynamically channels information to the practitioner. This both simplifies and amplifies the problem solving process as it tells the m.d. Exactly where they left off. It also provides problem solving tools that prompt, direct and aid the physician in preventing/diagnosing and stabilizing/curing the patient. The latter is the goal of all medical encounters.

Figure 71:
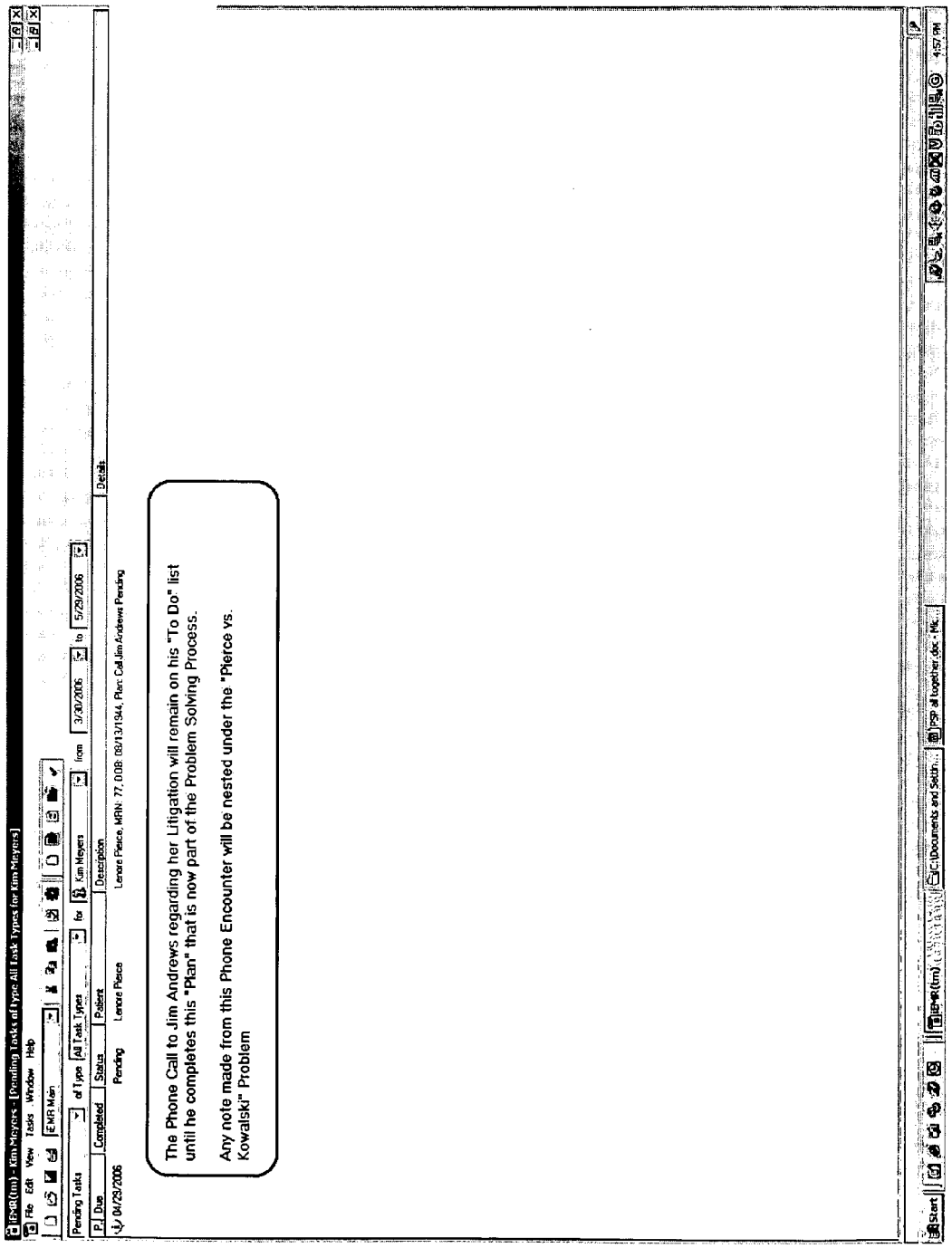

FIGS. 8 to 71 show screen shots of the intelligence of this process in the medical domain. A fully functioning EMR has been built on these principles and if desired, the applicant would be more than willing demonstrate it live. The PSP dynamically channels information to the practitioner. This both simplifies and amplifies the problem solving process as it tells the M.D. exactly where they left off. It also provides problem solving tools that prompt, direct and aid the physician in diagnosing and curing the patient. To display all of the concepts just discussed, the author has programmed an electronic medical record completely around the problem solving process. No matter what problem the M.D. trying to diagnose or resolve, the process is the same. PSP computing dynamically channels information to the practitioner. This both simplifies and amplifies the problem solving process as it tells the M.D. exactly where they left off. It also provides problem solving tools that prompt, direct and aid the physician in preventing/diagnosing and stabilizing/curing the patient. The latter is the goal of all medical encounters.

The screen shots illustrate features of a computer implemented problem solving system utilizing an information storage infrastructure and a flexible development environment for data storage, comprising a stored, user modifiable program including a problem solving rule set relevant to a problem to be solved, a stored, user modifiable set of vocabularies related to a problem to be solved, at least one stored, user modifiable knowledge set relevant to a problem to be solved, and stored, user modifiable individual user preferences relevant to a problem to be solved.

The set of vocabularies, said at least one knowledge set and said individual user preferences comprise a relational database including plurality of tables having a table driven infrastructure. The system also includes a display screen, and the computer generates a screen display including user viewable and modifiable display portions corresponding to the set of vocabularies, the at least one knowledge set and the individual user preferences. The set of vocabularies, the at least one knowledge set and the individual user preferences may be user modified by adding, editing, and deleting elements. User accessible means in the screen display may be used for retrieving net based information for adding to the set of vocabularies, the at least one knowledge set and the individual user preferences. The program is capable of tracking the adding, editing, and deleting with user, date, and data value information and for processing user requests to modify using rules governing relationships among the elements of said set of vocabularies, said at least one knowledge set and the individual user preferences.

A related computer implemented problem solving method utilizes the information storage infrastructure and flexible development environment for data storage and generates screen displays on the display screen. A problem identified by an initial assessment is entered to the computer at a designated place in one of the screen displays. The user selects from at least one of the screen displays at least one item from at least one of the stored, user modifiable set of vocabularies related to a problem to be solved, the at least one stored, user modifiable knowledge set relevant to a problem to be solved, and the stored, user modifiable individual user preferences relevant to a problem to be solved and enters the at least one item to the computer at a designated place in one of the screen displays.

The illustrated embodiment comprises a system for creating an electronic medical record using the computer implemented problem solving system having an information storage infrastructure and a flexible development environment for data storage. The problem solving rule set is relevant to medical diagnosis and treatment. The stored, user modifiable set of vocabularies is related to medical diagnosis and treatment, the at least one stored, user modifiable knowledge set, and the stored, user modifiable individual user preferences are relevant to medical diagnosis and treatment.

Referring now to the screen shots, FIG. 8 shows an iEMR Face Sheet, which is an amalgamation of general facts about the patient. This is an extremely useful view of a patient's problem in context with other problems and personal histories the patient has.

Figure 9:
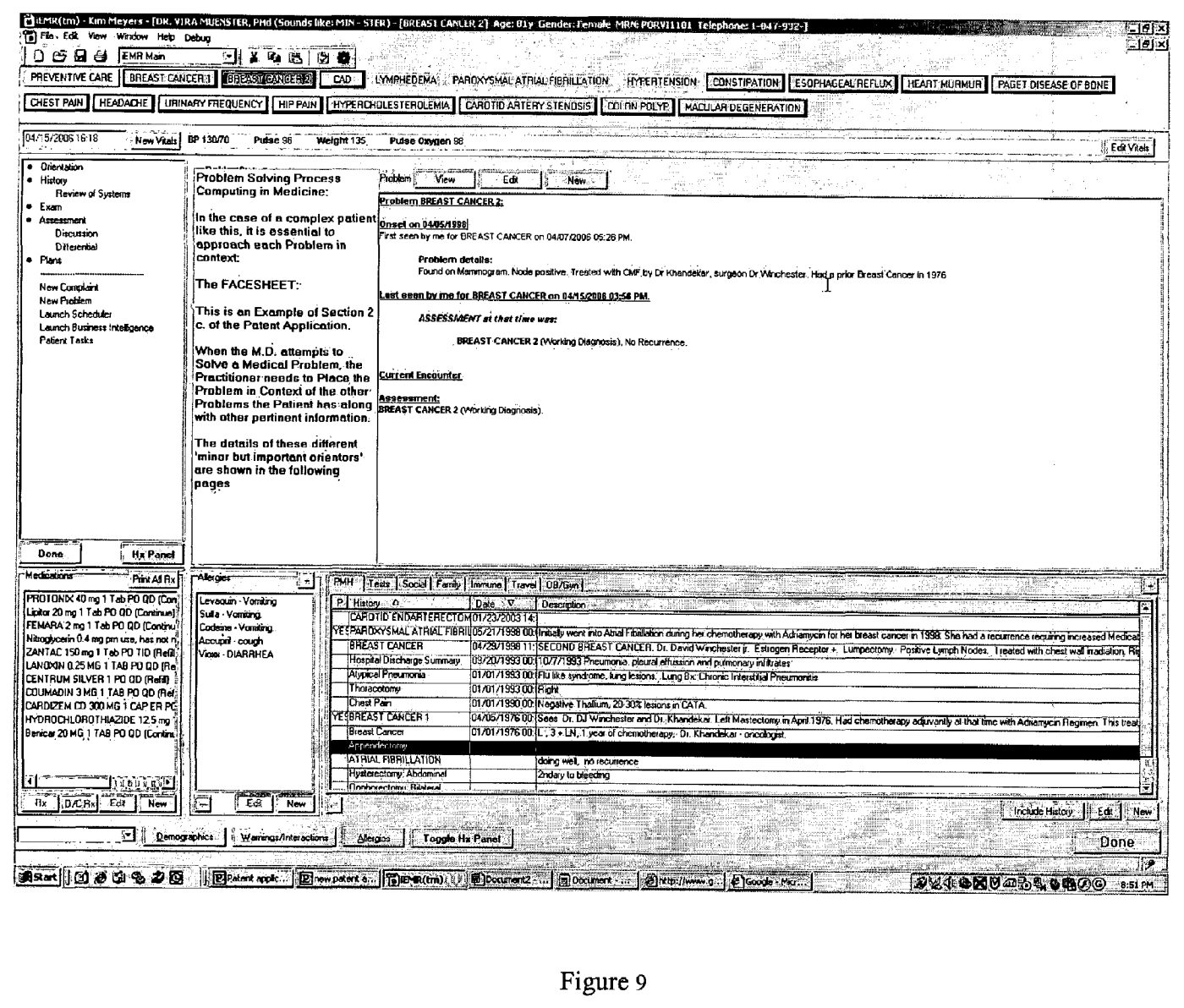

FIG. 9. Problem solving process, computing in medicine: in the case of a complex patient like this, it is essential to approach each problem in context. The face sheet: When the M.D. Attempts to solve a medical problem, the practitioner needs to place the problem in context of the other problems the patient has along with other pertinent information. The details of these different 'minor but important orientors' are shown in the following pages.

FIG. 10. The face sheet is an amalgamation of general facts about the patient. This is an extremely useful view of a patient's problem in context with other problems and personal histories the patient has.

(1) starting at 1 at the top of page, it shows the patients name and other identifiers.

(2) number 2 is the problem list. This consists of all active problems the patient has. This is an essential component of all decisions made about the patient. For example, a back pain in an 80 year-old woman with a history of 2 breast cancers, has more potential for a serious underlying cause, then a back pain in a 24 year-old woman with no problems on her problem list.

(3) vital signs represent current pulse, blood pressure etc. . . .

(4) current medications and allergies are the $4^{th}$ component. The information contained here needs to be considered against every treatment decision.

(5) the history tables are discussed on the next page.

Figure 11:
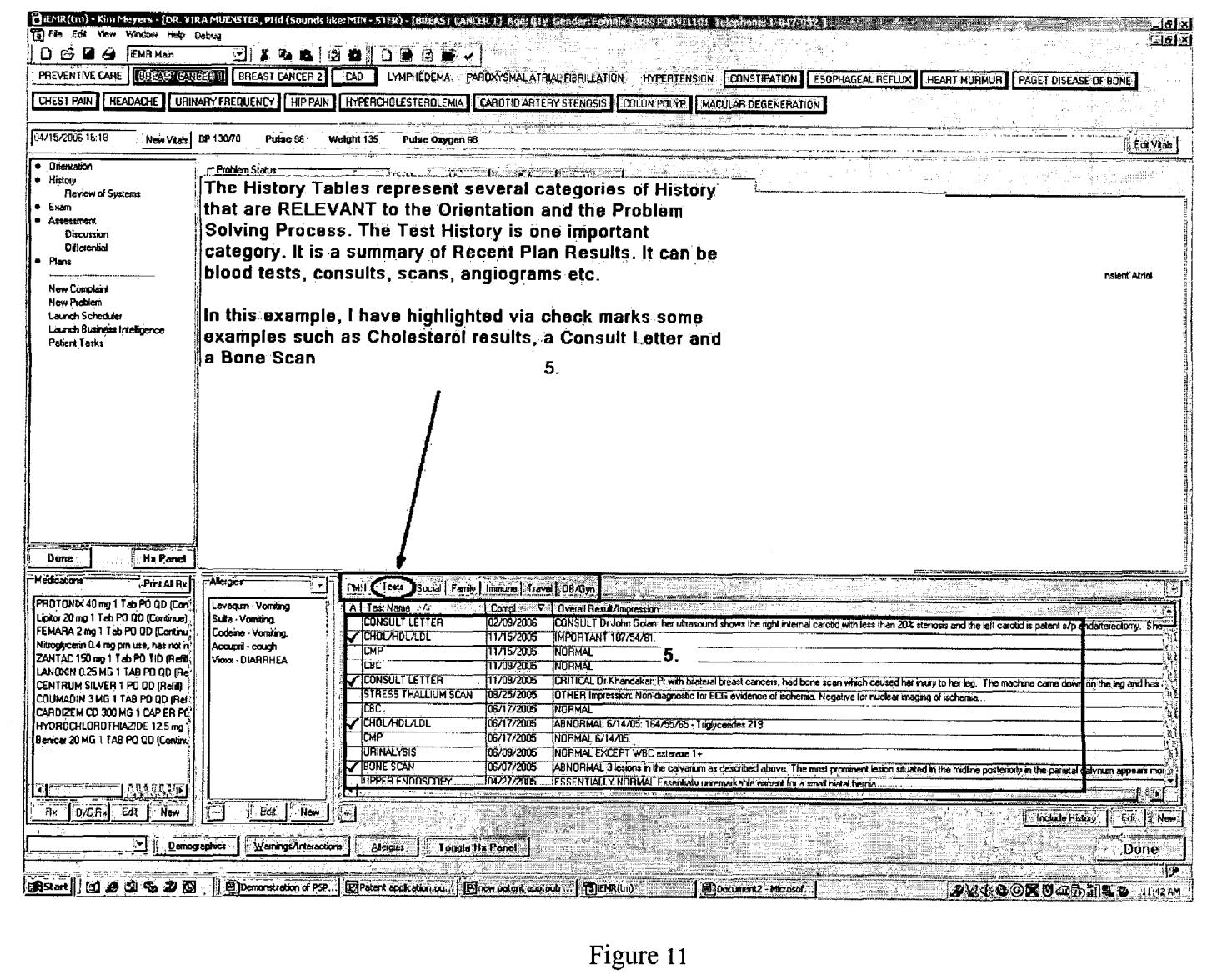

FIG. 11. The history tables represent several categories of history that are relevant to the orientation and the problem solving process. The test history is one important category. It is a summary of recent plan results. It can be blood tests, consult, scans, angiograms, etc. In this example, highlighted via check marks are some examples such as cholesterol results, a consult letter and a bone scan.

Figure 12:
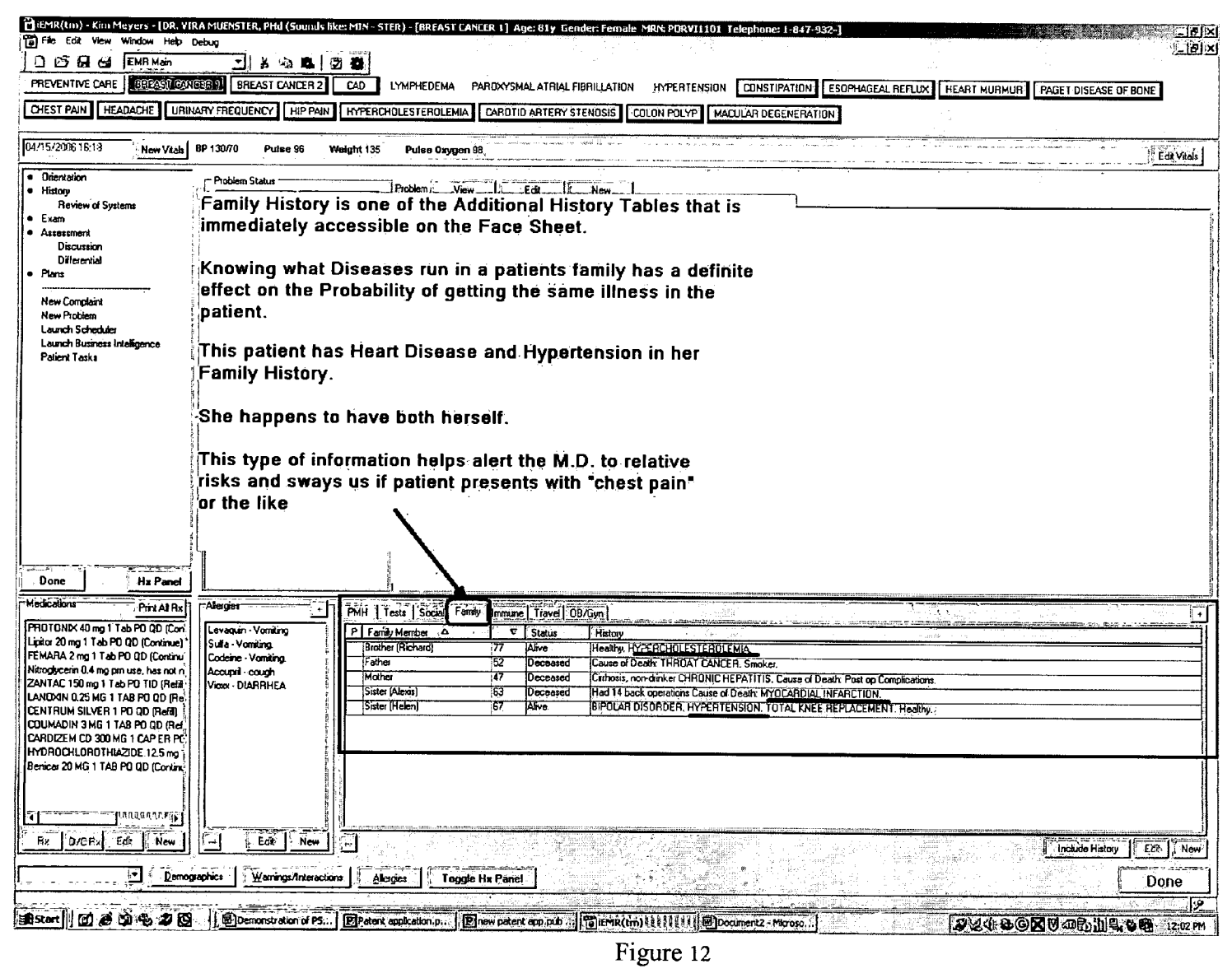

FIG. 12. Family history is one of the additional history tables that is immediately accessible on the face sheet. Knowing what diseases run in a patients' family has a definite effect on the probability of getting the same illness in the patient. This patient has heart disease and hypertension in her family history. She happens to have both herself. This type of information helps alert the M.D. To relative risks and sways us if patient presents with "chest pain" or the like.

Figure 13:
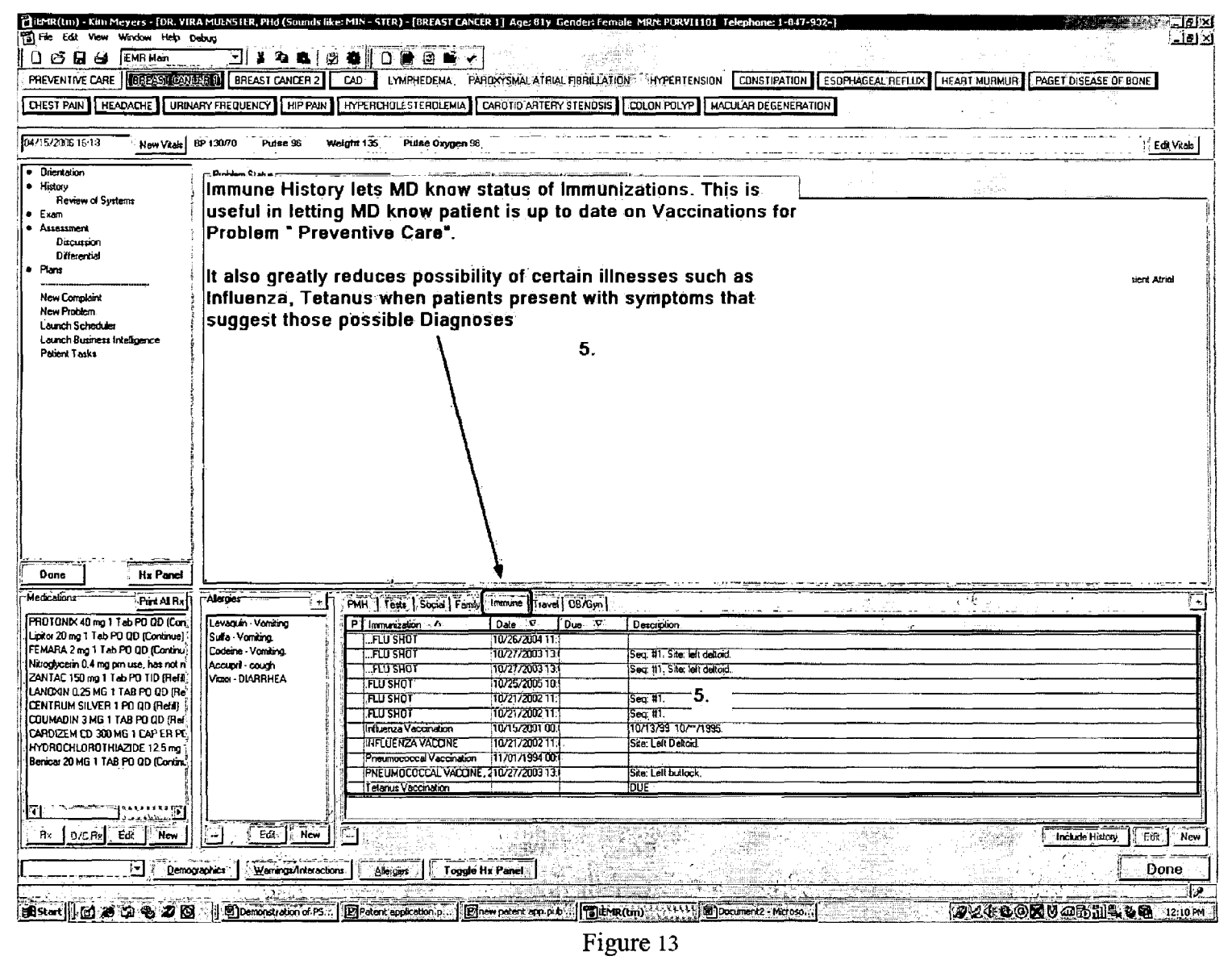

FIG. 13. Immune history lets M.D. know status of immunizations. This is useful in letting M.D. know patient is up to date on vaccinations for problem "preventive care." It also greatly reduces possibility of certain illnesses such as influenza, tetanus when patients present with symptoms that suggest those possible diagnoses.

Figure 14:
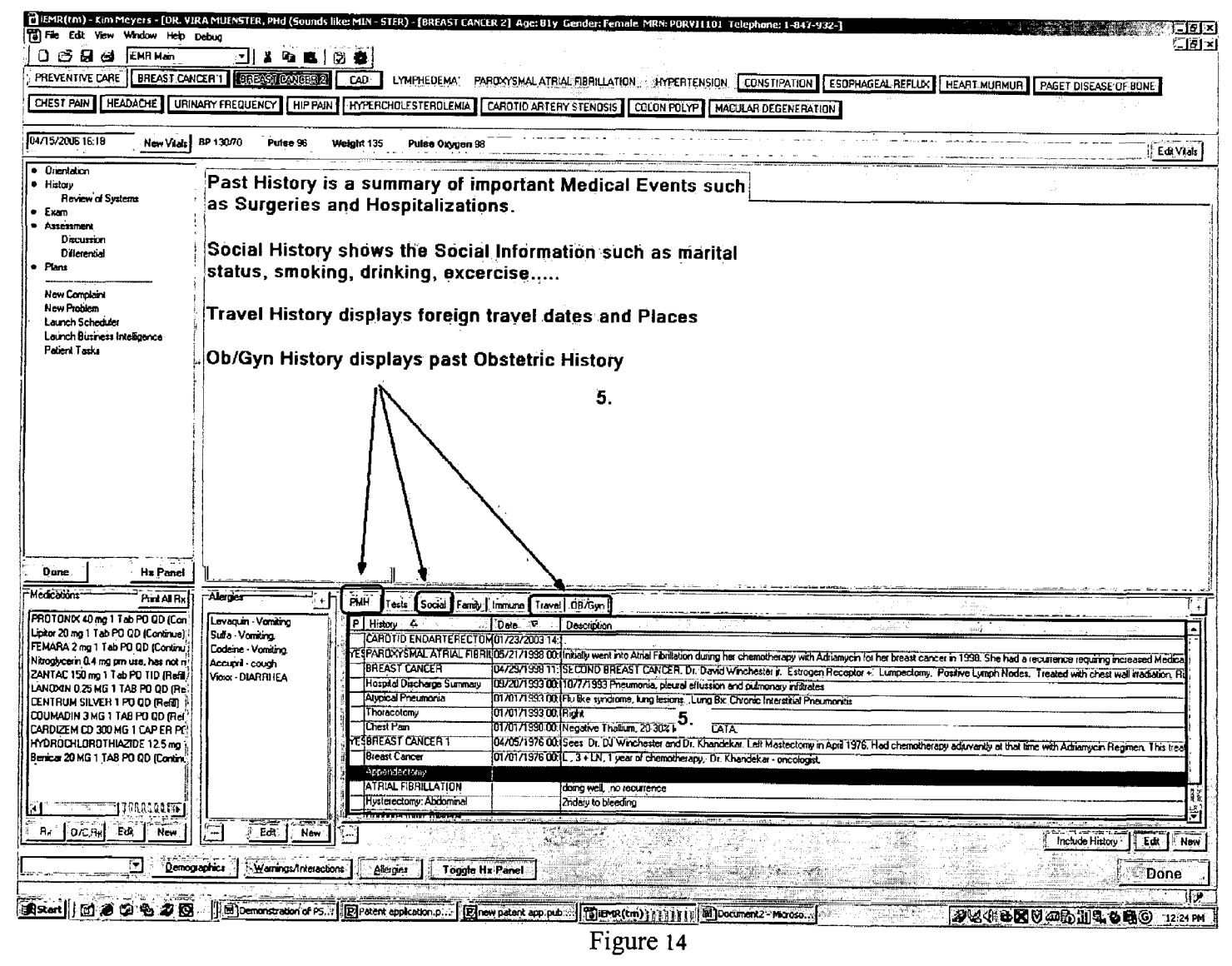

FIG. 14. Past history is a summary of important medical events such as surgeries and hospitalizations. Social history shows the social information such as marital status, smoking, drinking, exercise. Travel history displays foreign travel dates and places. Ob/gyn history displays past obstetric history.

Figure 15:
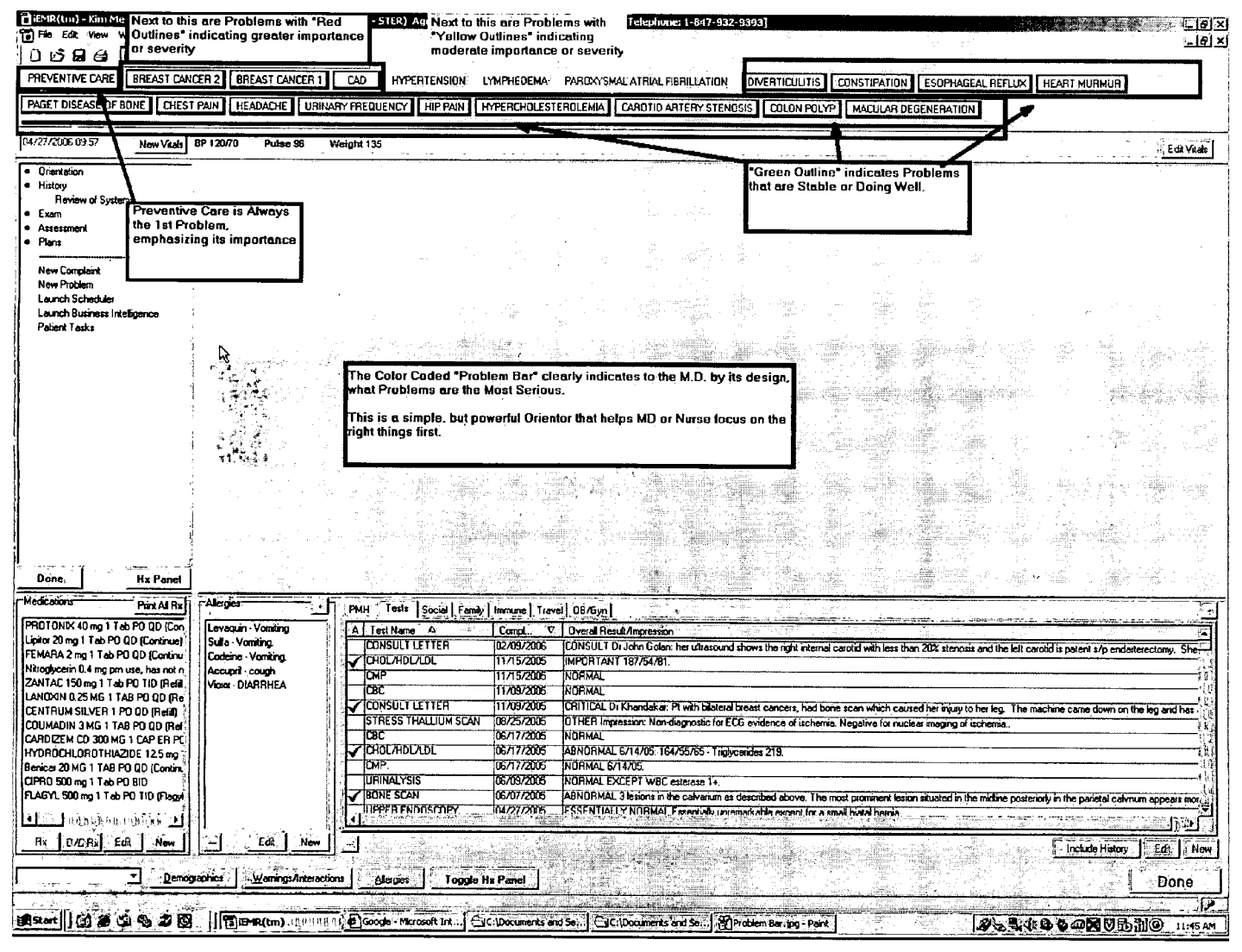
Figure 16:
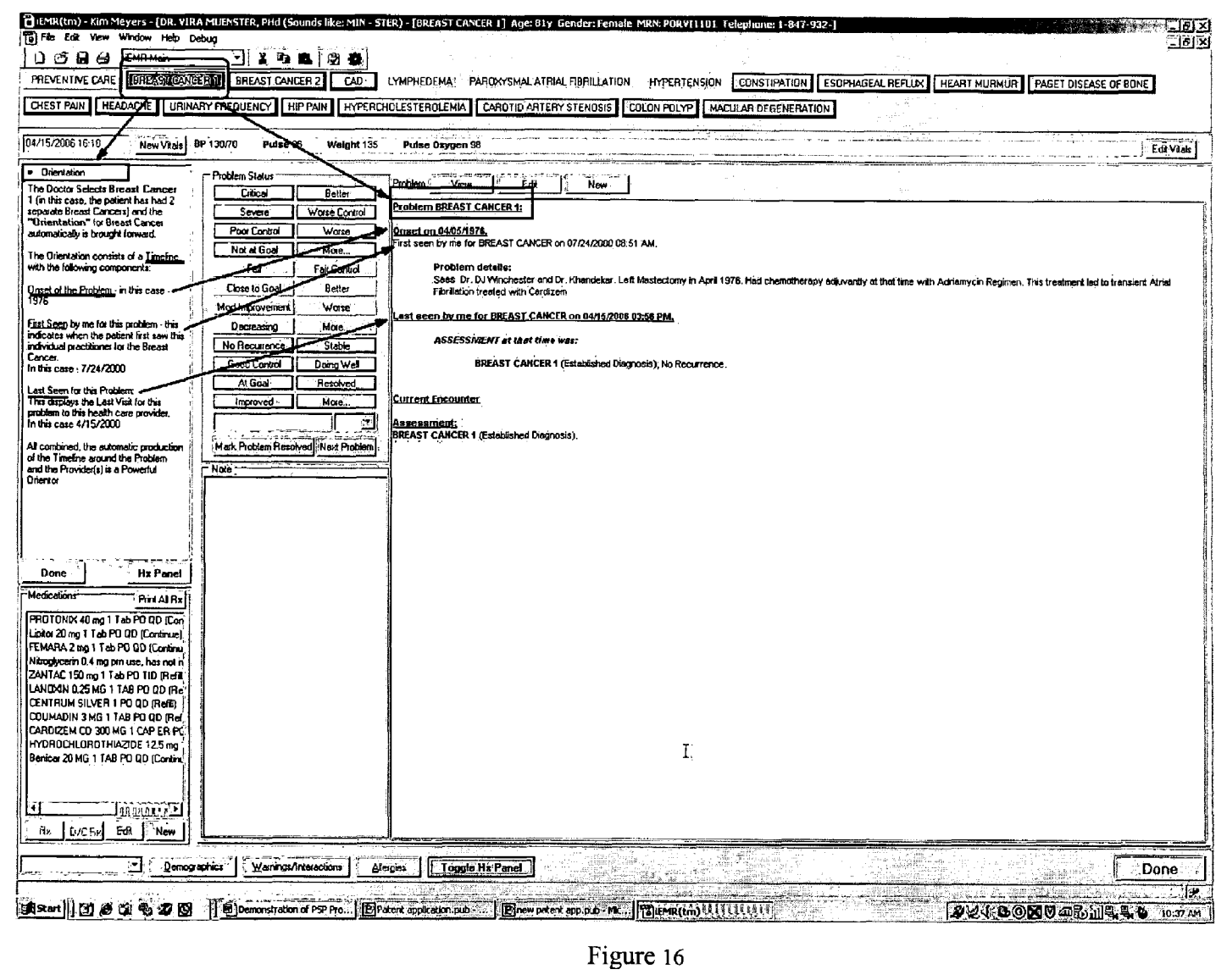

FIGS. 15 and 16. Preventative care is always the $1^{st}$ problem, emphasizing its importance.

The "green outline" indicates problems that are stable or dong well. The color coded "problem bar" clearly indicates to the M.D. by its design, what problems are the most serious. This is a simple, but powerful orientor that helps M.D. or nurses focus on the right things first. FIG. 15 shows M.D.'s notes for breast cancer diagnosis.

Figure 17:
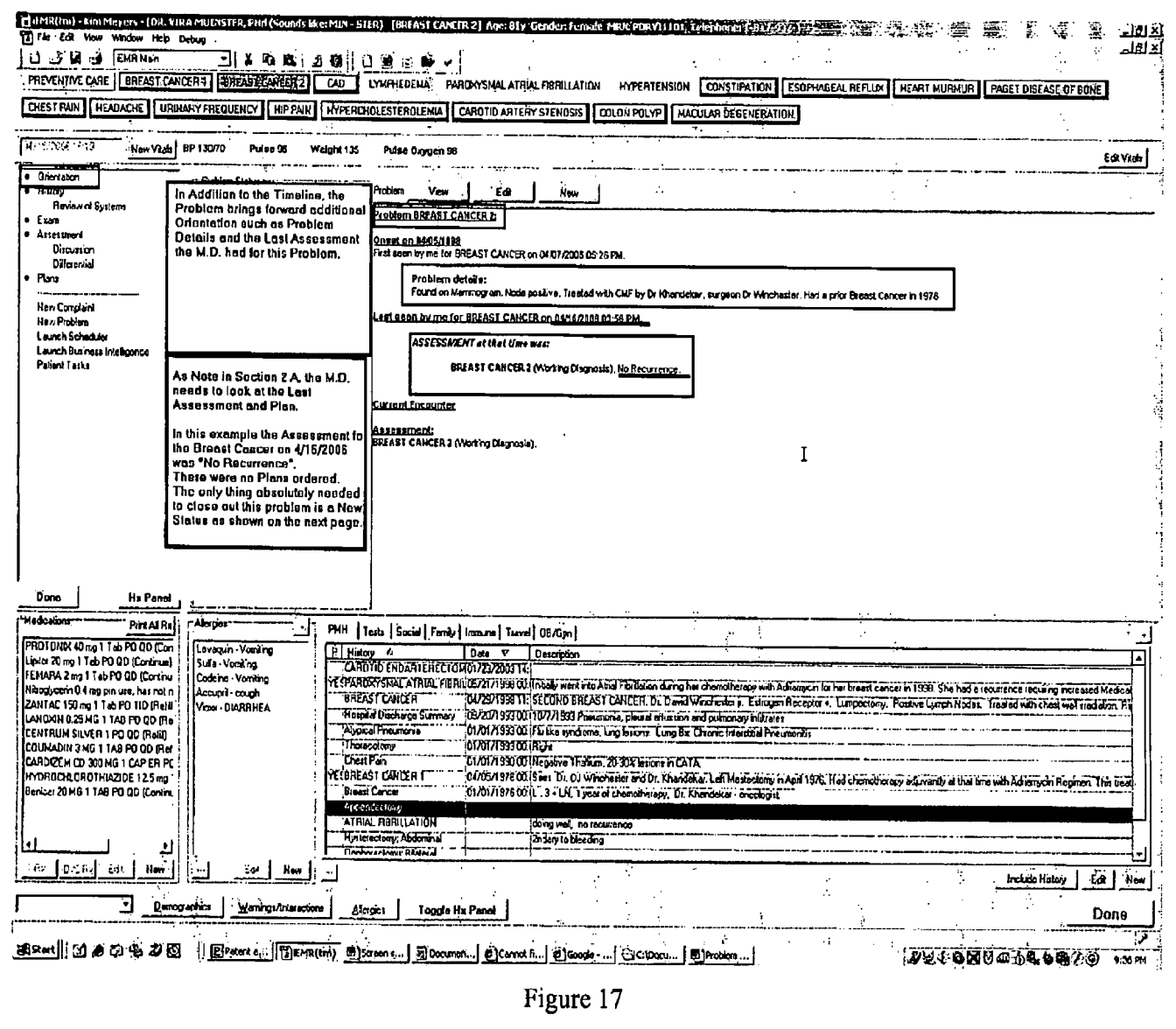

FIG. 17. In addition to the timeline, the problem brings forward additional orientation such as problem details and the last assessment the M.D. had for this problem. The M.D. needs to look at the last assessment and plan. In this example the assessment of the breast cancer on Apr. 15, 2006 was "no recurrence." There were no plans ordered. The only thing absolutely needed to close out this problem is a new status as shown on the next page.

Figure 18:
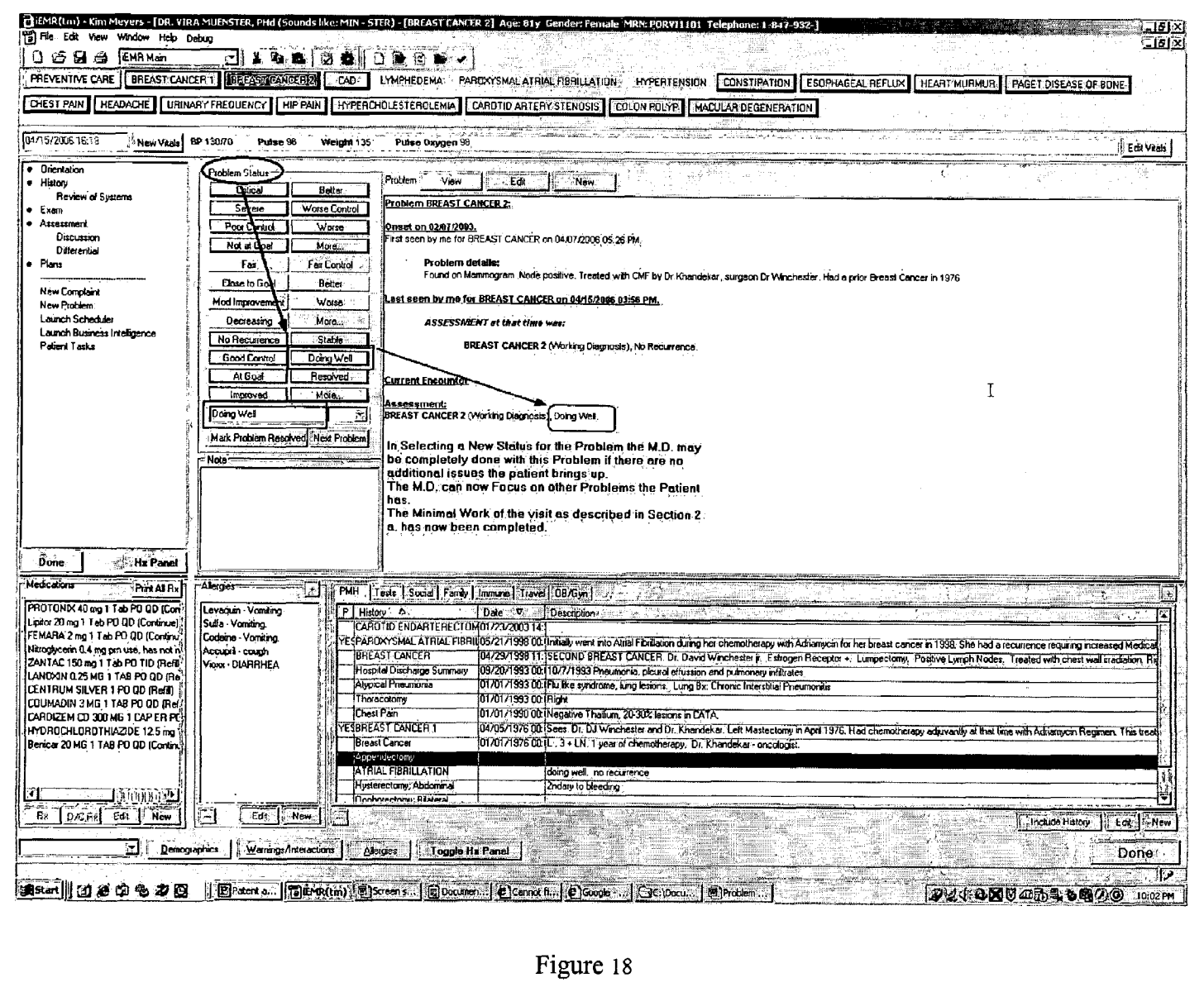

FIG. 18. In selecting a new status for the problem the M.D. may be completely done with this problem if there are no additional issues the patient brings up. The M.D. can now focus on other problems the patient has. The minimal work of the visit has now been completed.

Figure 19:
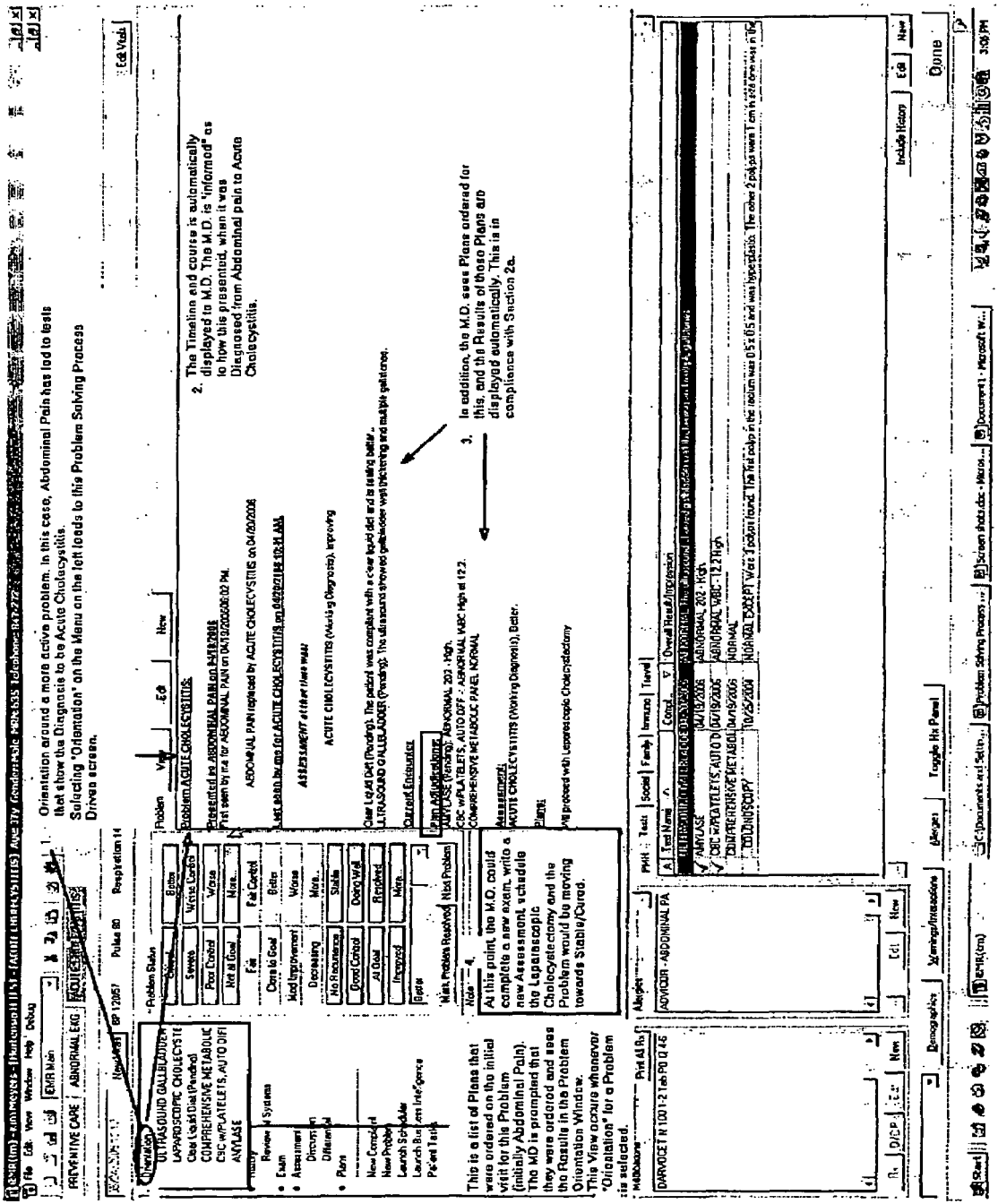

FIG. 19. Orientation around a more active problem. (1) In this case, abdominal pain has led to tests that show the diagnosis to be acute cholecystitis. Selecting "orientation" on the menu on the left leads to this problem solving process driven screen. (2) The timeline and course is automatically displayed to M.D. The M.D. is "informed" as to how this presented, when it was diagnosed from abdominal pain to acute cholecystitis. (3) In addition, the M.D. sees plans ordered for this, and the results of those plans are displayed automatically.

Figure 20:
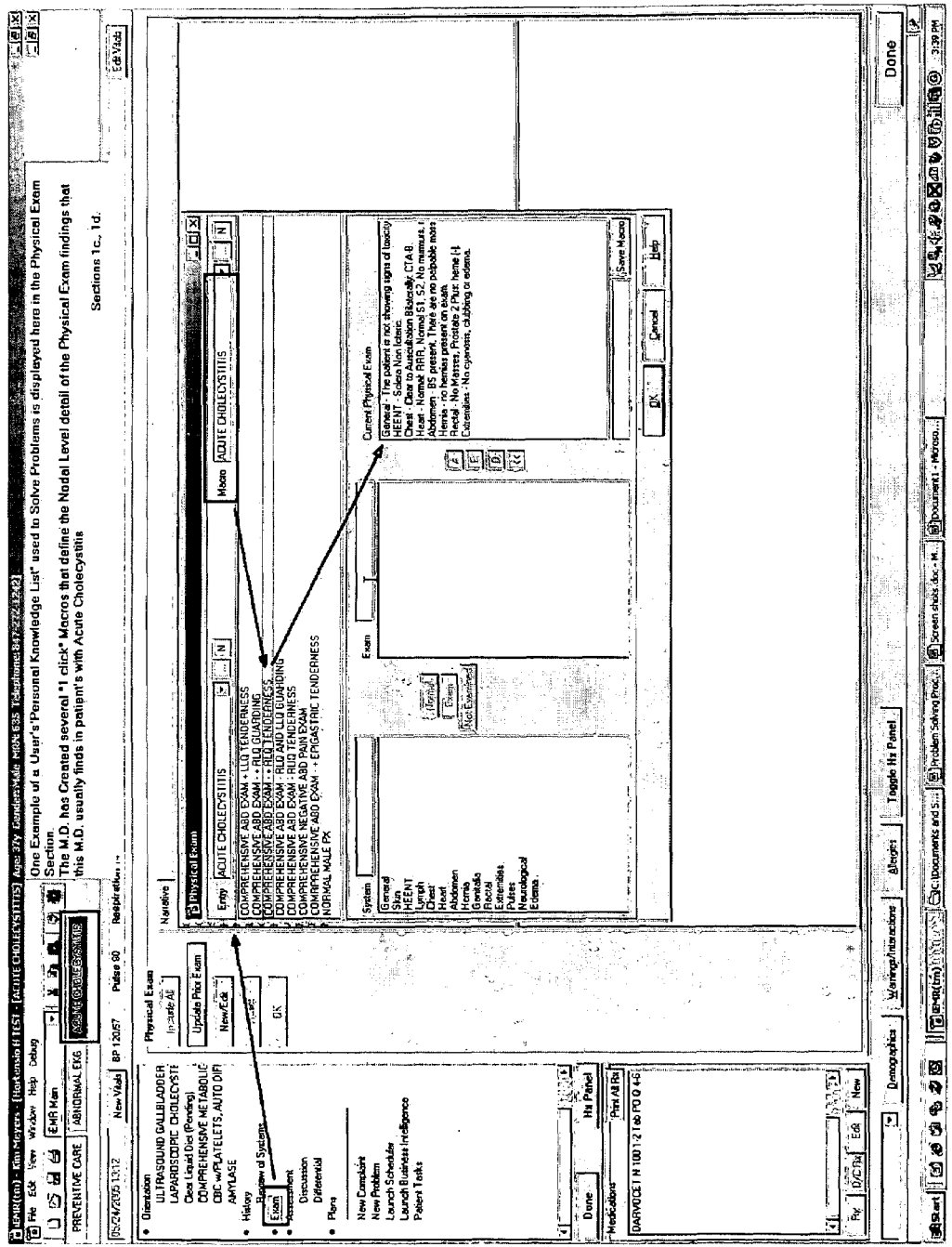

FIG. 20. One example of a user's "personal knowledge list" used to solve problems is displayed here in the physical exam section. The M.D. has created several "1 click" macros that define the nodal level detail of the physical exam findings that this M.D. usually uses in patients with acute cholecystitis.

Figure 21:
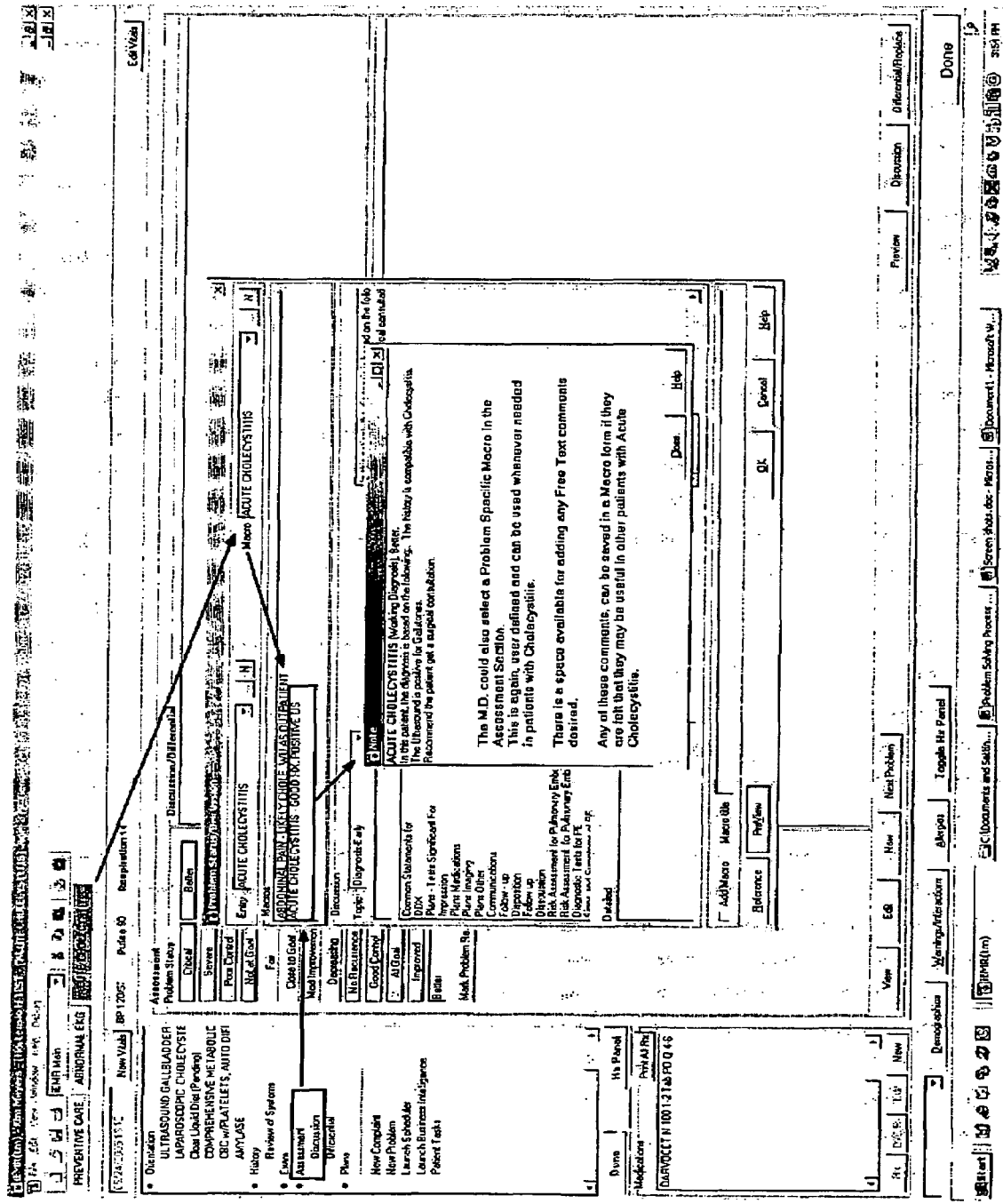

FIG. 21. The M.D. Could also select a problem specific macro in the assessment section. This is again, user defined and can be used whenever needed in patients with cholecystitis. There is a space available for adding any free text comments desired. Any of these comments, can be saved in a macro form if they are felt that they may be useful in other patients with acute cholecrystitis.

Figure 22:
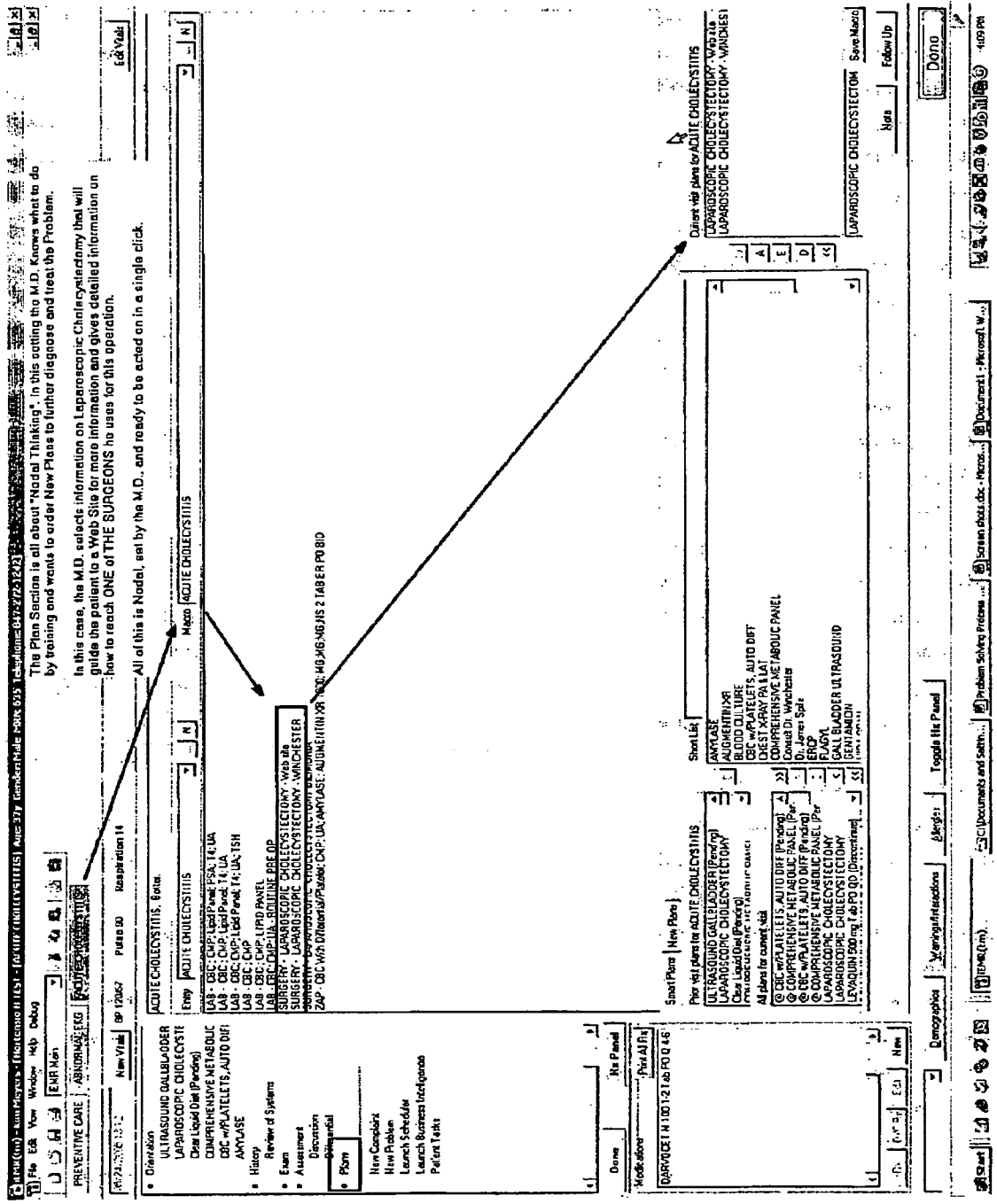
Figure 23:
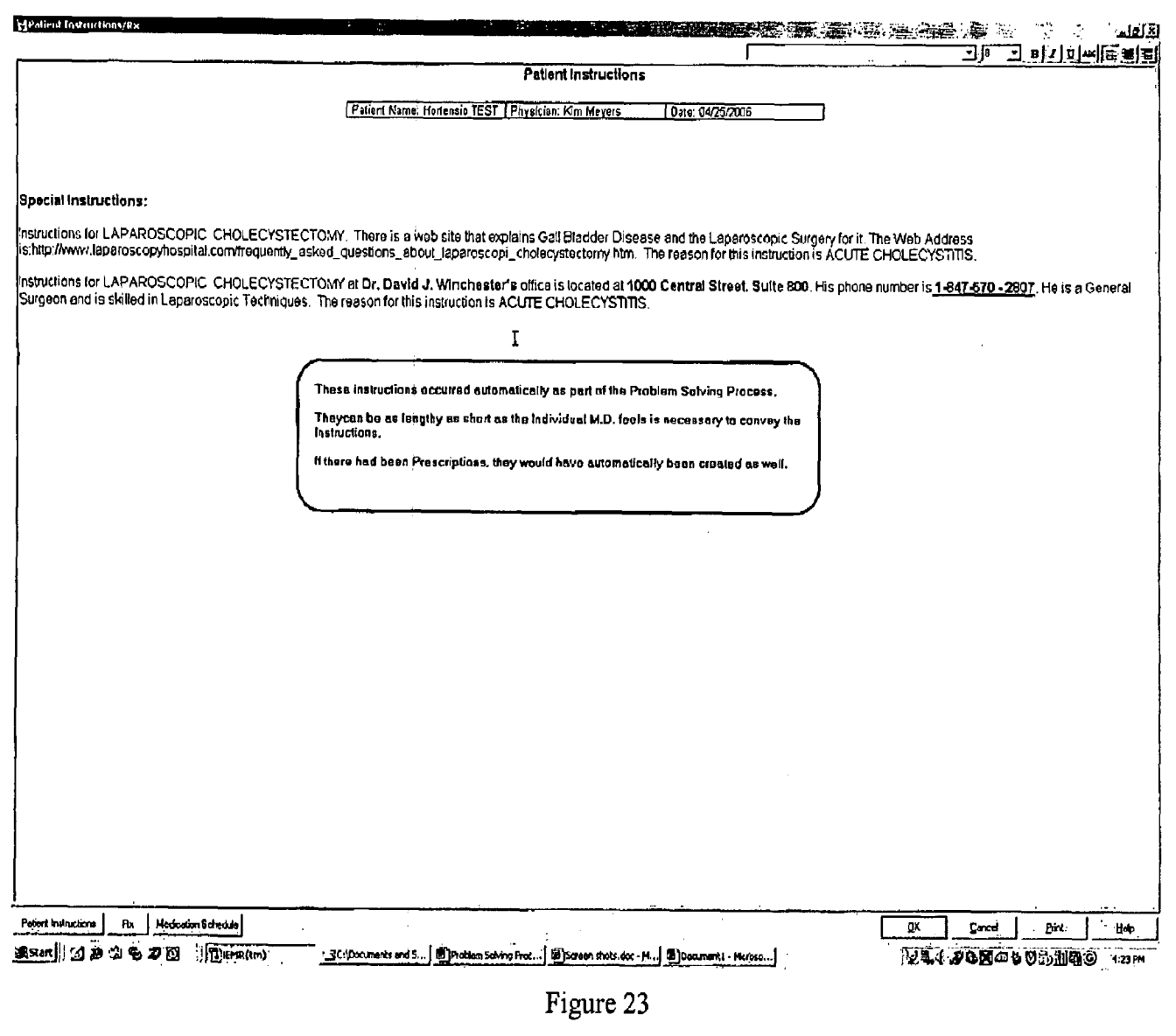

FIG. 22. The plan section is all about "nodal thinking." In this setting the M.D. knows what to do by training and wants to order new plans to further diagnose and treat the problem. In this case, the M.D. Selects information on laparoscopic cholecystectomy that will guide the patient to a web site for more information and gives detailed FIG. 23. These instructions occurred automatically as part of the problem solving process. They can be as lengthy as or as short as the individual M.D. Feels is necessary to convey the instructions. If there had been prescriptions, they would have automatically been created as well.

Figure 24:
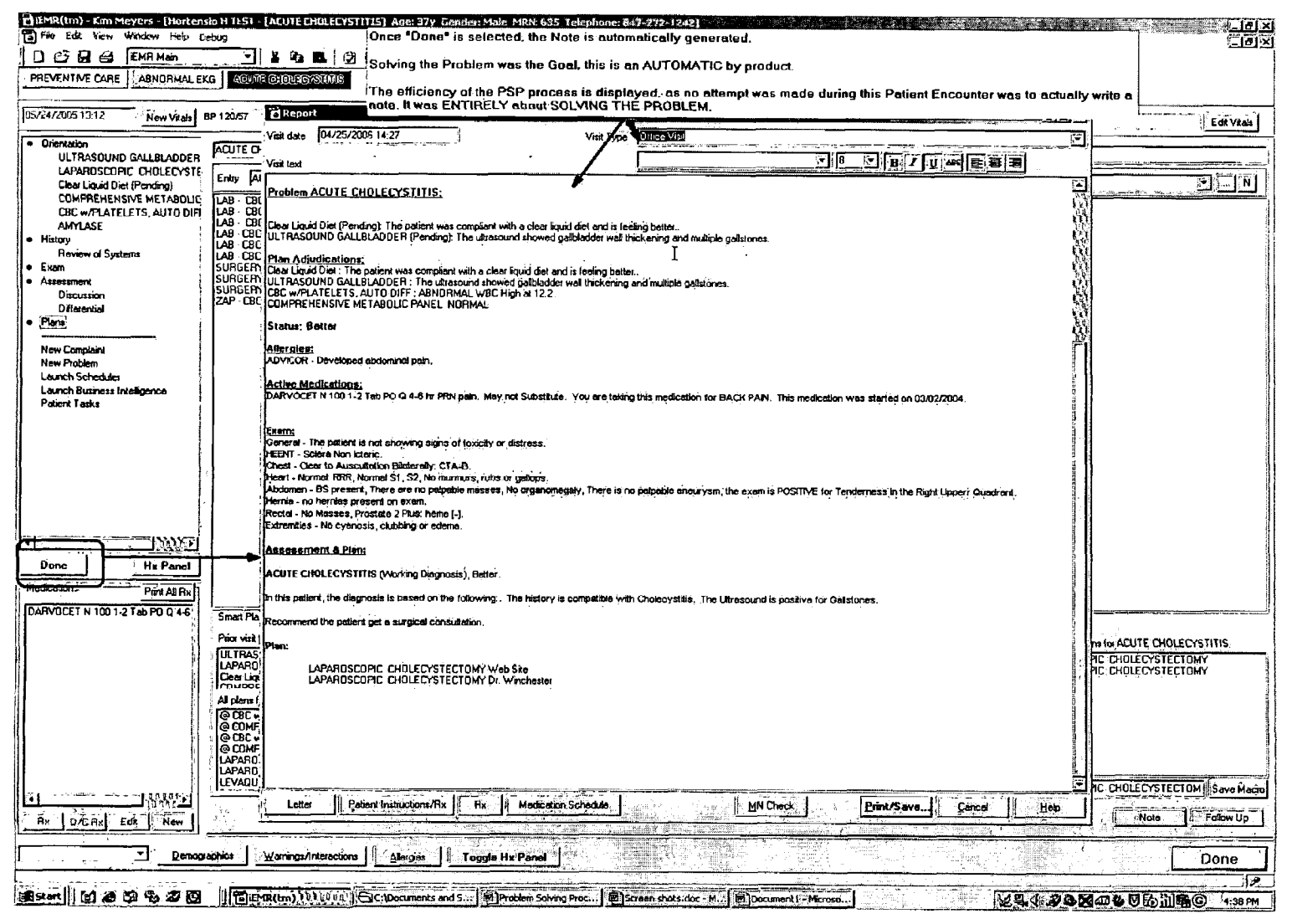

FIG. 24. Once "done" is selected, the note is automatically generated. Solving the problem was the goal, this is an automatic by product. The efficiency of the PSP process is displayed, as no attempt was made during this patient encounter was to actually write a note. It was entirely about solving the problem.

Figure 25:
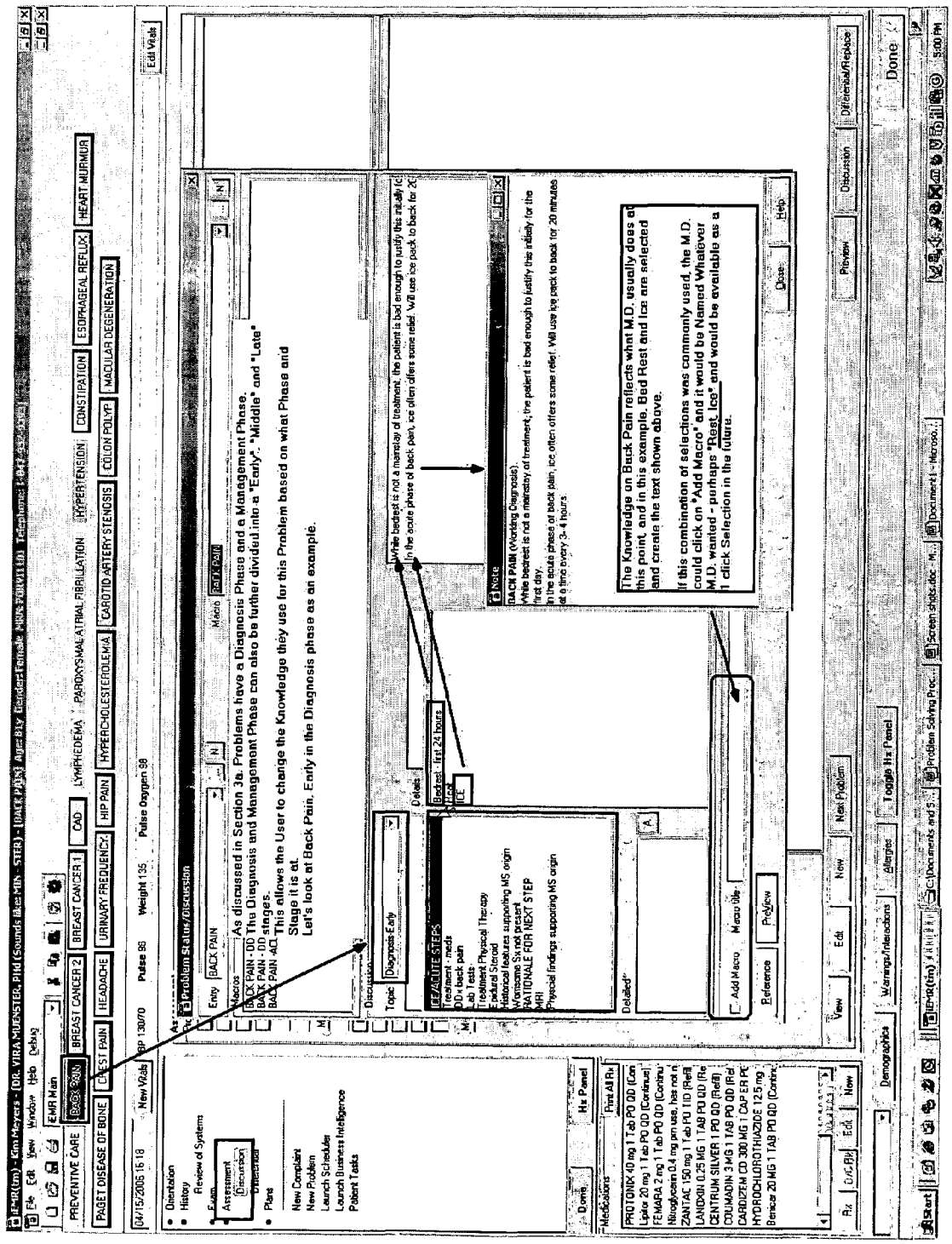

FIG. 25. As discussed, problems have a diagnosis phase and a management phase. The diagnosis and management can also be further divided into a "early.", "middle" and "late" stages. This allows the user to change the knowledge they use for this problem based on what phase and stage it is at. Let's look at back pain, early in the diagnosis phase as an example.

Figure 26:
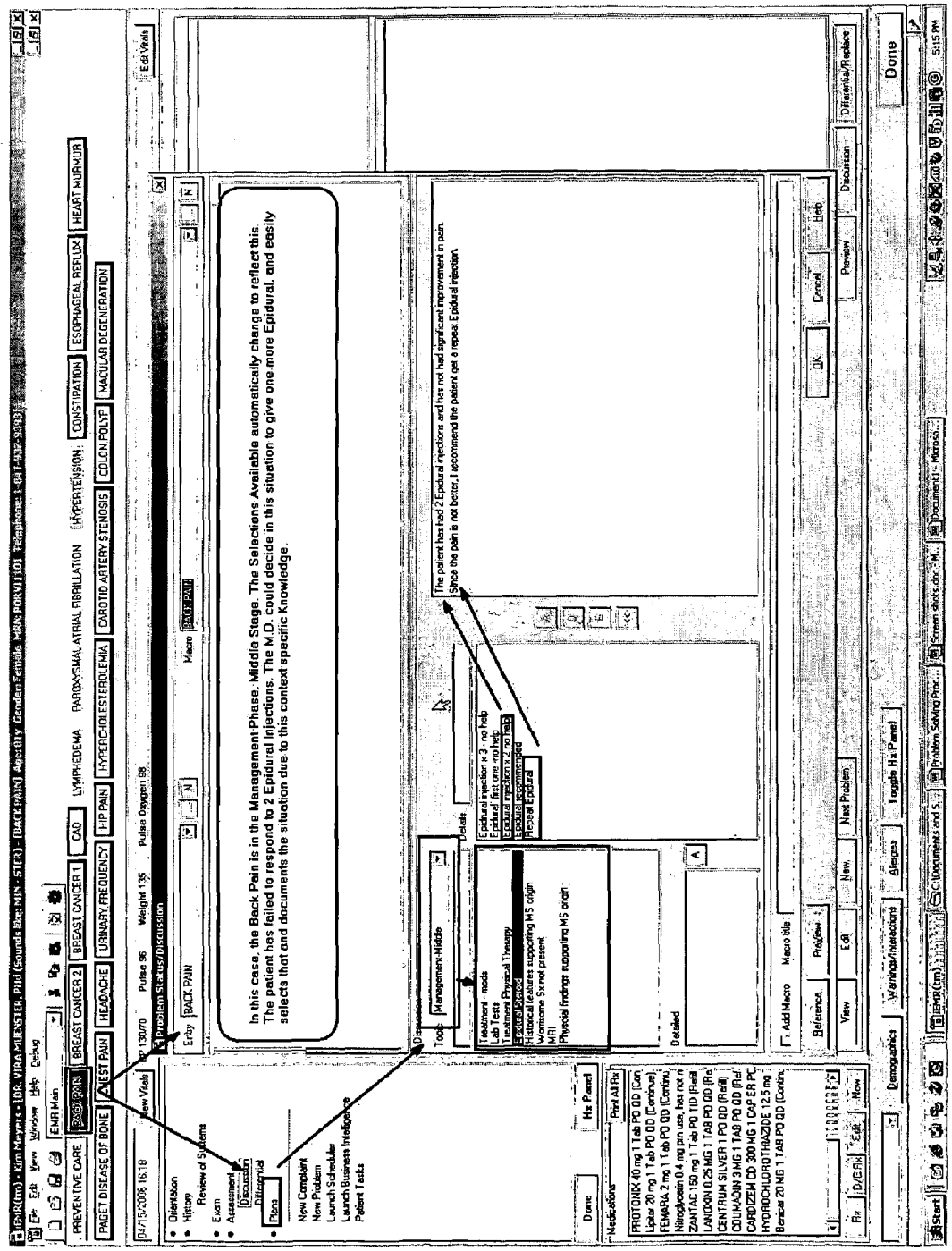

FIG. 26. In this case, the back pain is in the management phase, middle stage. The selections available automatically change to reflect this. The patient has failed to respond to 2 epidural injections. The M.D. Could decide in this situation to give one more epidural, and easily selects that and documents the situation due to this context specific knowledge.

Figure 27:
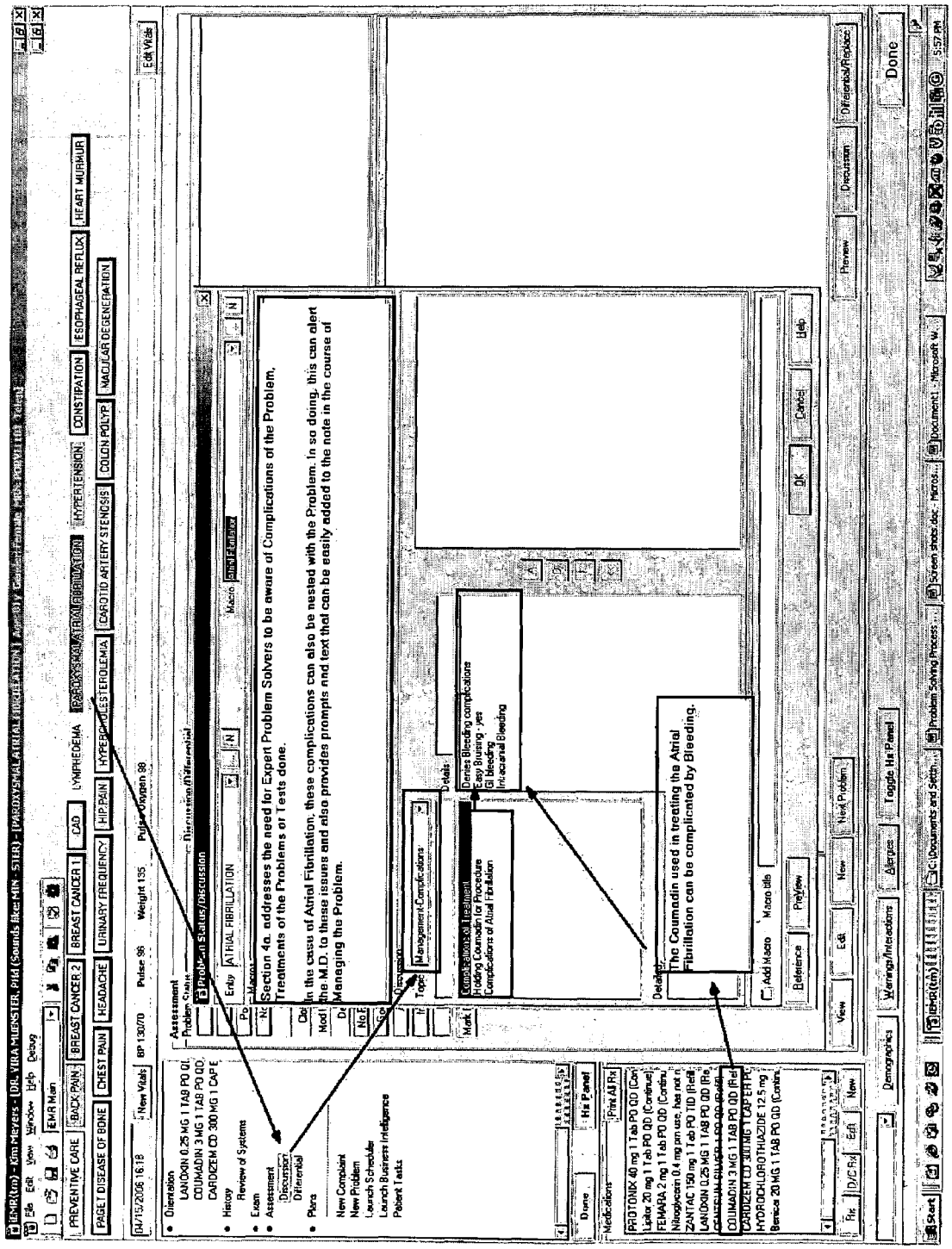

FIG. 27. Addresses the need for expert problem solvers to be aware of complications of the problem. Treatments of the problems or tests done. In the case of atrial fibrillation, these complications can also be nested with the problem. In so doing, this can alert the M.D. To these issues and also provides prompts and text that can be easily added to the note in the course of managing the problem. The coumadin used in treating the atrial fibrillation can be complicated by bleeding.

Figure 28:
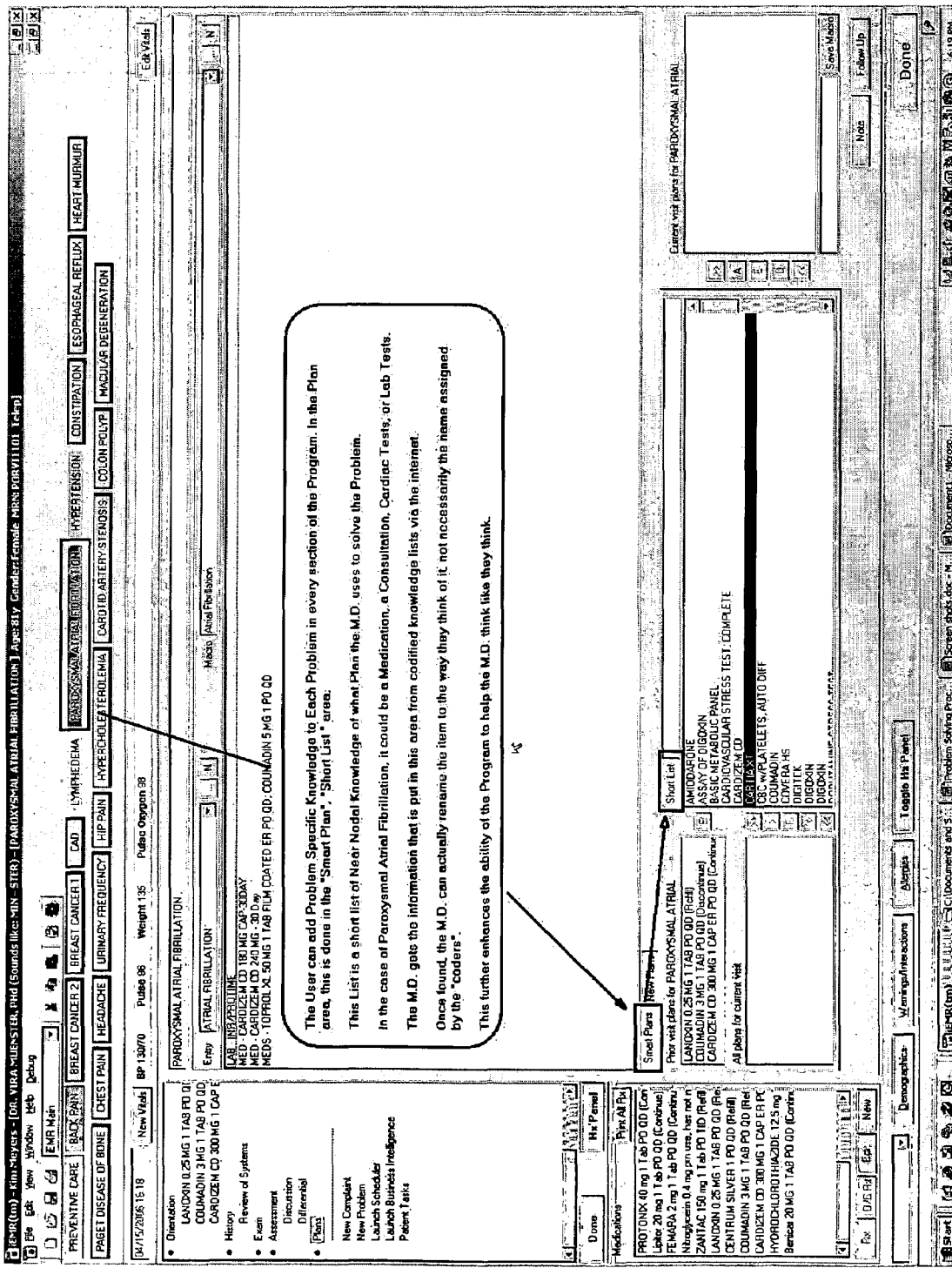

FIG. 28. The user can add problem specific knowledge to each problem in every section of the program. In the plan area, this is done in the "smart plans."/"short list" area. This list is a short list of near nodal knowledge of what plan the M.D. Uses to solve the problem. In the case of paroxysmal atrial fibrillation, it could be a medication, a consultation, cardiac tests, or lab tests. The M.D. Gets the information that is put in this area from codified knowledge lists via the internet. Once found, the M.D. Can actually rename the item to the way they think of it, not necessarily the name assigned by the "coders." This further enhances the ability of the program to help the M.D. Think like they think.

Figure 29:
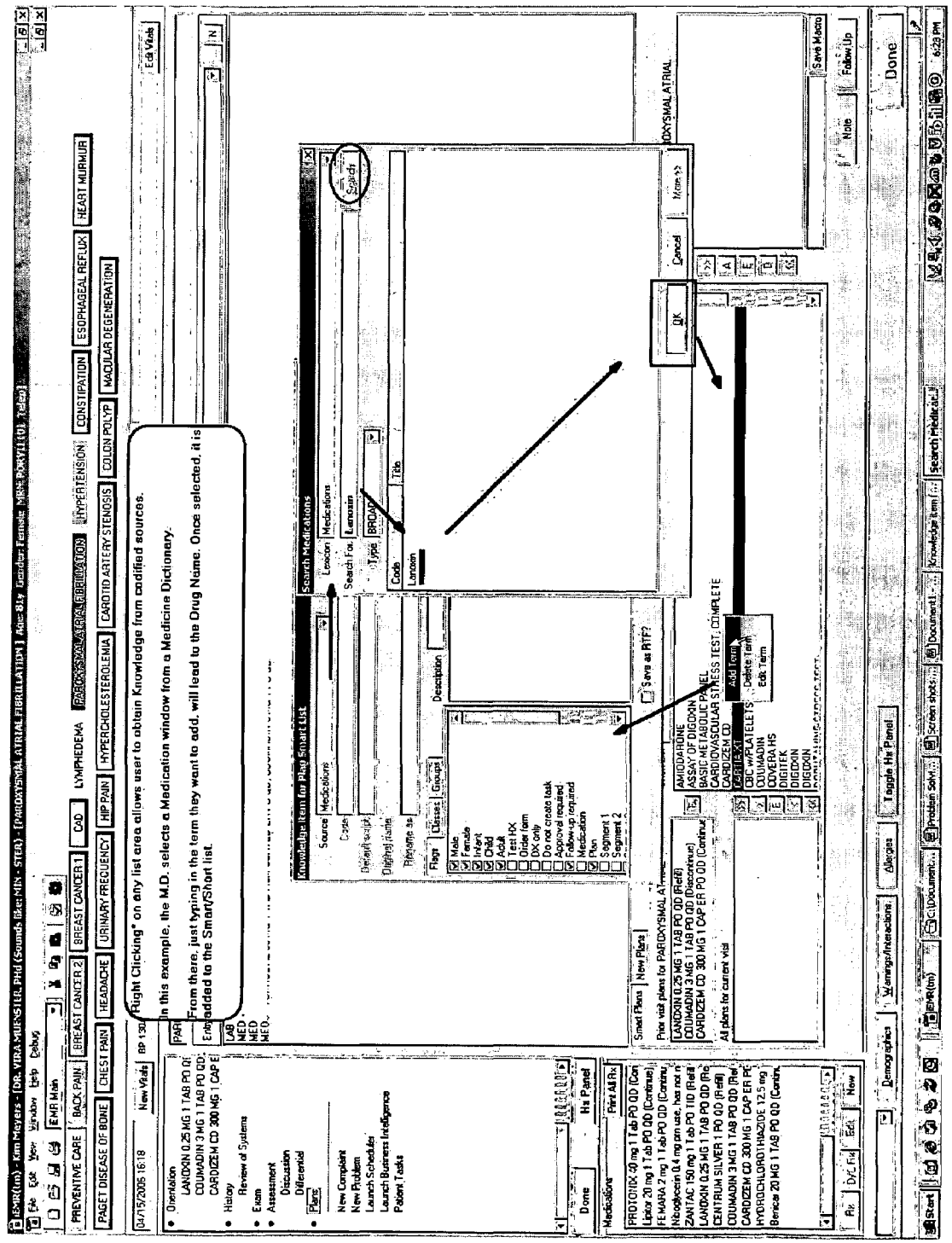

FIG. 29. "right clicking" on any list area allows user to obtain knowledge from codified sources. In this example, the M.D. Selects a medication window from a medicine dictionary. From there, just typing in the term they want to add, will lead to the drug name. Once selected it is added to the smart/short list.

Figure 30:
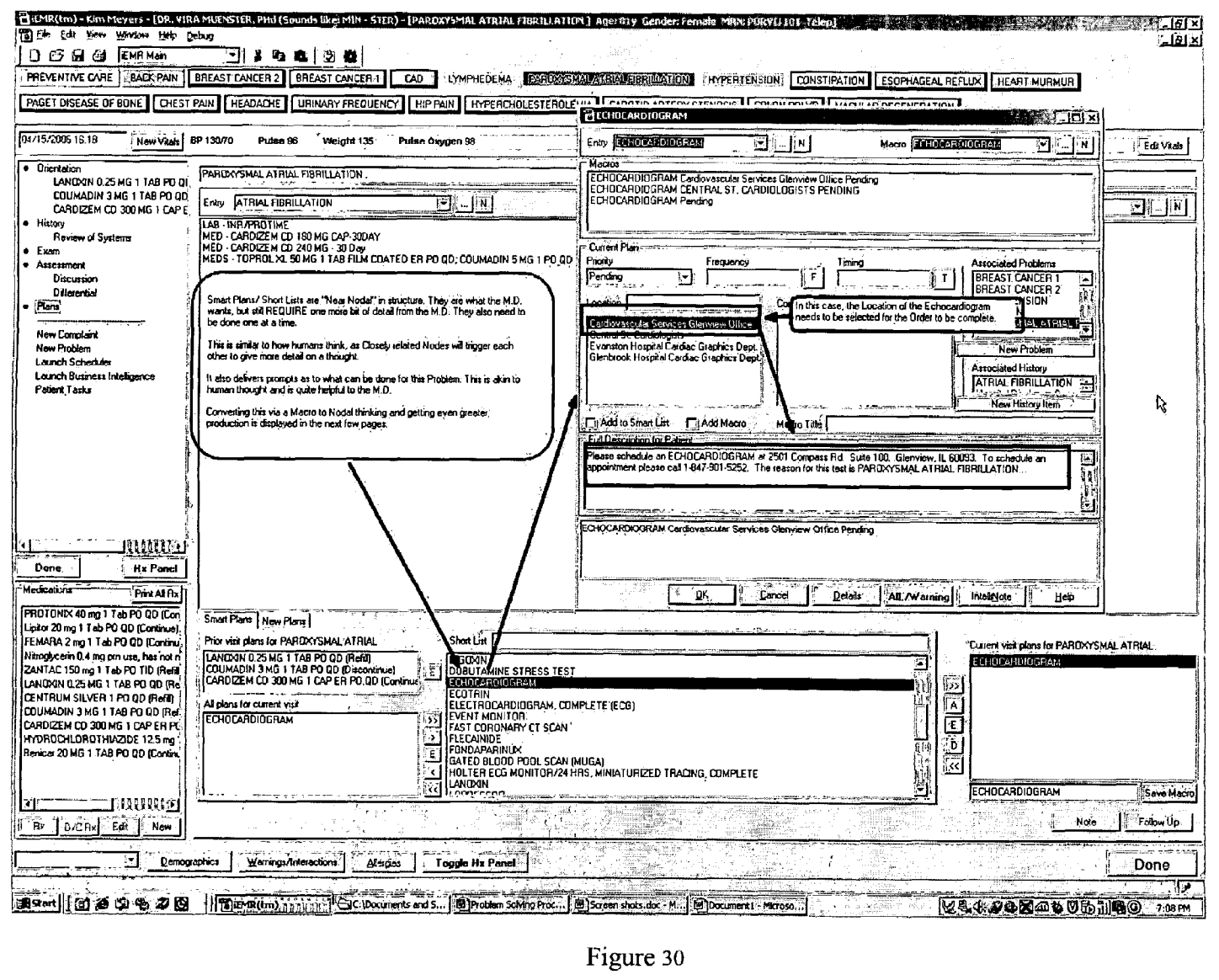

FIG. 30. Smart plans/short lists are "near nodal" in structure. They are what the M.D. Wants, but still require one more bit of detail from the M.D. They also need to be done one at a time. This is similar to how humans think, as closely related nodes will trigger each other to give more detail on a thought. It also delivers prompts as to what can be done for the problem. This is akin to human thought and is quite helpful to the M.D. Converting this via a macro to nodal thinking and getting even greater production is displayed in the next few pages.

Figure 31:
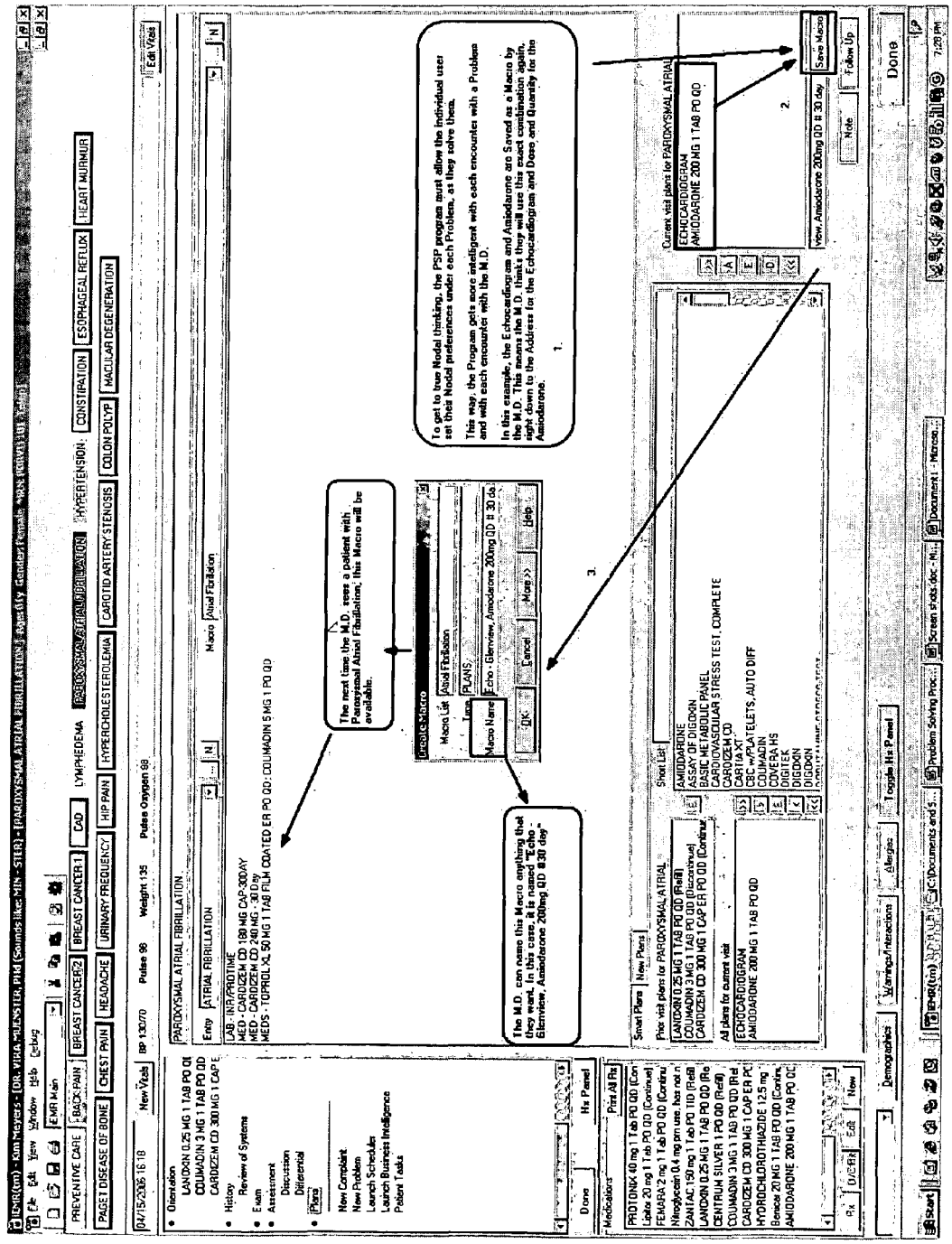

FIG. 31. The next time the M.D. Sees a patient with paroxysmal atrial fibrillation, the macro will be available. The M.D. Can name this macro anything that they want. In this case, it is named "echo glenview amiodarone 200 mg QD #30 day". To get to true nodal thinking, the PSP program must allow the individual user set their nodal preferences under each problem, as they solve them. This way, the program gets more intelligent with each encounter with a problem and with each encounter with the M.D. In this example, the echocardiogram and amiodarone are saved as a macro by the M.D. This means the M.D. Thinks they will use this exact combination again, right down to the address for the echocardiogram and dose and quantity for the amiodarone.

Figure 32:
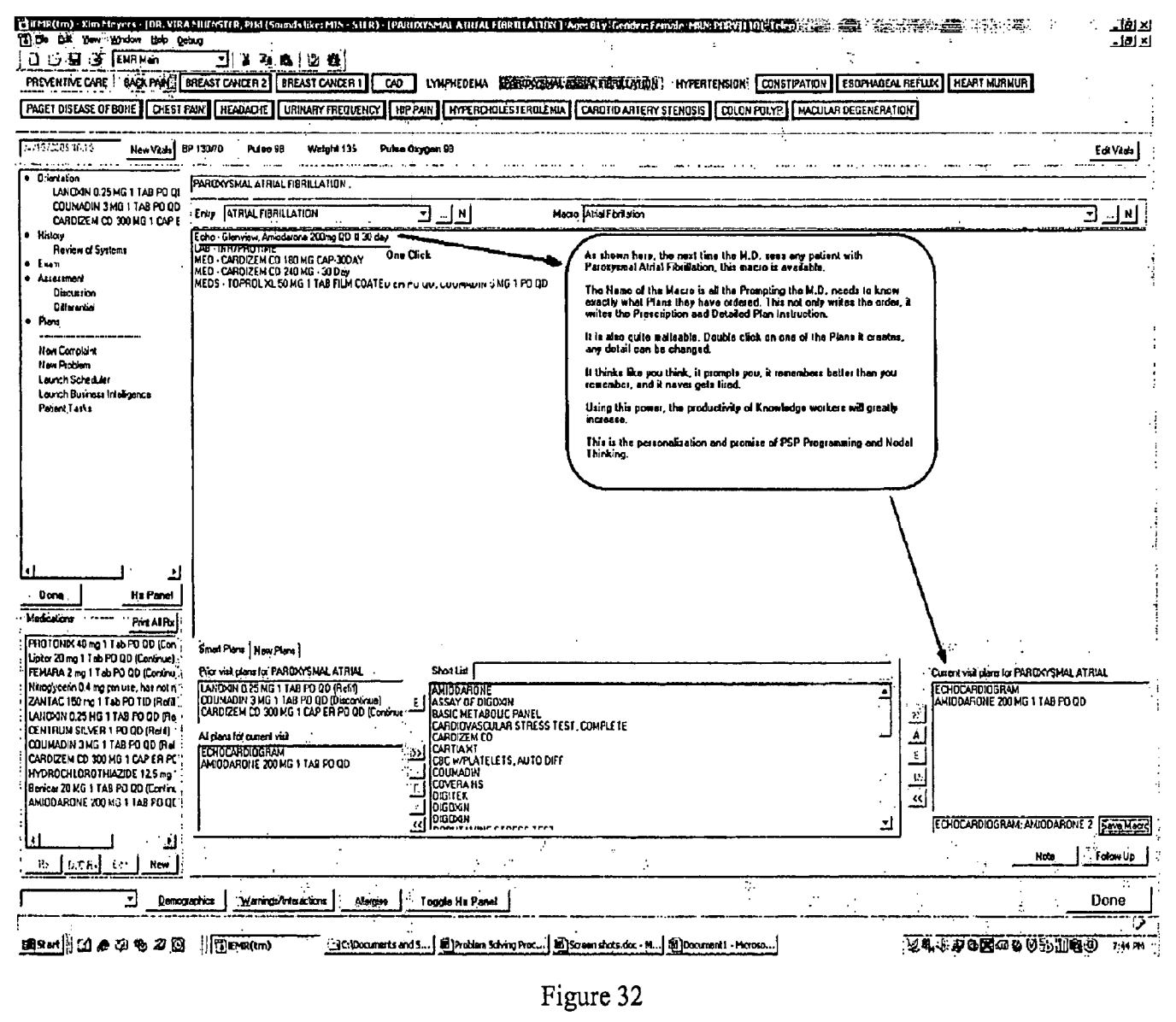

FIG. 32. As shown here, the next time the M.D. Sees any patient with paroxysmal atrial fibrillation, this macro is available. The name of the macro is all the prompting the M.D. Needs to know exactly what plans they have ordered. This not only writes the order, it writes the prescription and detailed plan instruction. It is also quite malleable. Double click on one of the plans it creates, any detail can be changed. Using this power, the productivity of knowledge workers will greatly increase. This is the personalization and promise of PSP programming and nodal thinking.

Figure 33:
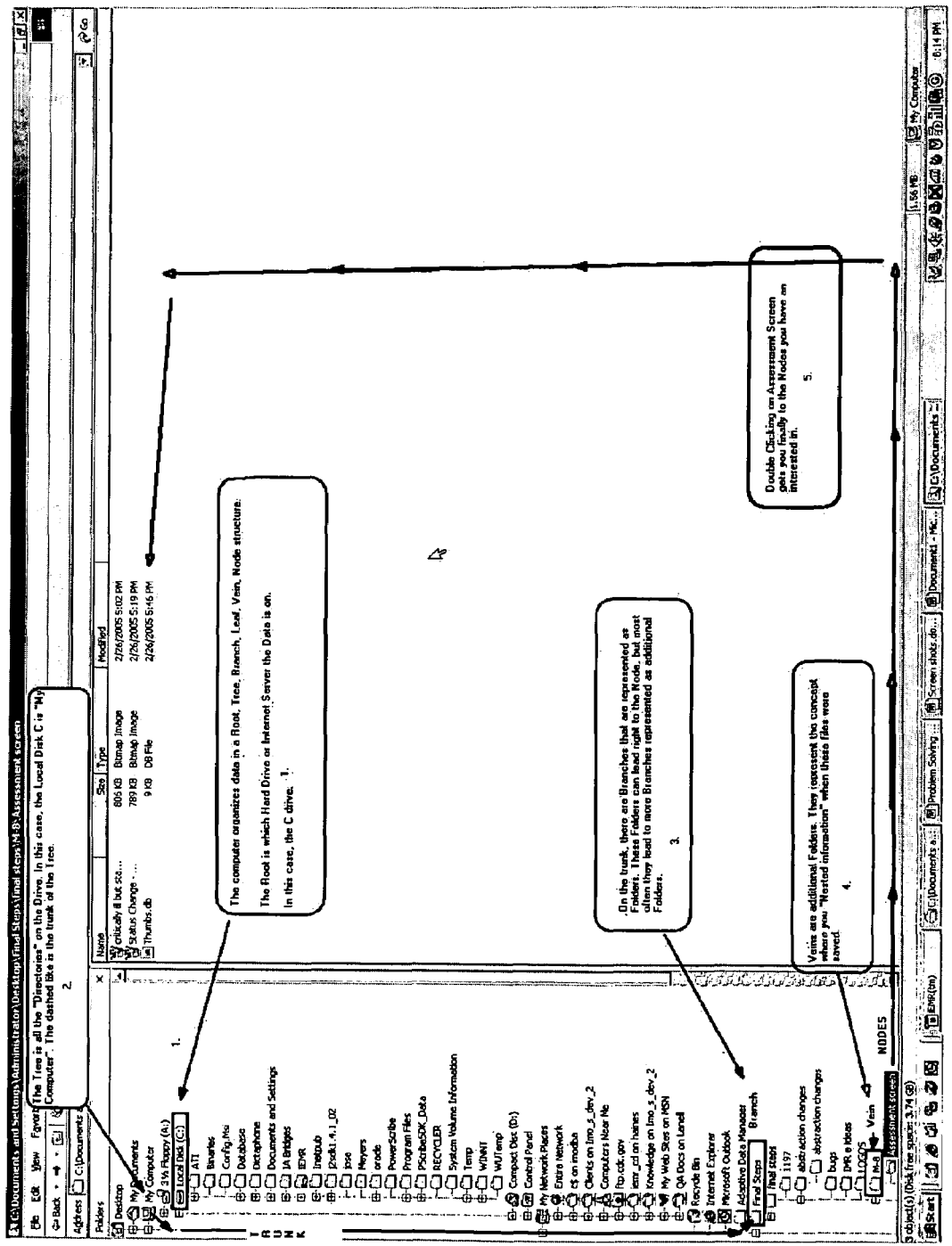

FIG. 33. The computer organizes data in a root, tree, branch, leaf, vein, nodal structure. The root is which hard drive or internet server the data is on. In this case, the c drive (1). The tree is all the "directories" on the drive. In this case, the local disk c is my computer". The dashed like is the trunk of the tree (2). On the trunk, there are branches that are represented as folders. These folders can lead right to the node, but most often they lead to more branches represented as additional folders (3). Veins are additional folders. They represent the concept when you "nested information" when these files were saved (4). Double clicking on assessment screen gets you finally to the nodes you have an interest in (5).

Figure 34:
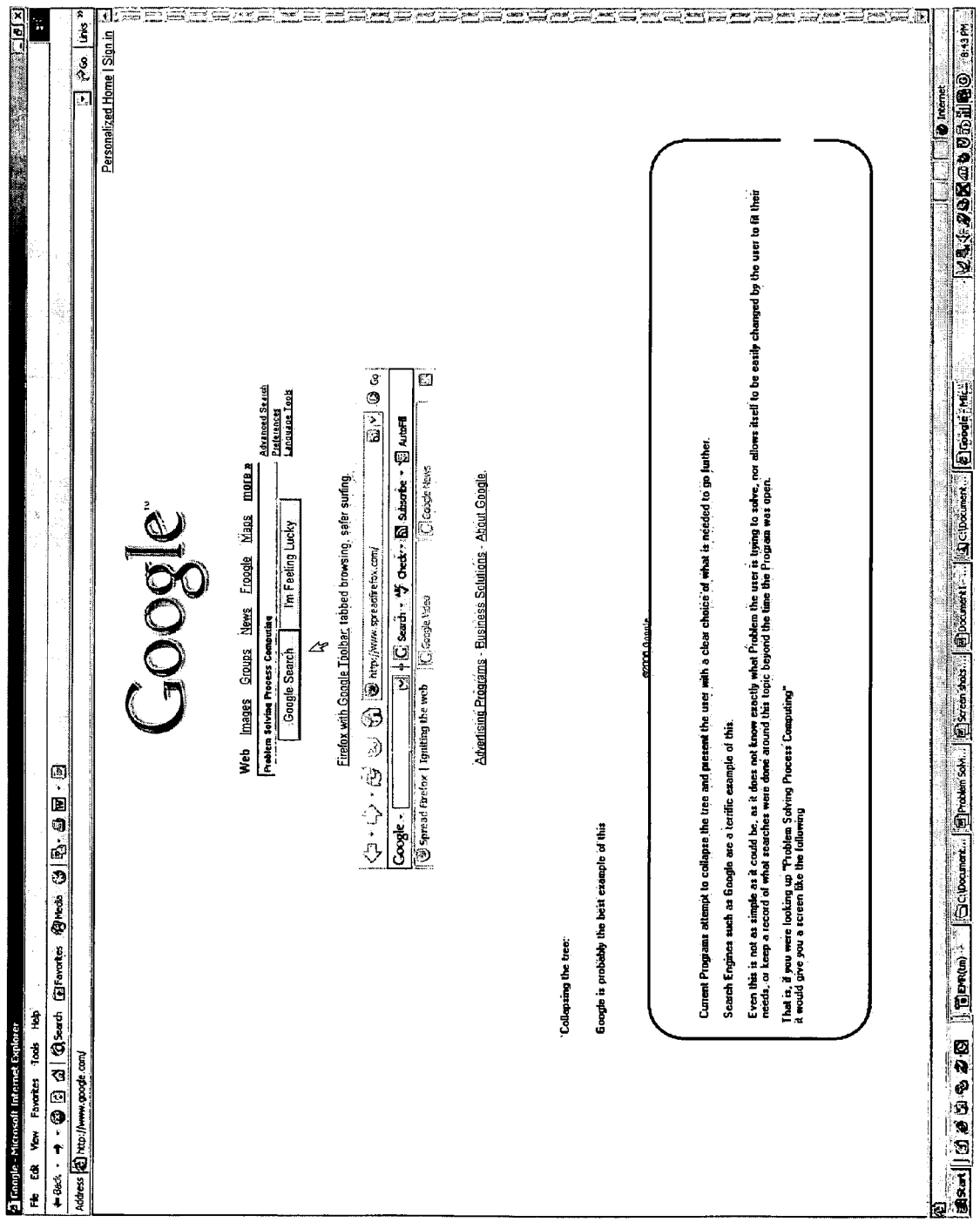

FIG. 34. Current programs attempt to collapse the tree and present the user with a clear choice of what is needed to go further. Search engines such as google are a terrific example of this. Even this is not as simple as it could be, as it does not know exactly what problem the user is trying to solve, nor allows itself to be easily changed by the user to fit their needs, or keep a record of what searches were done around this topic beyond the time the program was open. That is, if you were looking up "problem solving process computing" it would give you a screen like the following.

Figure 35:
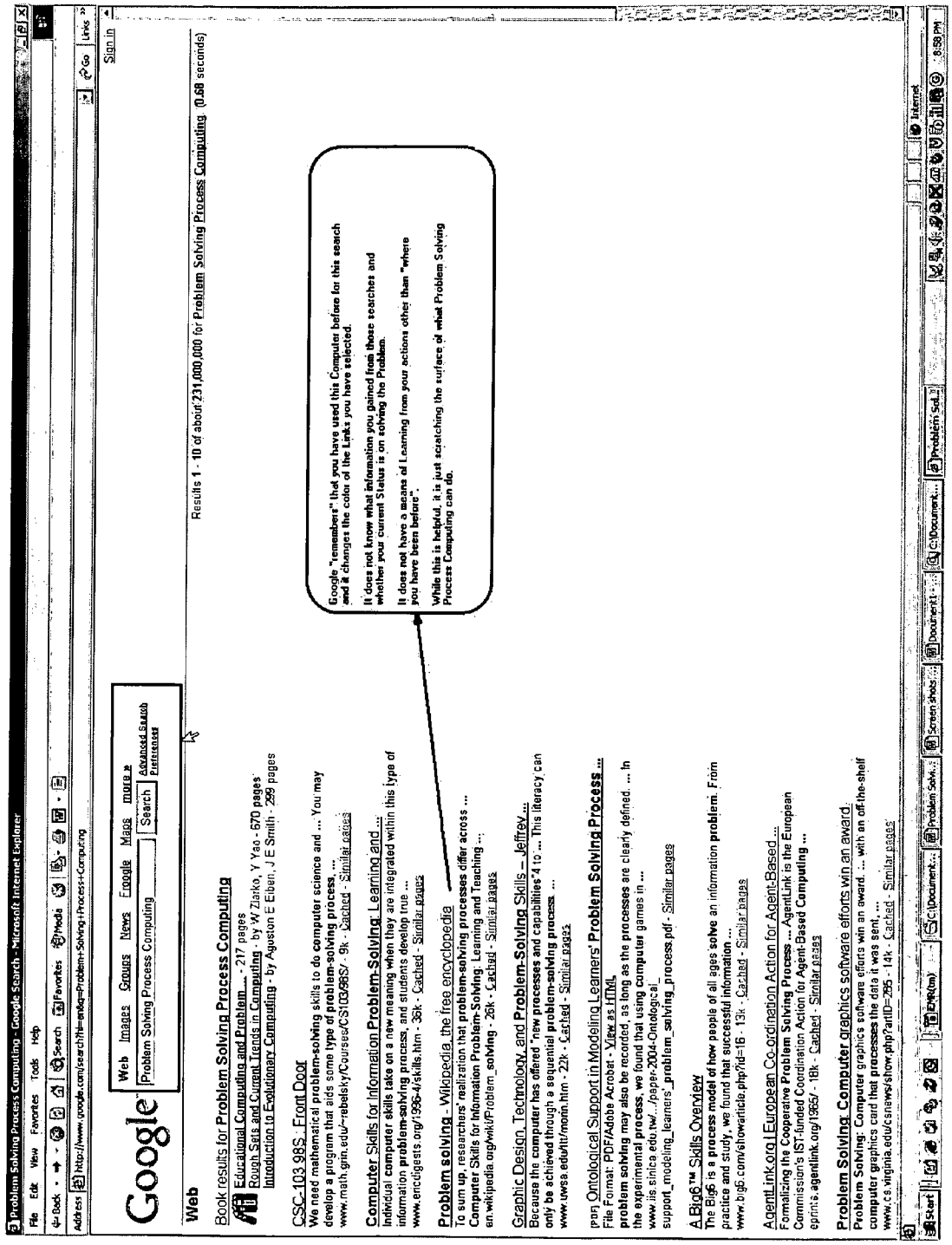

FIG. 35. Google "remembers" that you have used this computer before for this search and it changes the color of the links you have selected. It does not know what information you gained from these searches and whether your current status is on solving the problem. It does not have a means of learning how your actions other than "where you have been before". While this is helpful, it is just scratching the surface of what problem solving process computing can do.

Figure 36:
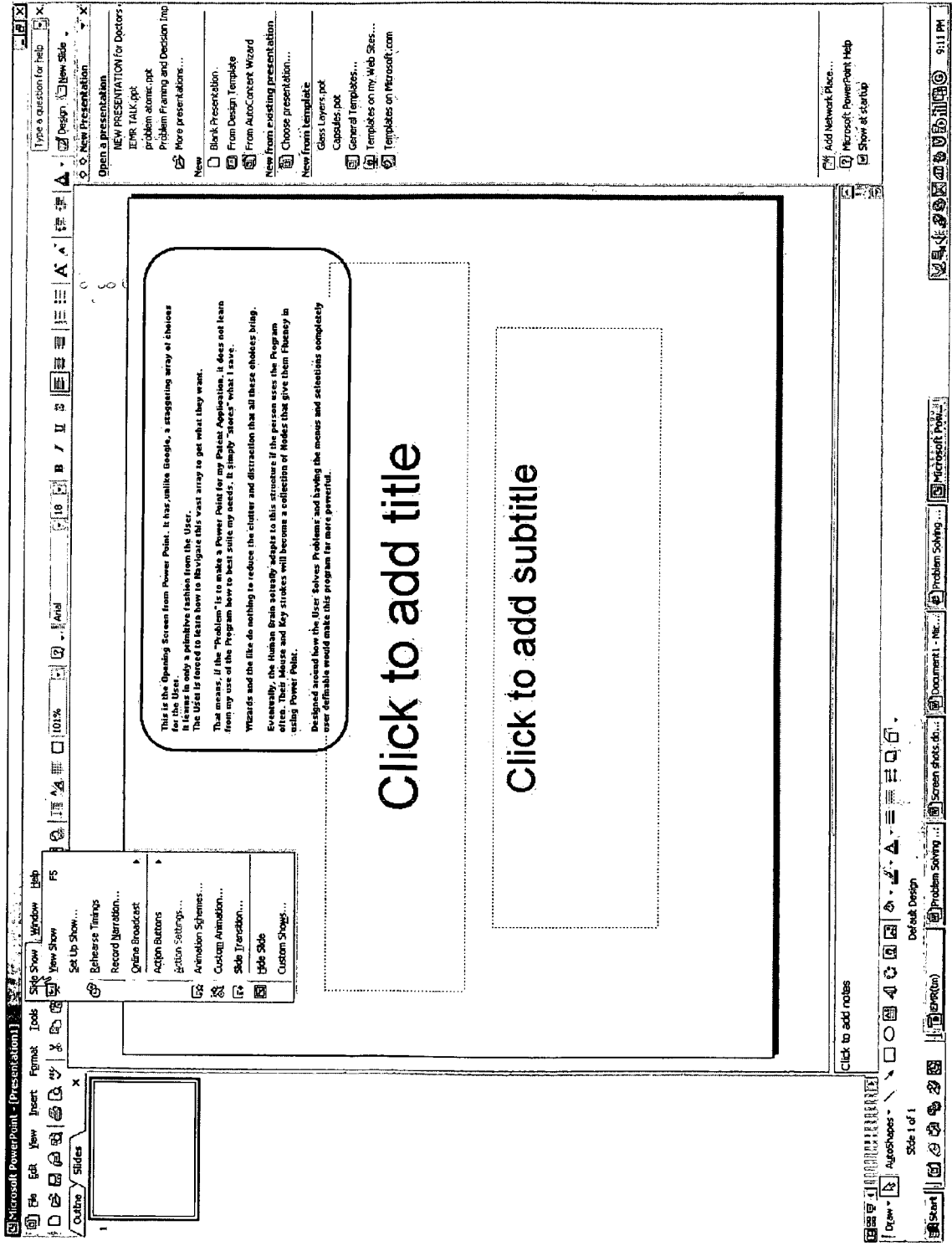

FIG. 36. This is the opening screen from power point. It has, unlike Google, a staggering array of choices for the user. It learns in only a primitive fashion from the user. The user is forced to learn how to navigate this vast array to get what they want. That means, if the "problem" is to make a power point for my patent application, it does not learn from my use of the program how to best suit my needs. It simply "stores" what I save. Wizards and the like do nothing to reduce the clutter and distraction that all these choices bring. Eventually, the human brain actually adapts to this structure if the person uses the program often. Their mouse and key strokes will become a collection of nodes that give them fluency in using power point. Designed around how the user solves problems and having the means and selections completely user definable would make this program far more powerful.

Figure 37:
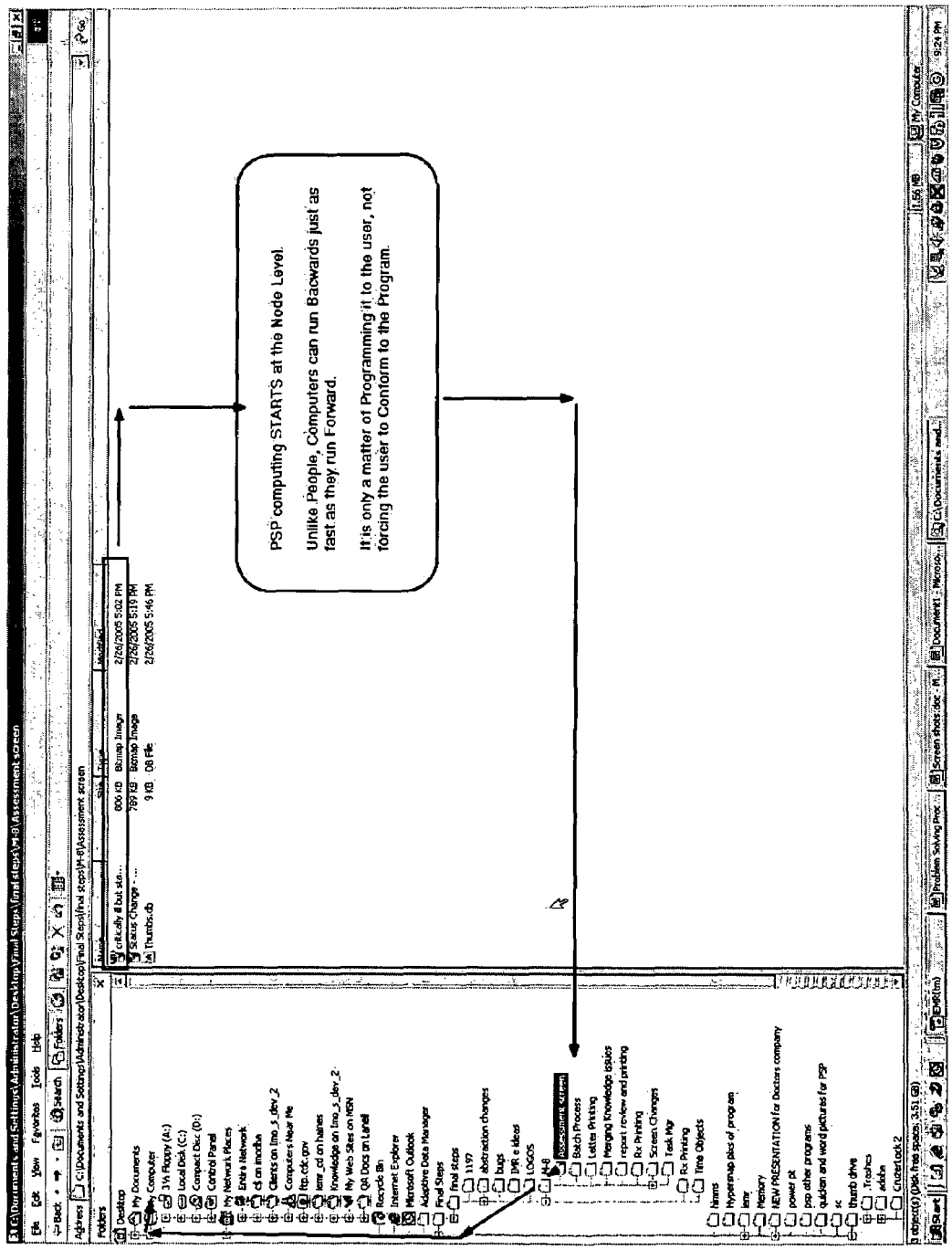

FIG. 37. PSP computing starts at the node level. Unlike people, computers can run backwards just as fast as they can run forward. It is only a matter of programming it to the user, not forcing the user to conform to the program.

Figure 38:
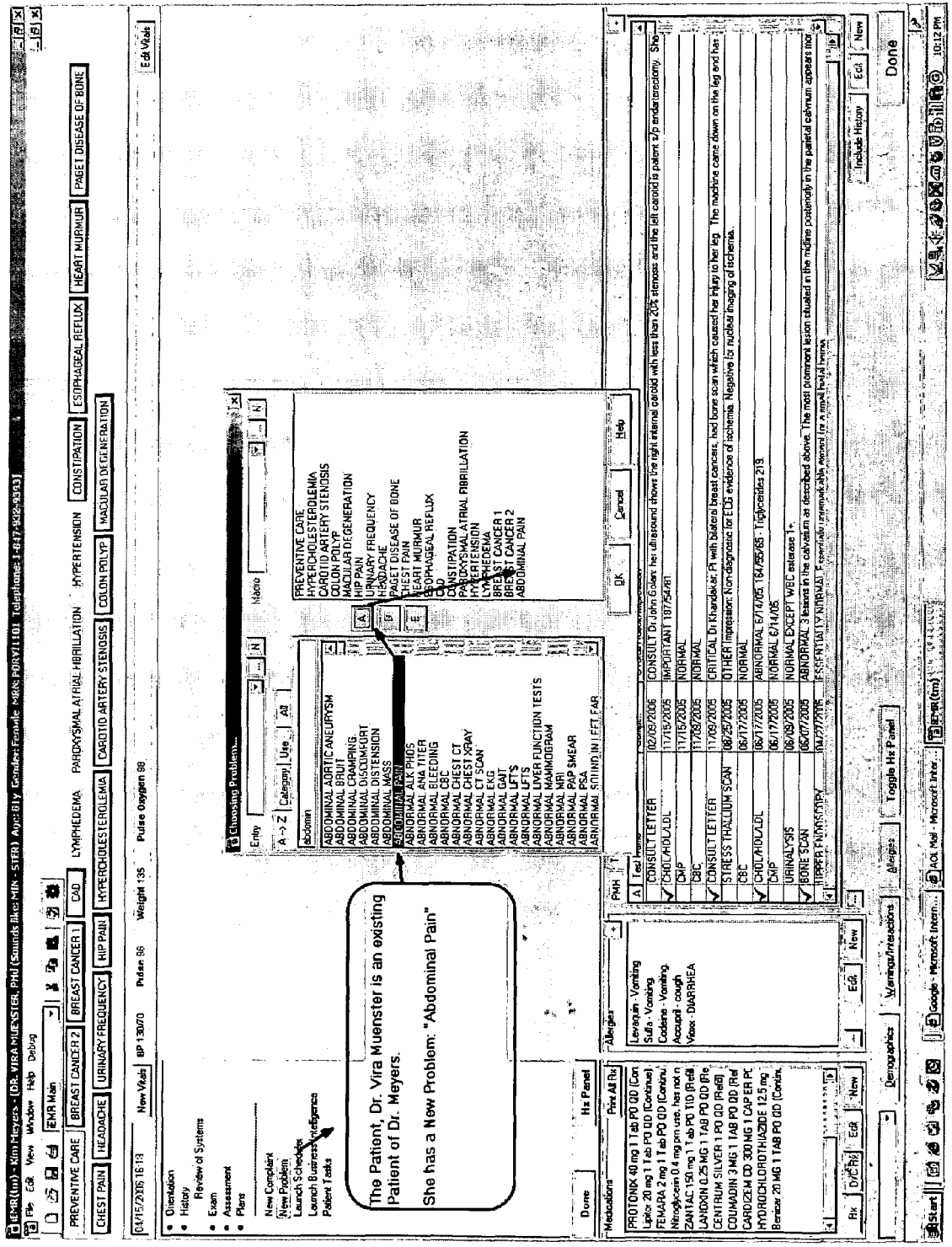

FIG. 38. The patient, Vira Muenster is an existing patient of Dr. Meyers. She has a new problem, "abdominal pain".

Figure 39:
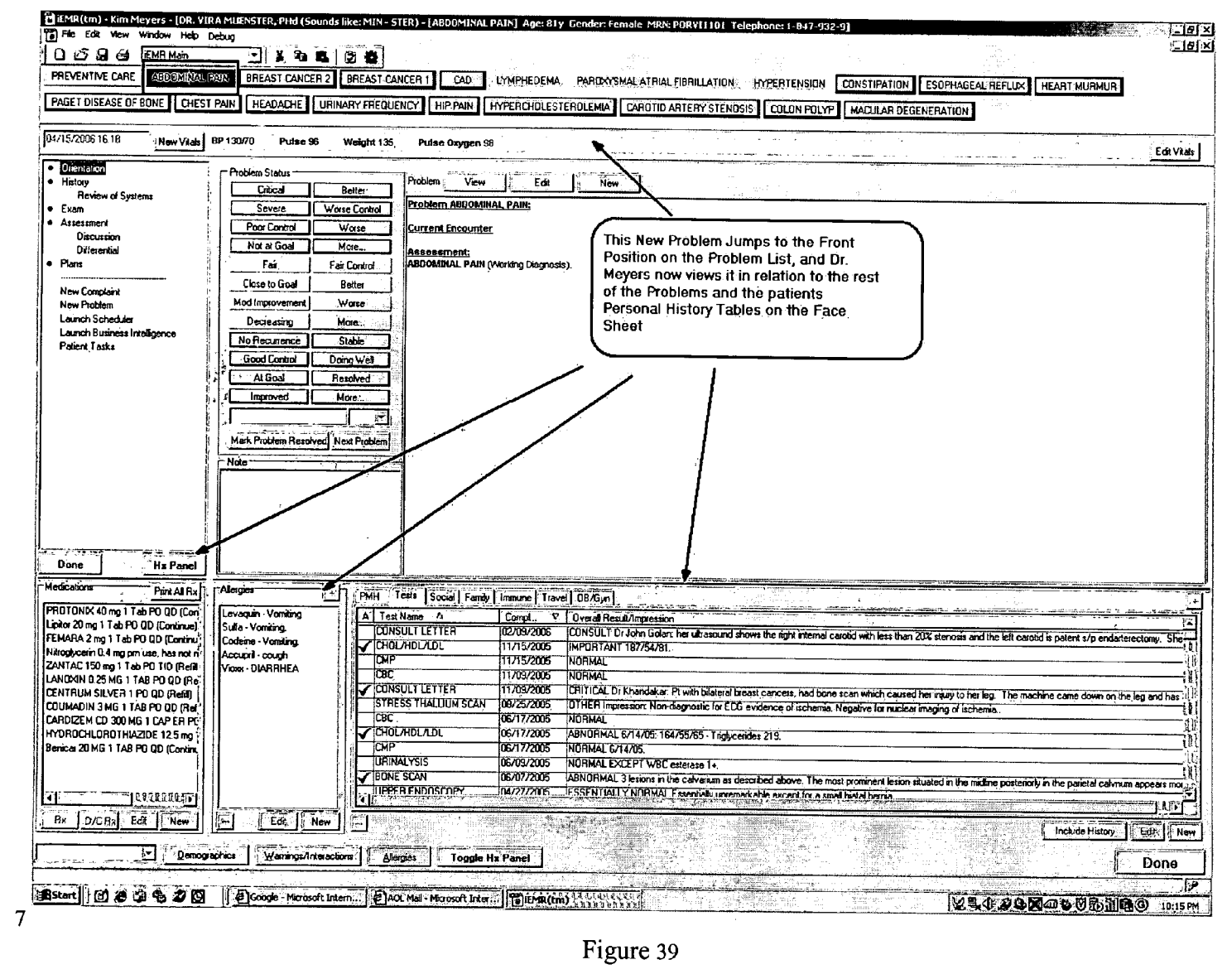

FIG. 39. The new problem jumps to the front position on the problem list, and Dr. Meyers now views it in relation to the rest of the problems and the patients personal history tables on the face sheet.

Figure 40:
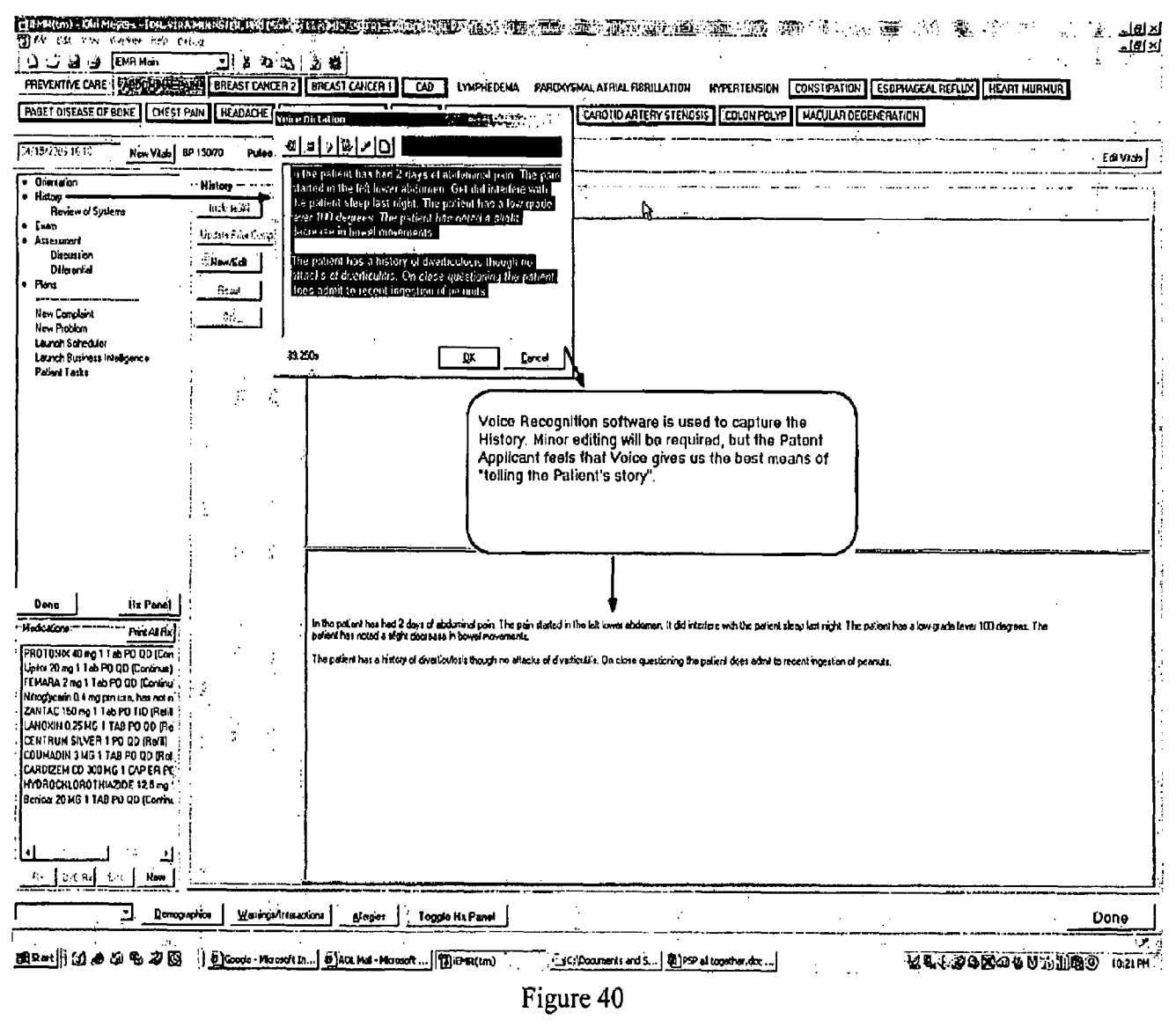

FIG. 40. Voice recognition software is used to capture the history. Minor editing will be required, but the patent applicant feels that voice gives us the best means of "telling the patient's story".

Figure 41:
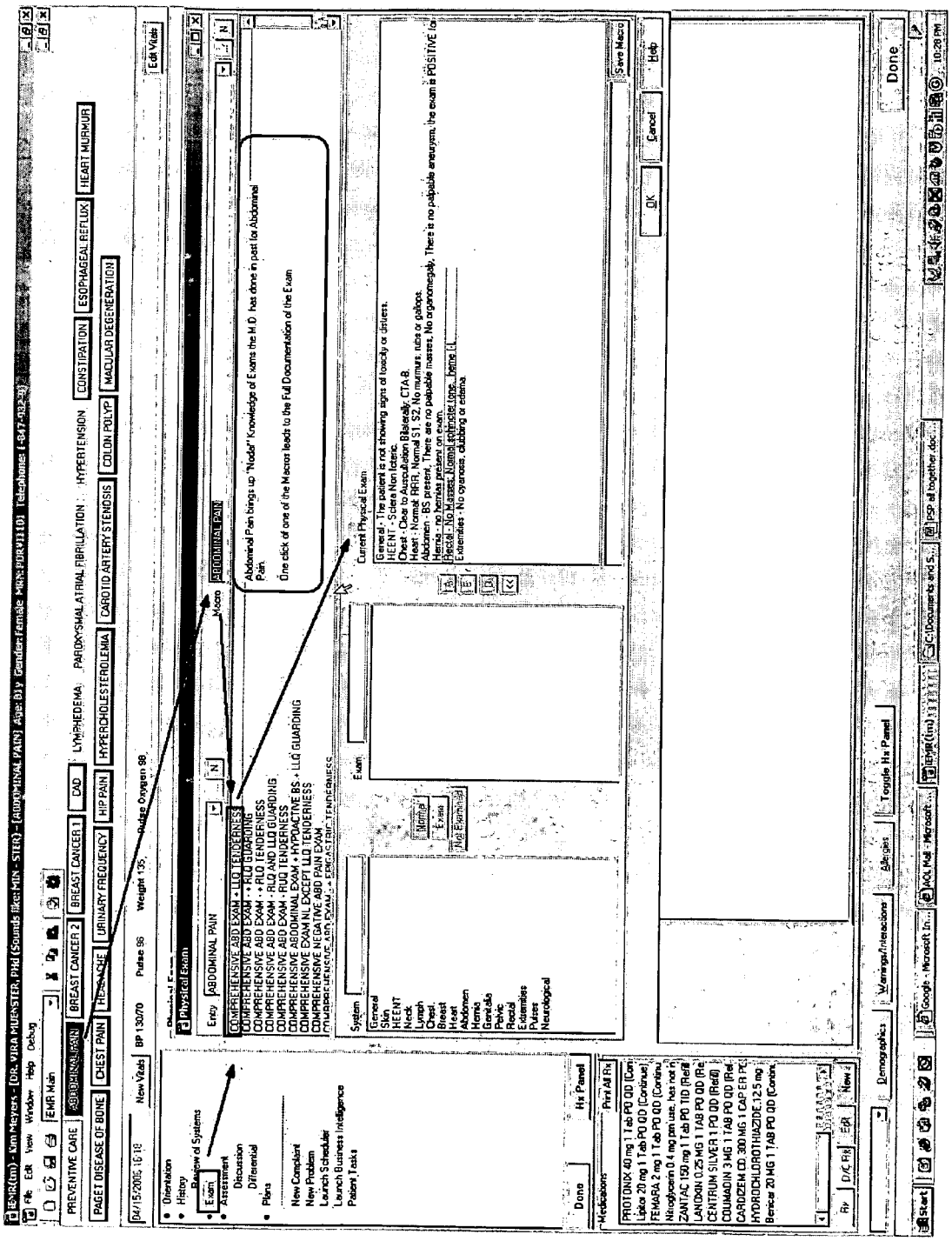

FIG. 41. Abdominal pain brings up "nodal" knowledge of exams the M.D. Has done in past for abdominal pain. One click of one of the macros leads to the full documentation of the exam.

Figure 42:
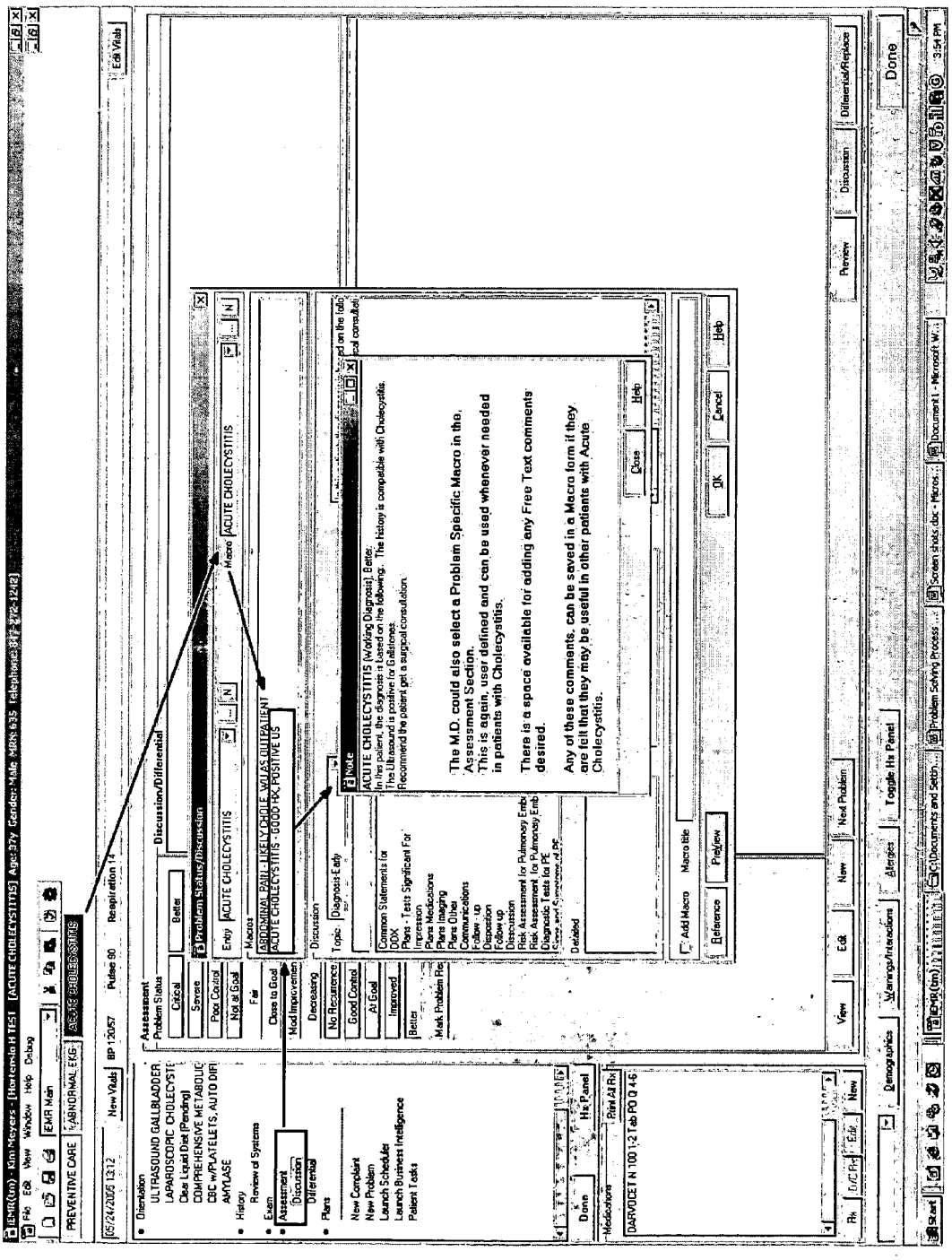

FIG. 42. The M.D. could also select a problem specific macro in the assessment section. This is again user defined and can be used whenever needed in patients with cholecystitis. There is a space available for adding any free text comments desired. Any of these comments, can be saved in a macro form if they are felt that they may be useful in other patients with acute cholecystitis.

Figure 43:
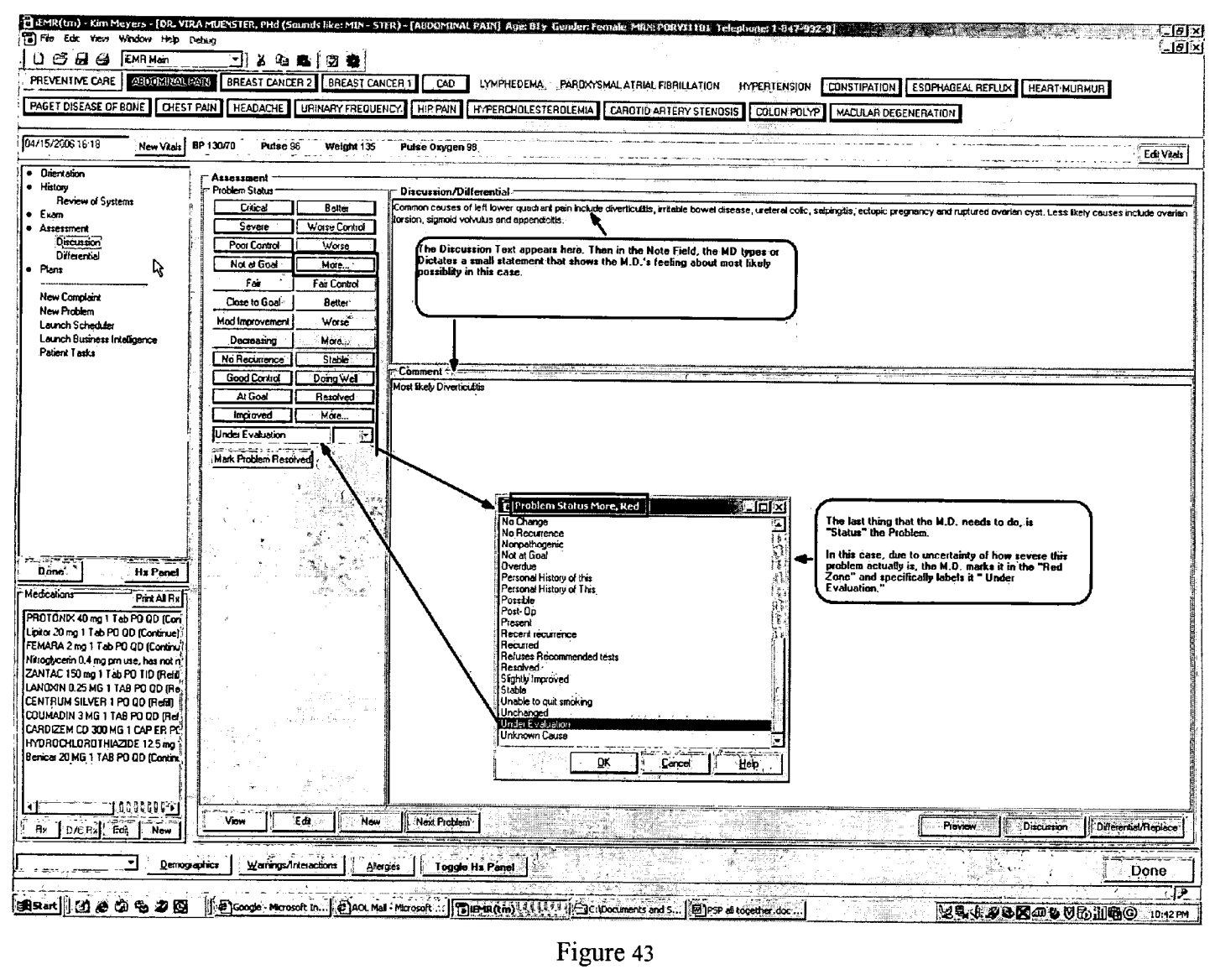

FIG. 43. The discussion text appears here. Then in the note field, the M.D. Types or dictates a small statement that shows the M.D.'s feeling about most likely possibility in this case. The last thing that the M.D. Needs to do is "status" the problem. In this case, due to uncertainty of how severe this problem actually is, the M.D. Marks it in the "red zone" and specifically labels it "under evaluation."

Figure 44:
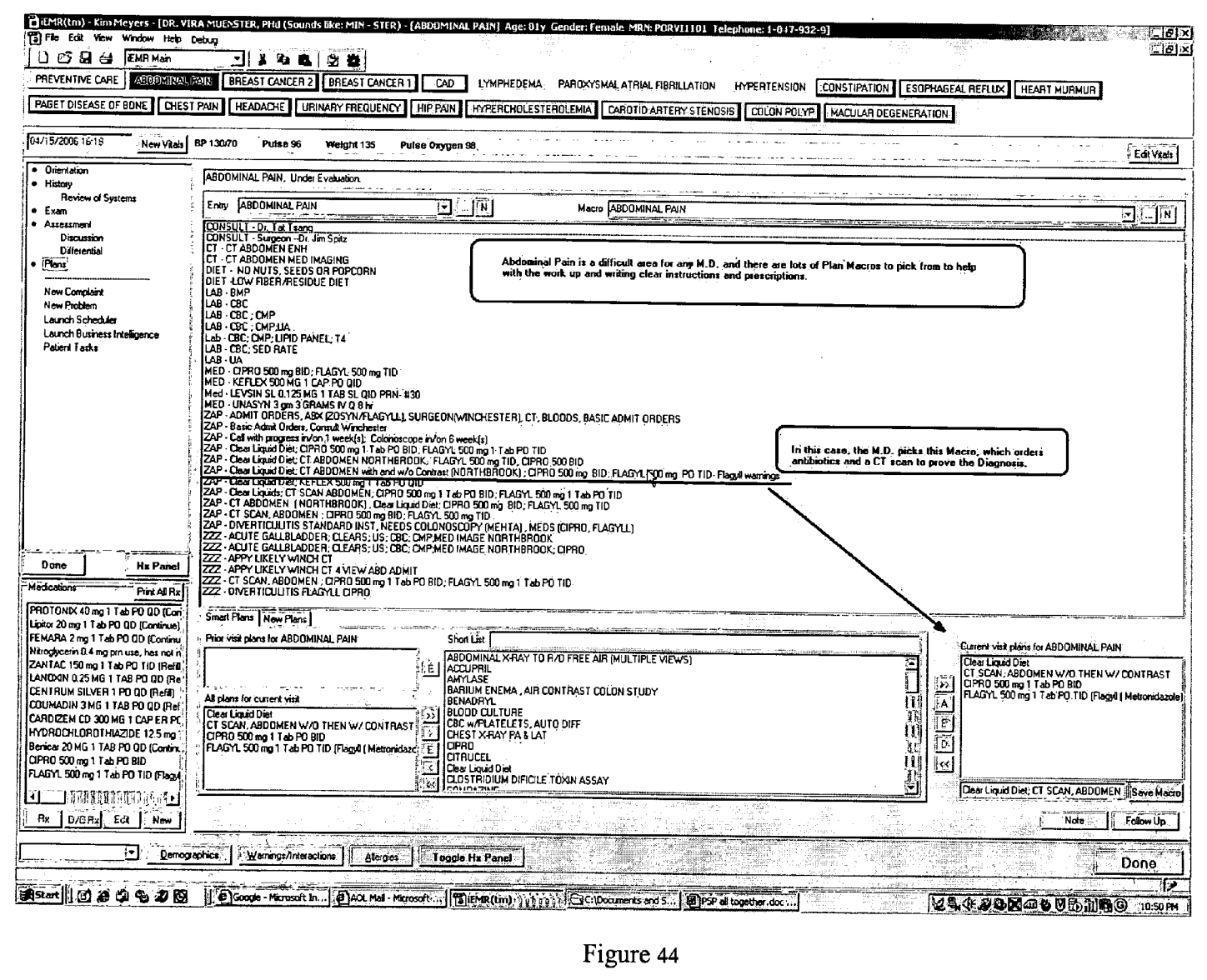

FIG. 44. Abdominal pain is a difficult area for any M.D. and there are several plan macros to pick from to help with the work up and writing clear instructions and prescriptions. In this case, the M.D. picks this macro, which orders antibiotics and a ct scan to prove the diagnosis.

Figure 45:
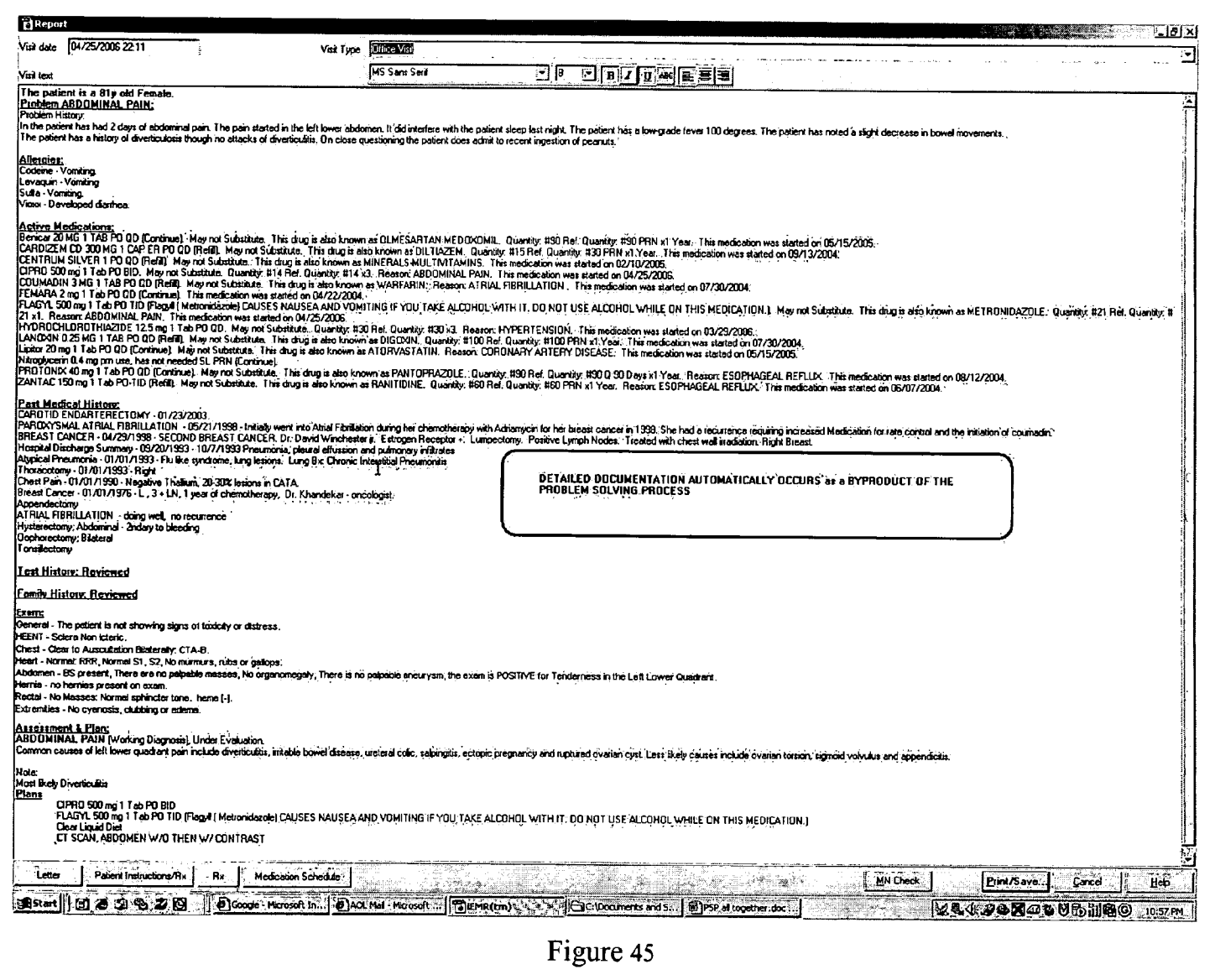

FIG. 45. Detailed documentation automatically occurs as a byproduct of the problem solving process.

Figure 46:
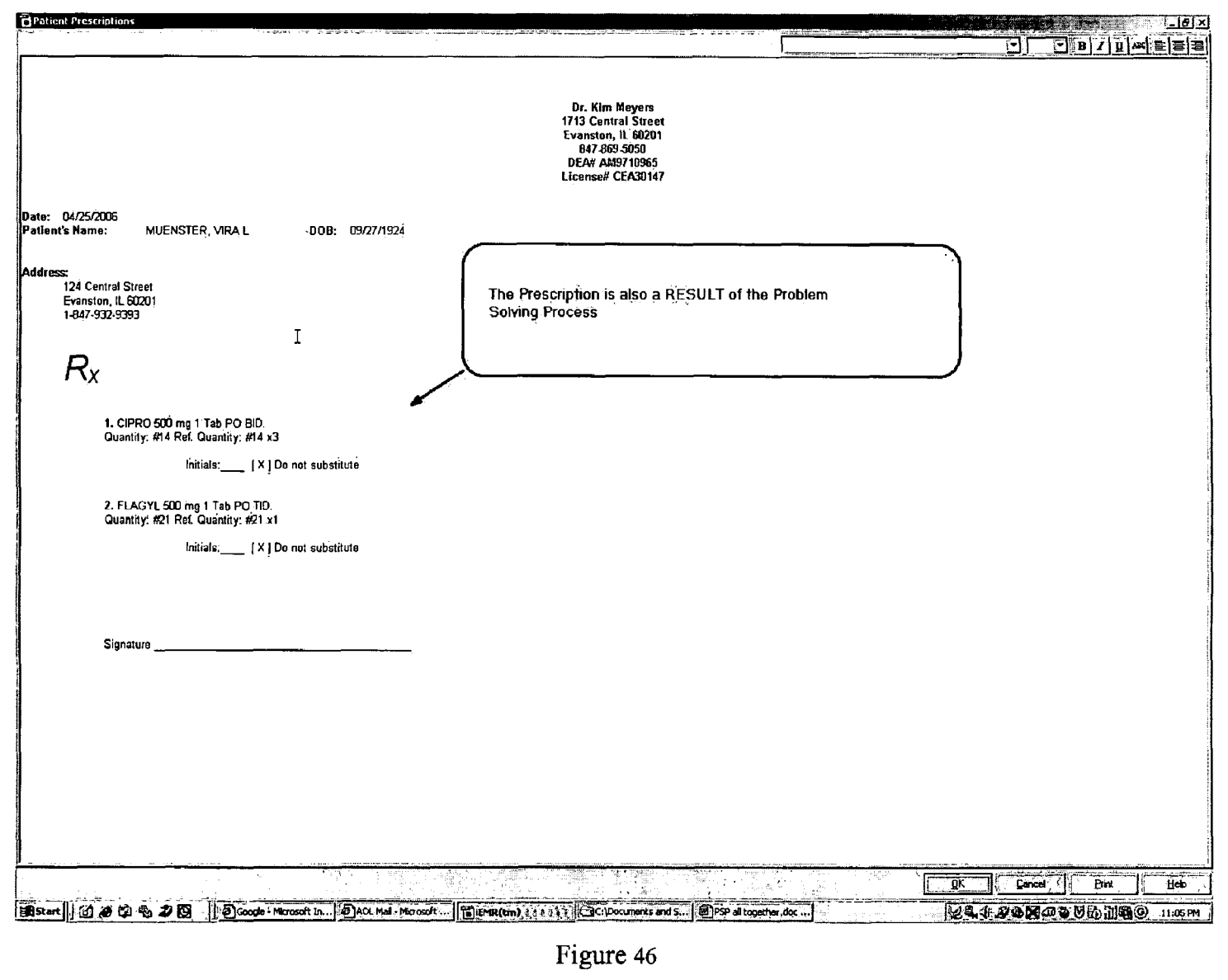

FIG. 46. The prescription is also a result of the problem solving process.

Figure 47:
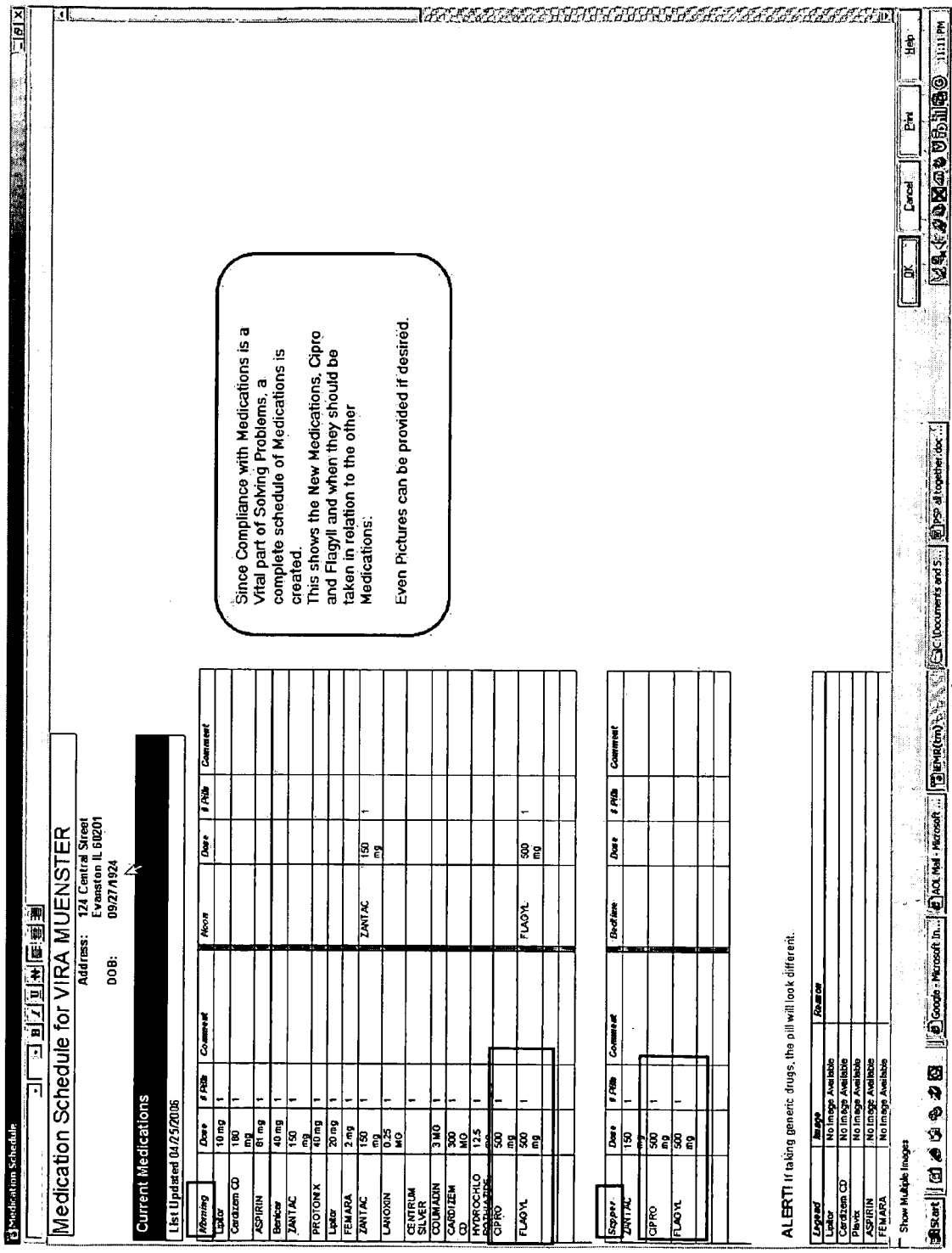

FIG. 47. Since compliance with medications is a vital part of solving problems, a complete schedule of medications is created. This shows the new medications, cipro and flagyll and when they should be taken in relation to the other medications. Even pictures can be provided if desired.

Figure 48:
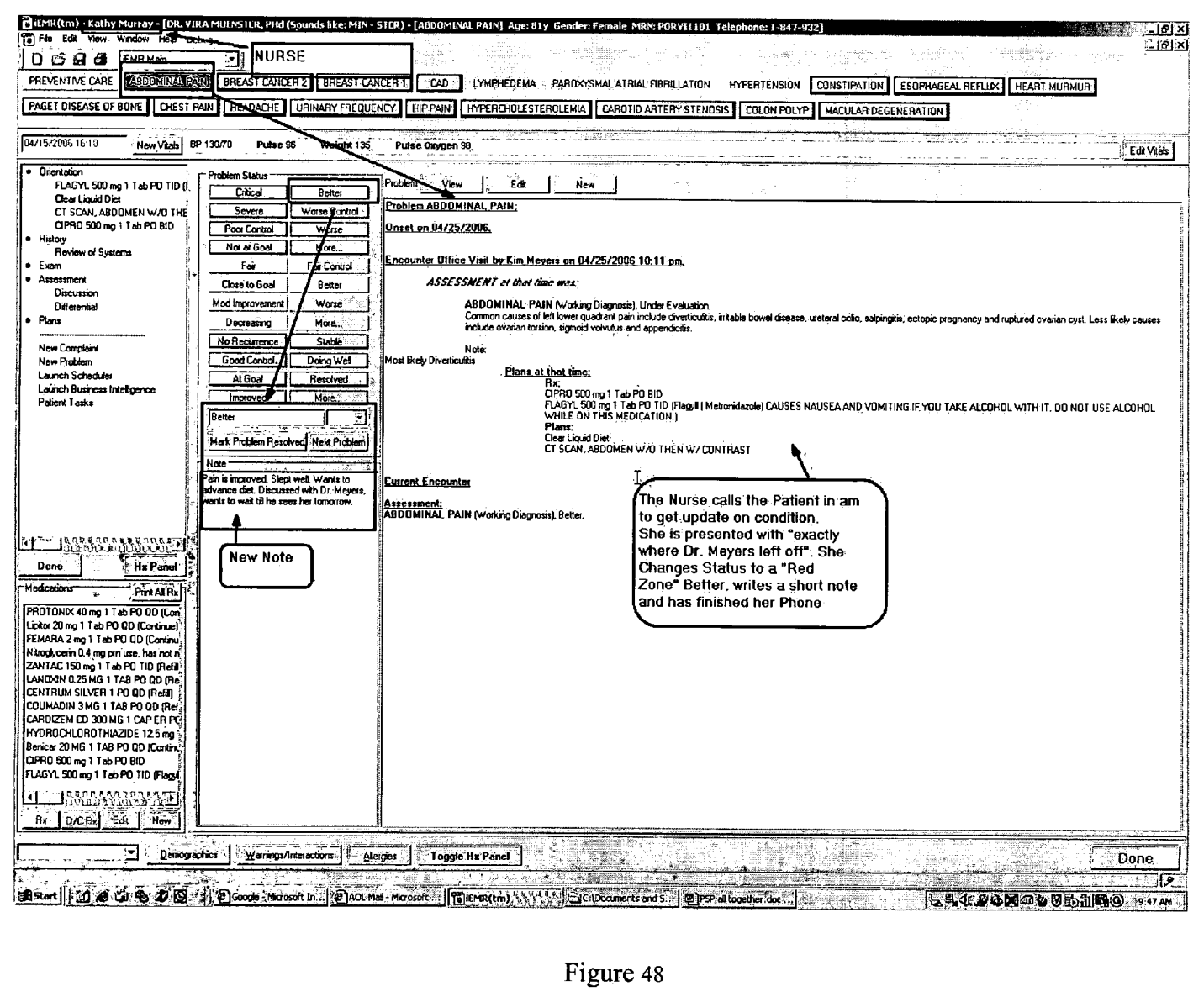

FIG. 48. The nurse calls the patient in a.m. to get update on condition. She is presented with "exactly where Dr. Meyers left off". She changes status to a "red zone" better, writes a short note and has finished her phone call.

Figure 49:
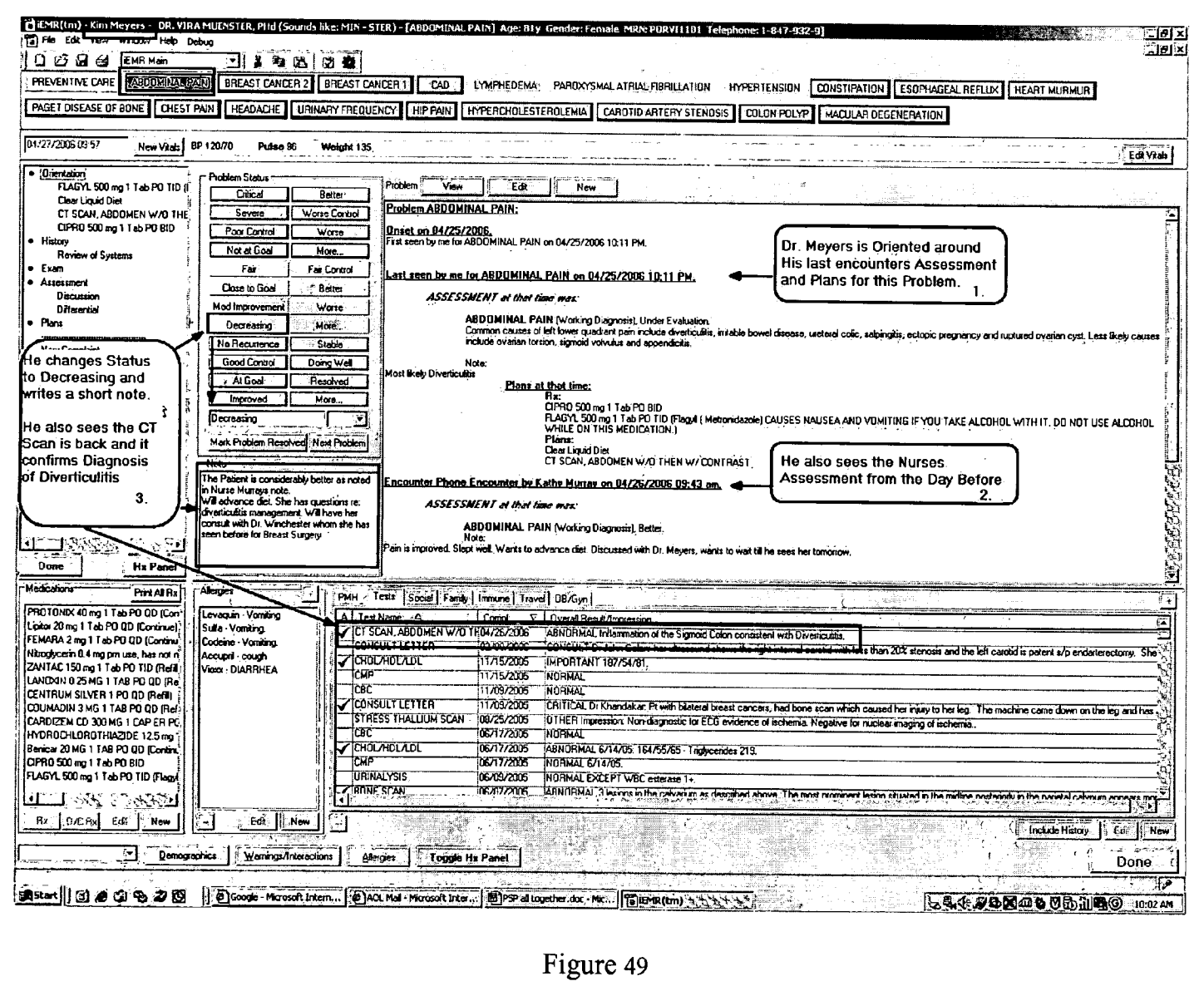

FIG. 49. Dr. Meyers is oriented around his last encounters assessment and plans for this problem (1). He also sees the nurses assessment for the day before (2). He changes status to decreasing and writes a short note. He also sees the ct scan is back and it confirms diagnosis of diverticulitis (3).

Figure 50:
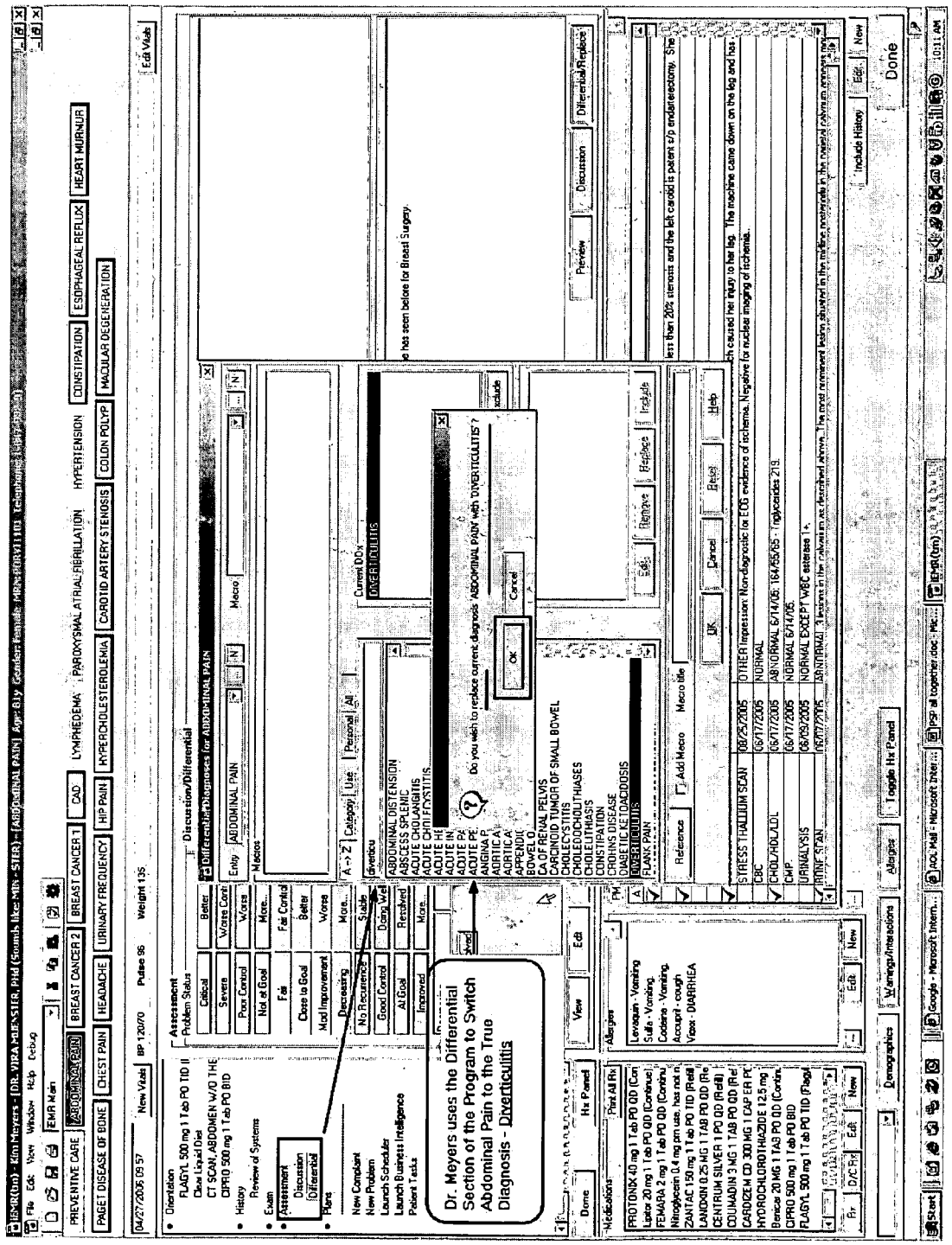

FIG. 50. Dr. Meyers used the differential section of the program to switch abdominal pain to the true diagnosis—diverticulitis.

Figure 51:
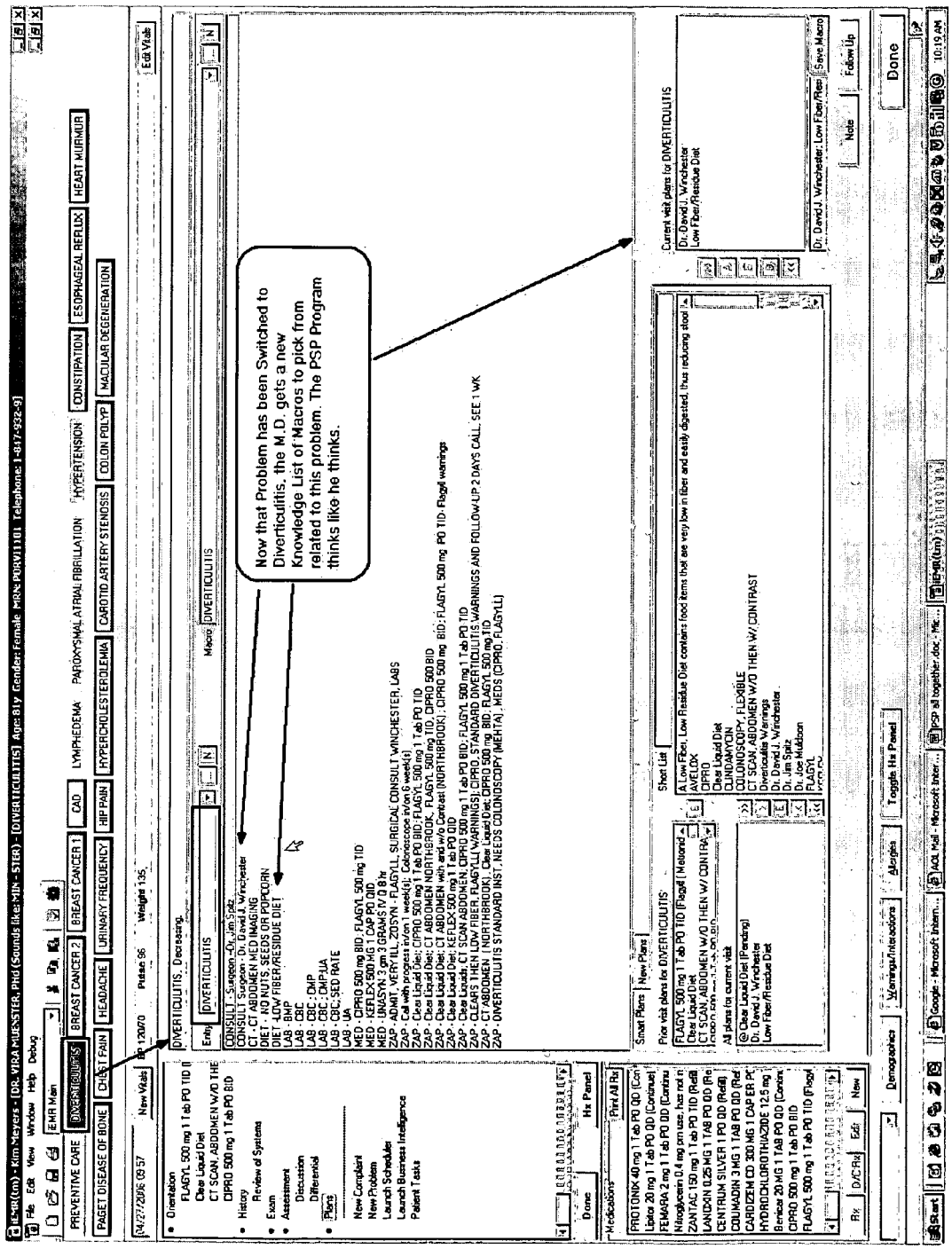

FIG. 51. Now that problem has been switched to diverticulitis, the M.D. Gets a new knowledge list of macros to pick from related to this problem. The PSP program thinks like he thinks.

Figure 52:
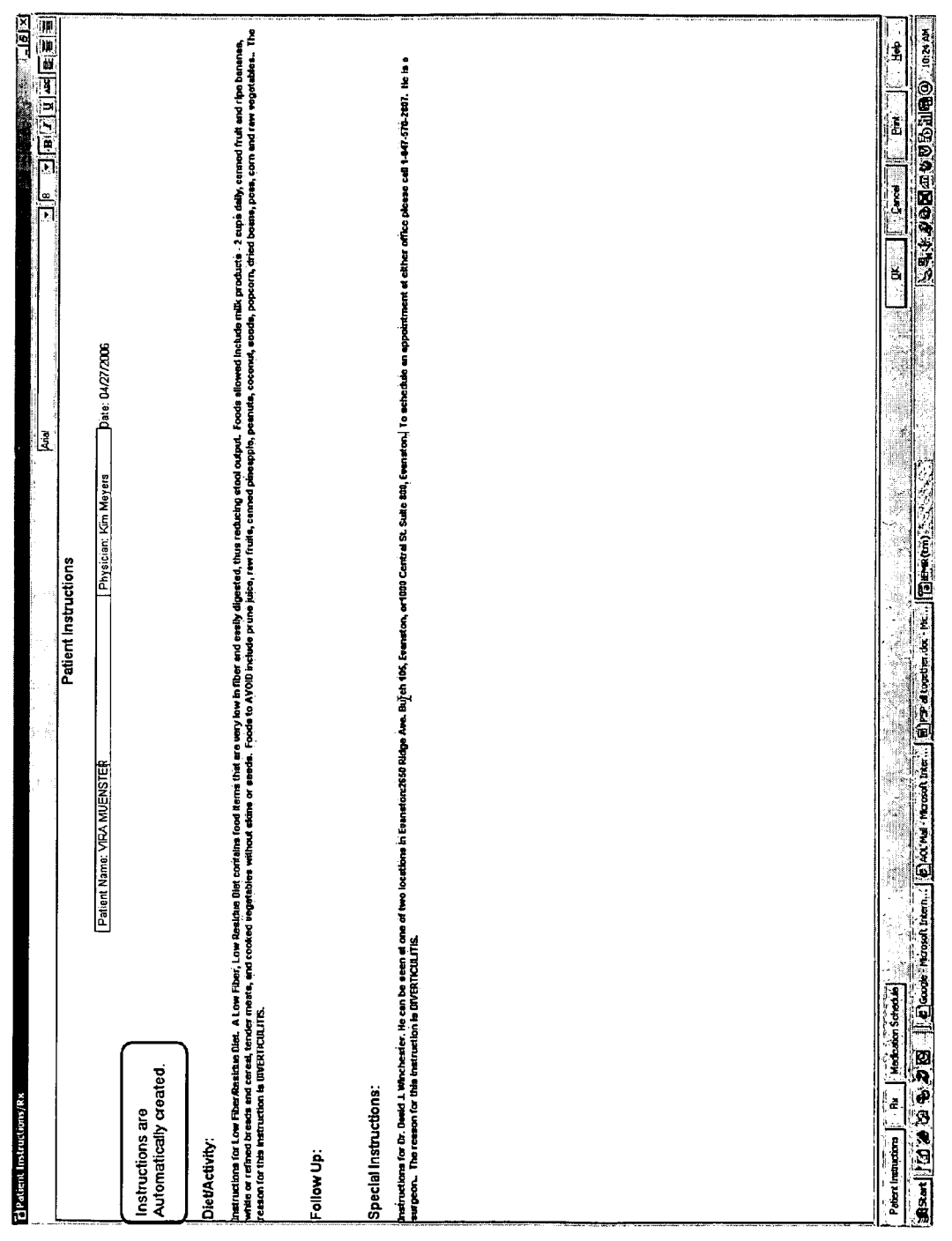

FIG. 52. Instructions are automatically created.

Figure 53:
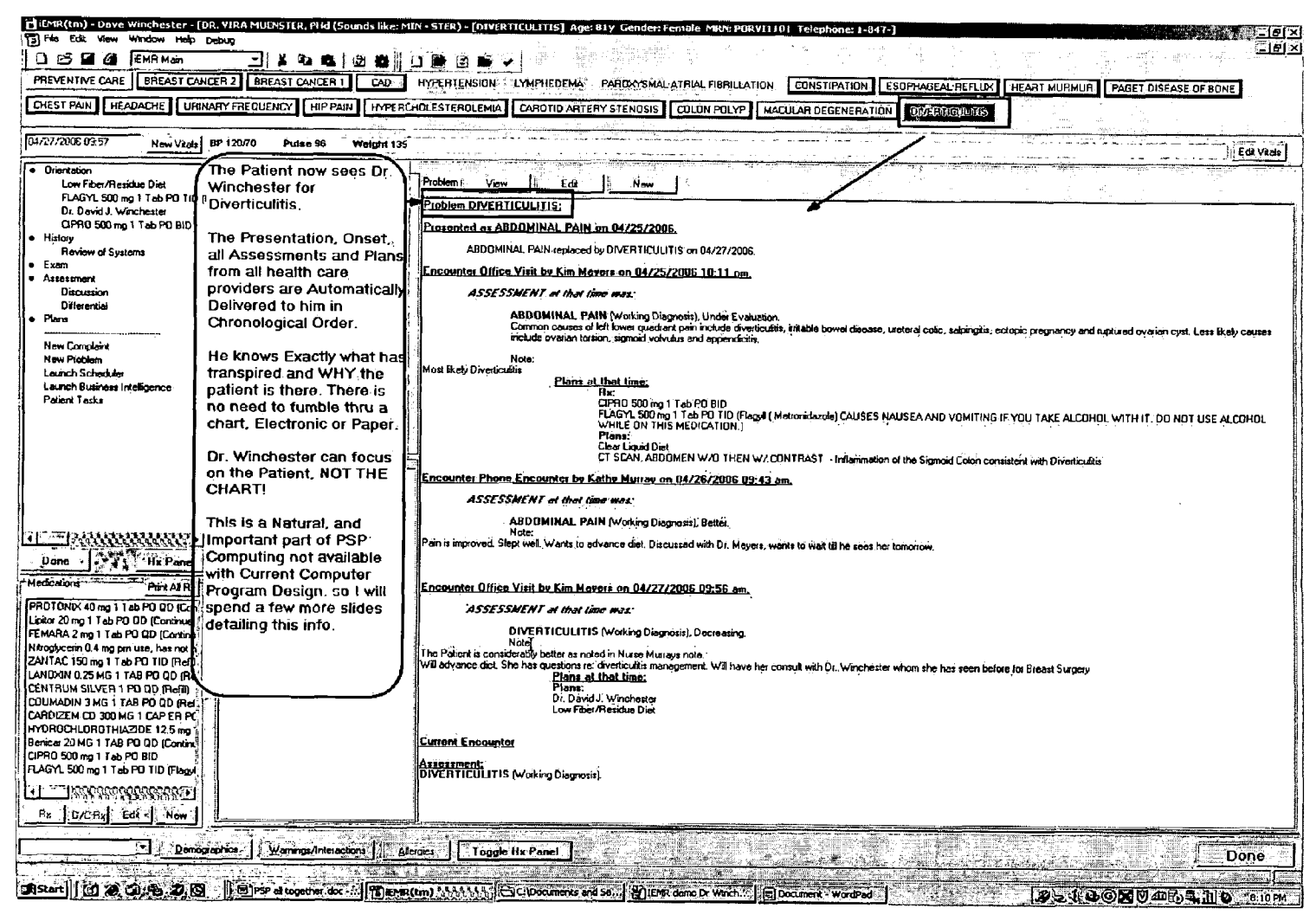

FIG. 53. The patient now sees dr. Winchester for "diverticulitis". The presentation, onset, all assessments and plans from all health care providers are automatically delivered to him in chronological order. He knows exactly what has transpired and why the patient is there. There is no need to fumble thru a chart. Electronic or paper. Dr. Winchester can focus on the patient, not the chart! This is a natural, and important part of PSP computing not available with current computer program design, so I will spend a few more slides detailing this information.

Figure 54:
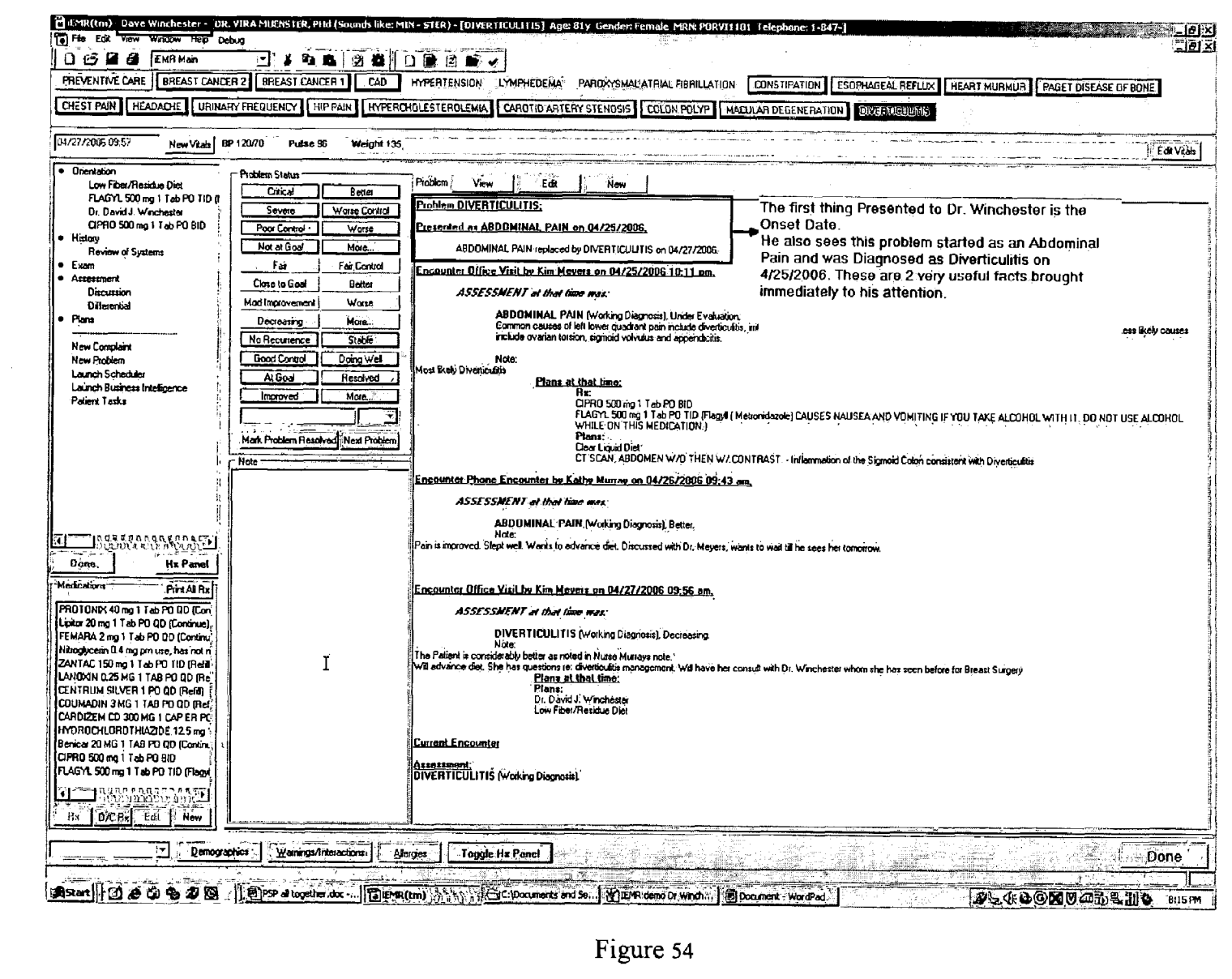

FIG. 54. The first thing presented to Dr. Winchester is the onset date. He also sees this problem started as an abdominal pain and was diagnosed as diverticulitis on Apr. 25, 2006. These are two very useful facts brought immediately to his attention.

Figure 55:
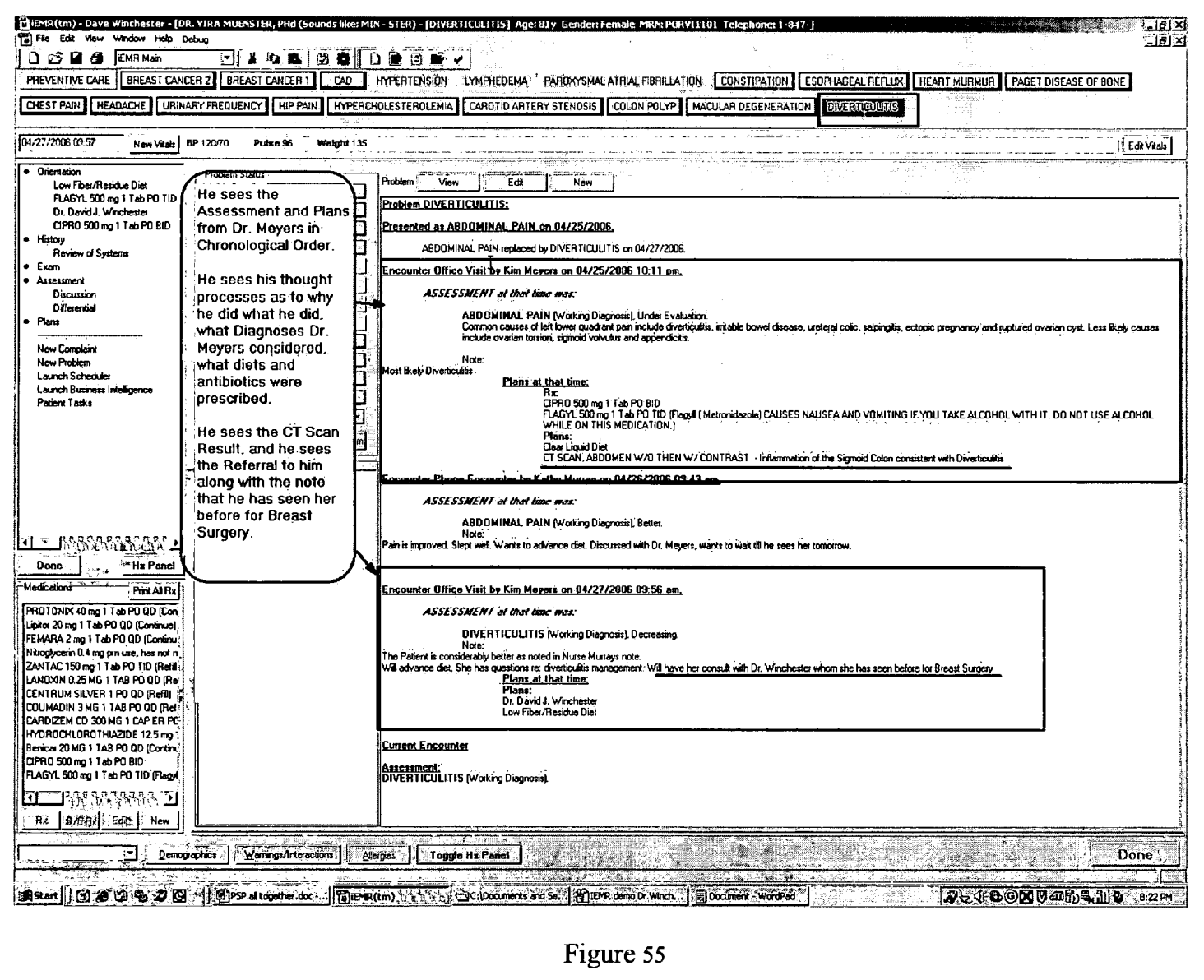

FIG. 55. He sees the assessment and plans from Dr. Meyers in chronological order. He sees his thought processes as to why he did what he did, what diagnosis Dr. Meyers considered, what diets and antibiotics were prescribed. He sees the ct scan result, and he sees the referral to him along with the note that he has seen her before for breast surgery.

Figure 56:
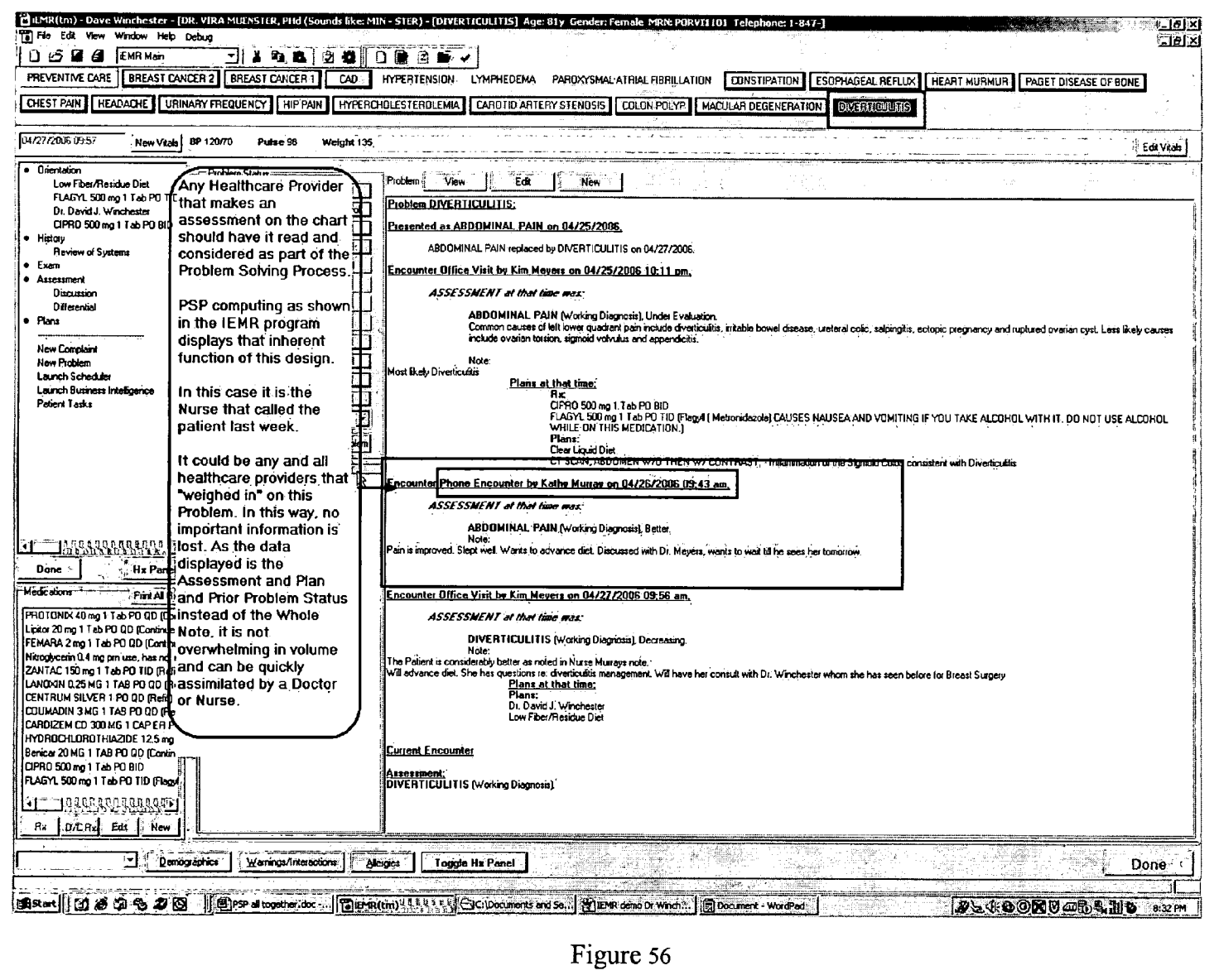

FIG. 56. Any healthcare provider that makes an assessment on the chart should have it read and considered as part of the problem solving process. PSP computing as shown in the iEMR program displays that inherent function of this design. In this case, it is the nurse that called the patient last week. It can also be any and all healthcare providers that "weighed in" on this problem. In this way, no important information is lost, as the data displayed is the assessment and plan and prior problem status instead of the whole note, it is not overwhelming in volume and can be quickly assimilated by a doctor or nurse.

Figure 57:
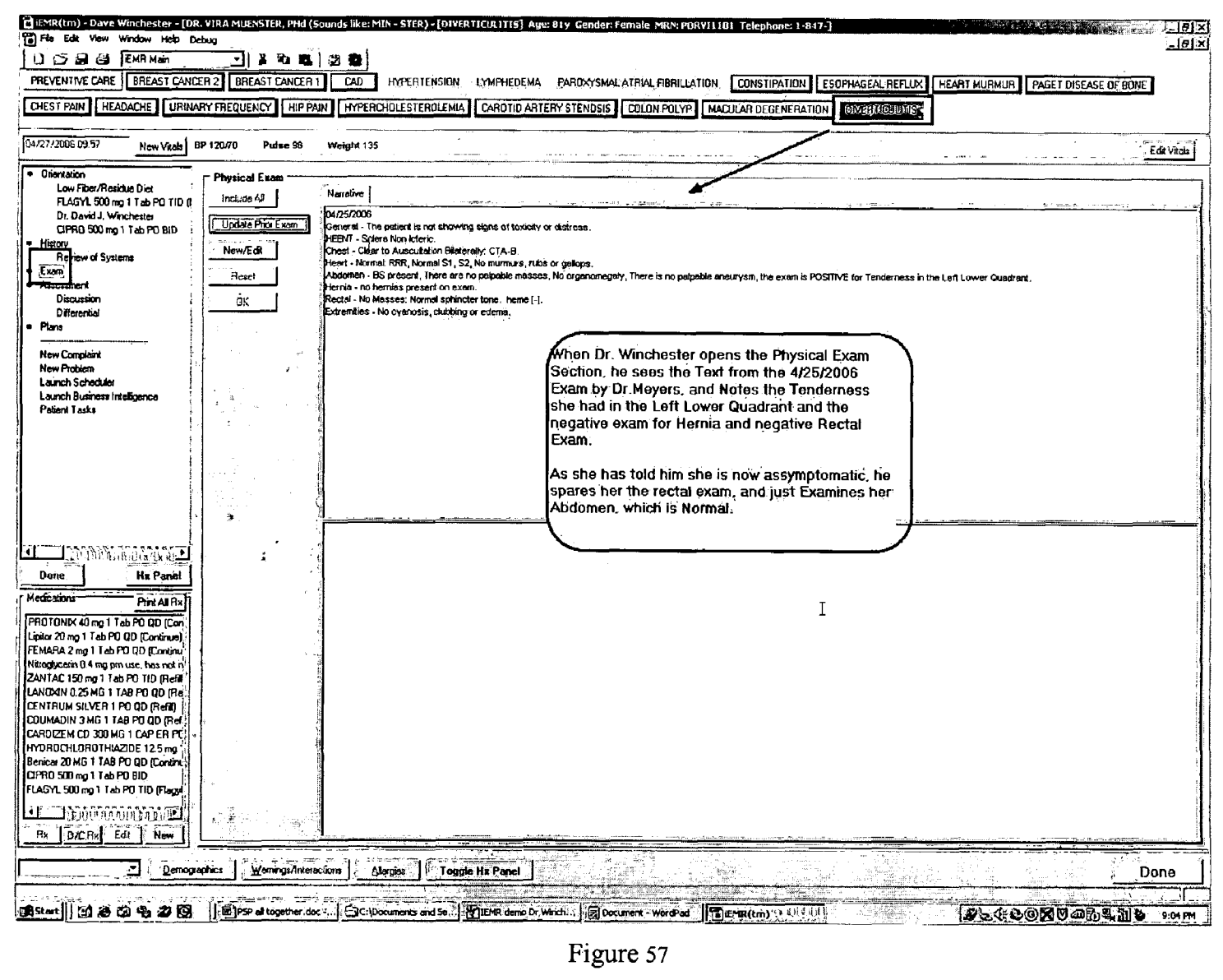

FIG. 57. When Dr. Winchester opens the physical exam section, he sees the text from the Apr. 25, 2006 exam by Dr. Meyers, and notes the tenderness she had in the left lower quadrant and the negative exam for hernia and negative rectal exam. As she has told him she is now asymptomatic, he spares her the rectal exam, and just examines her abdomen, which is normal.

Figure 58:
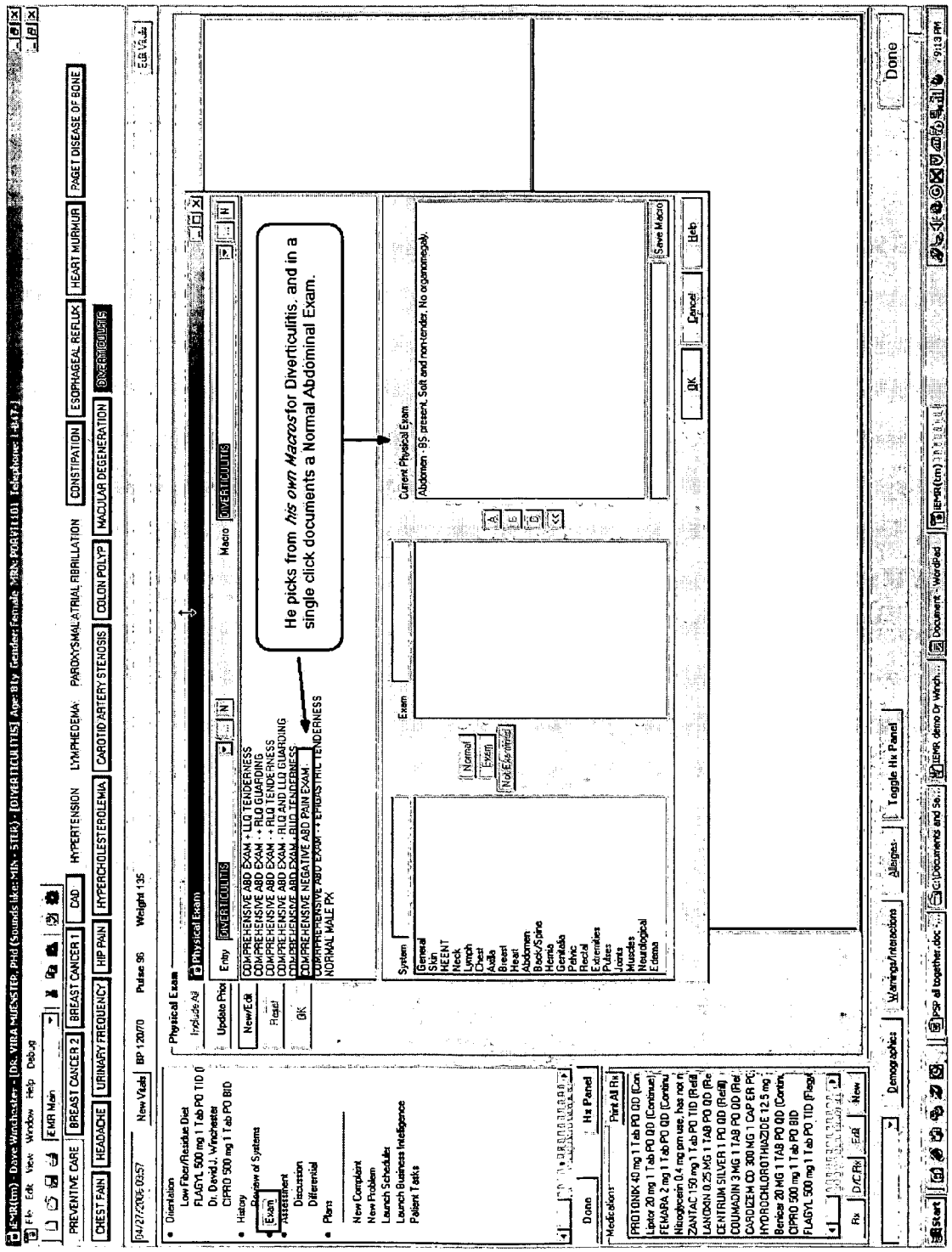

FIG. 58. He picks from his own macros for diverticulitis, and in a single click documents a normal abdominal exam.

Figure 59:
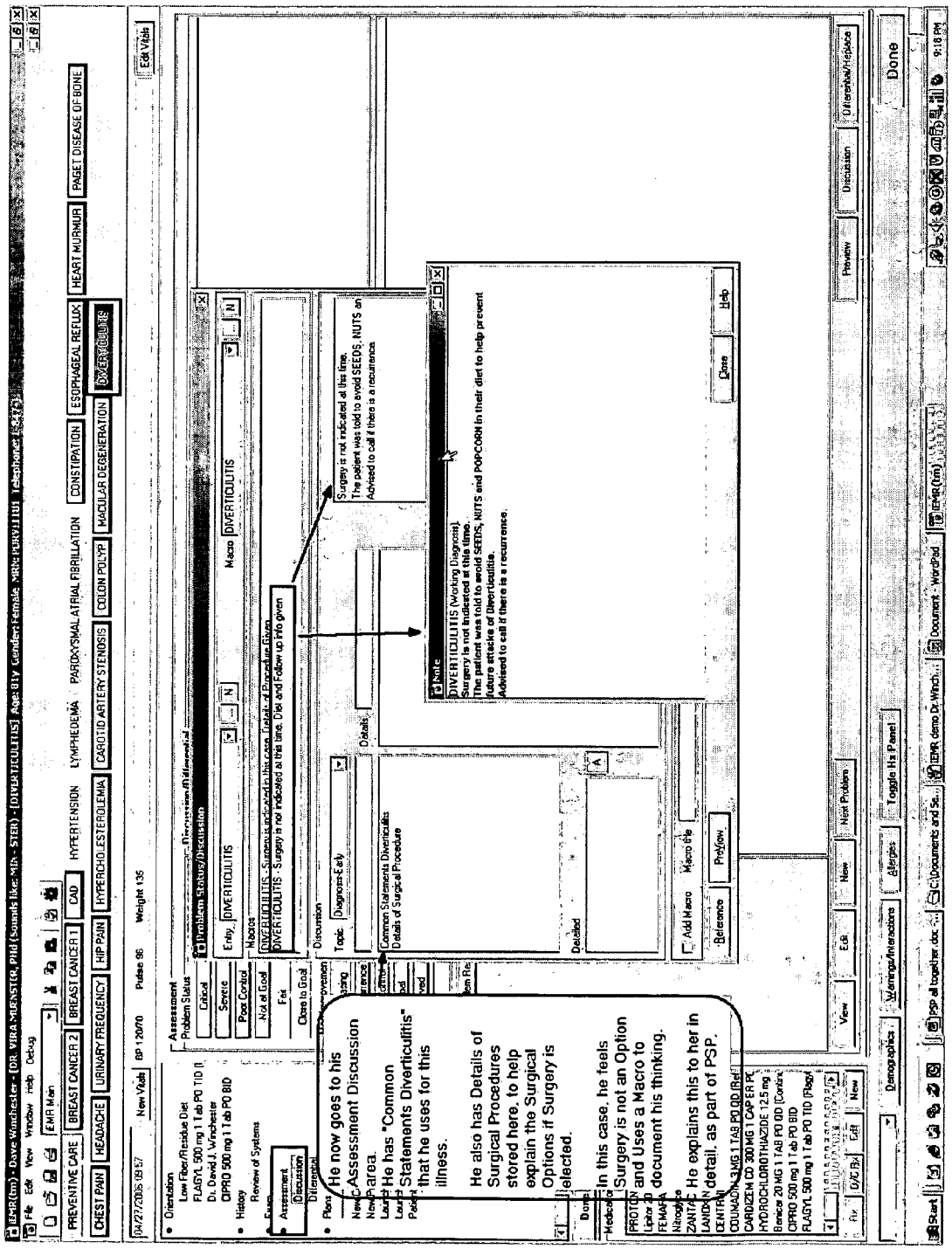

FIG. 59. He now goes to his assessment discussion area. He has "common statements diverticulitis" that he uses for this illness. He also has details of surgical procedures stored here to help explain the surgical options if surgery is elected. In this case, he feels surgery is not an option and uses a macro to document his thinking. He explains this to her in detail, as part of PSP.

Figure 60:
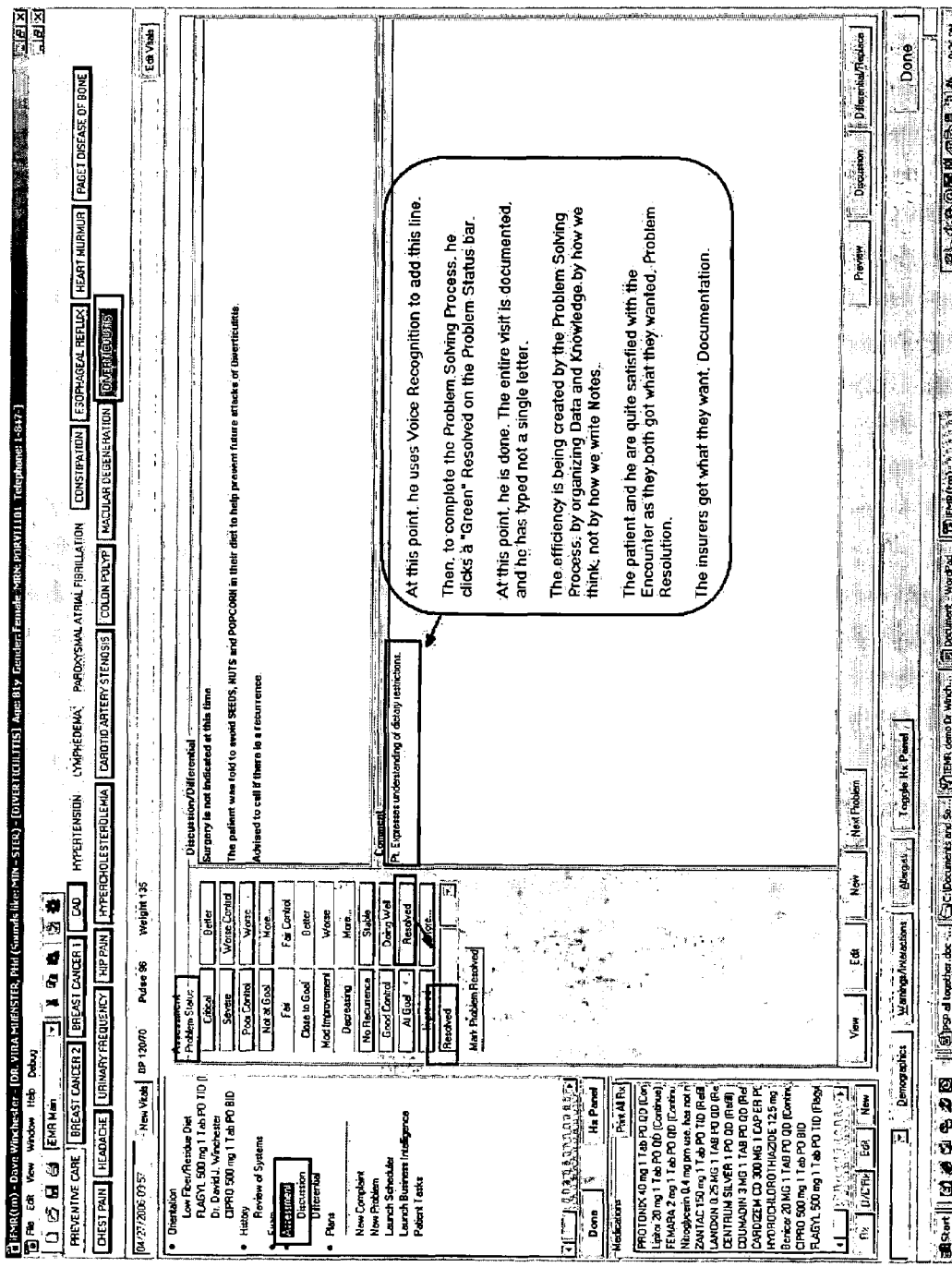

FIG. 60. At this point, he uses voice recognition to add this line. Then, to complete the problem solving process, he clicks a "green" resolved on the problem status bar. At this point, he is done. The entire visit is documented, and he has typed not a single letter. The efficiency is being created by the problem solving process, by organizing data and knowledge by how we think, not by how we write notes. The patient and he are quite satisfied with the encounter as they both got whey they wanted. Problem resolution. The insurers get what they want, documentation.

Figure 61:
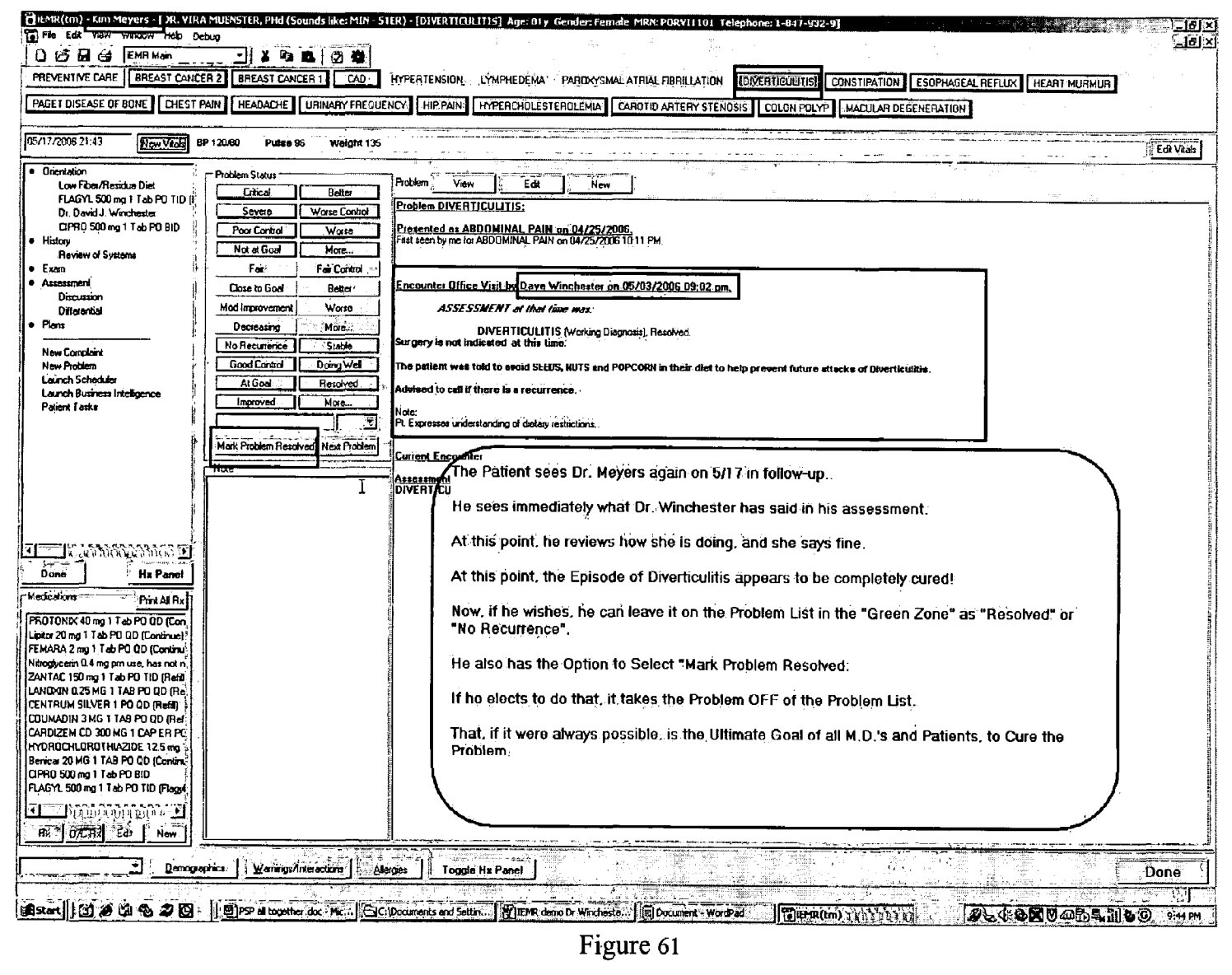

FIG. 61. The patient sees Dr. Meyers again on May 17, 2006 in follow-up. He sees immediately what Dr. Winchester has said in his assessment. At this point, he reviews how she is doing and she says, "fine." At this point, the episode of diverticulitis appears to be completely cured! Now, if he wishes, he can leave it on the problem list in the "green zone" as "resolved" or "no recurrence". He also has the option to select "mark problem resolved". If he elects to do that, it takes the problem off of the problem list. That, if it were always possible, is the ultimate goal of all M.D.'s and patients, to cure the problem.

Figure 62:
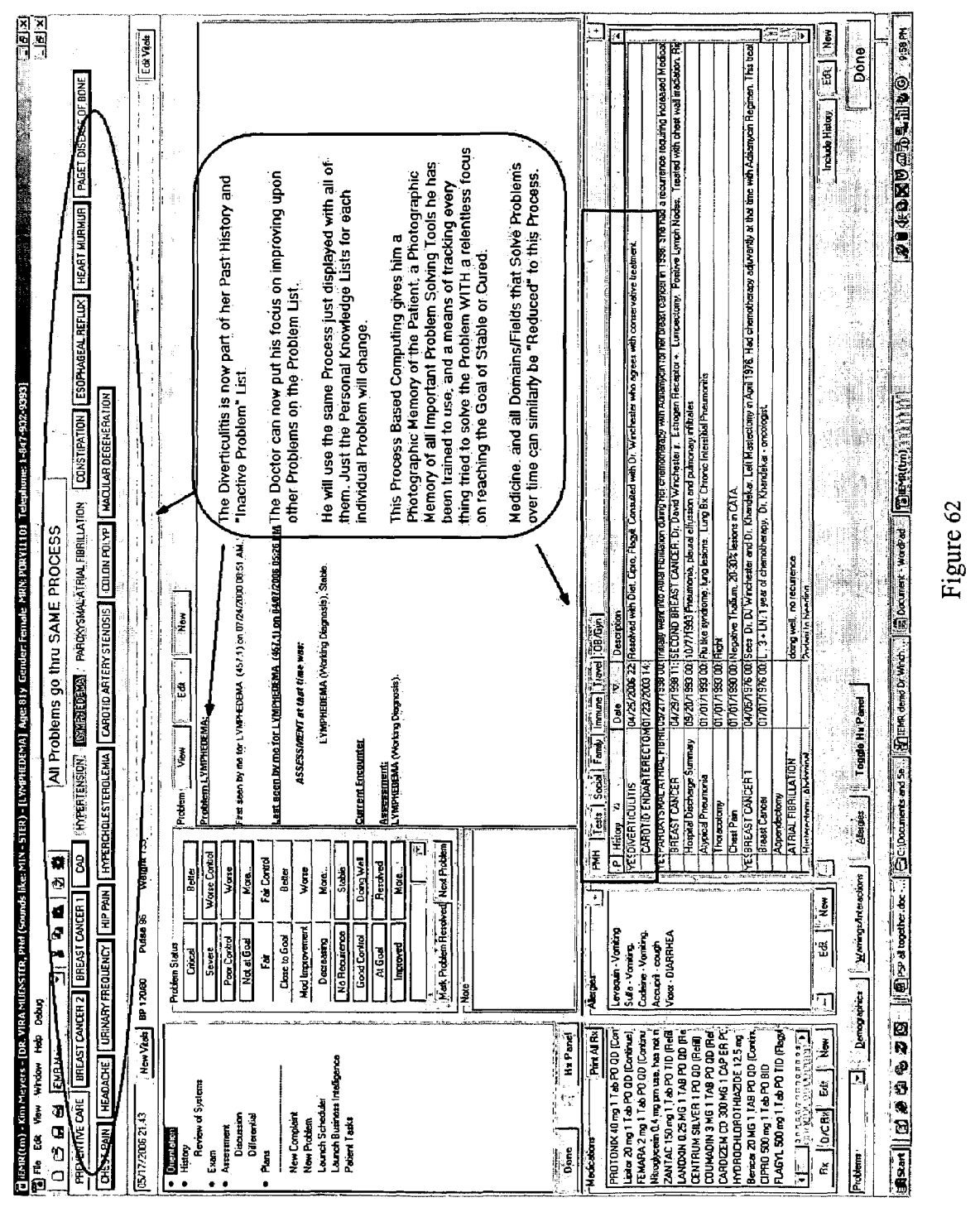

FIG. 62. The diverticulitis is now part of her past history and "inactive problem" list. The doctor can now put his focus on improving upon other problems on the problem list. He will use the same process just displayed with all of them. Just the personal knowledge lists for each individual problem will change. This process based computing gives him a photographic memory of the patient, a photographic memory of all important problem solving tools he has been trained to use, and a means of tracking everything tried to solve the problem with a relentless focus on reaching the goal of stable or cured. Medicine, and all domains/fields that solve problems over time can similarly be "reduced" to this process.

Figure 63:
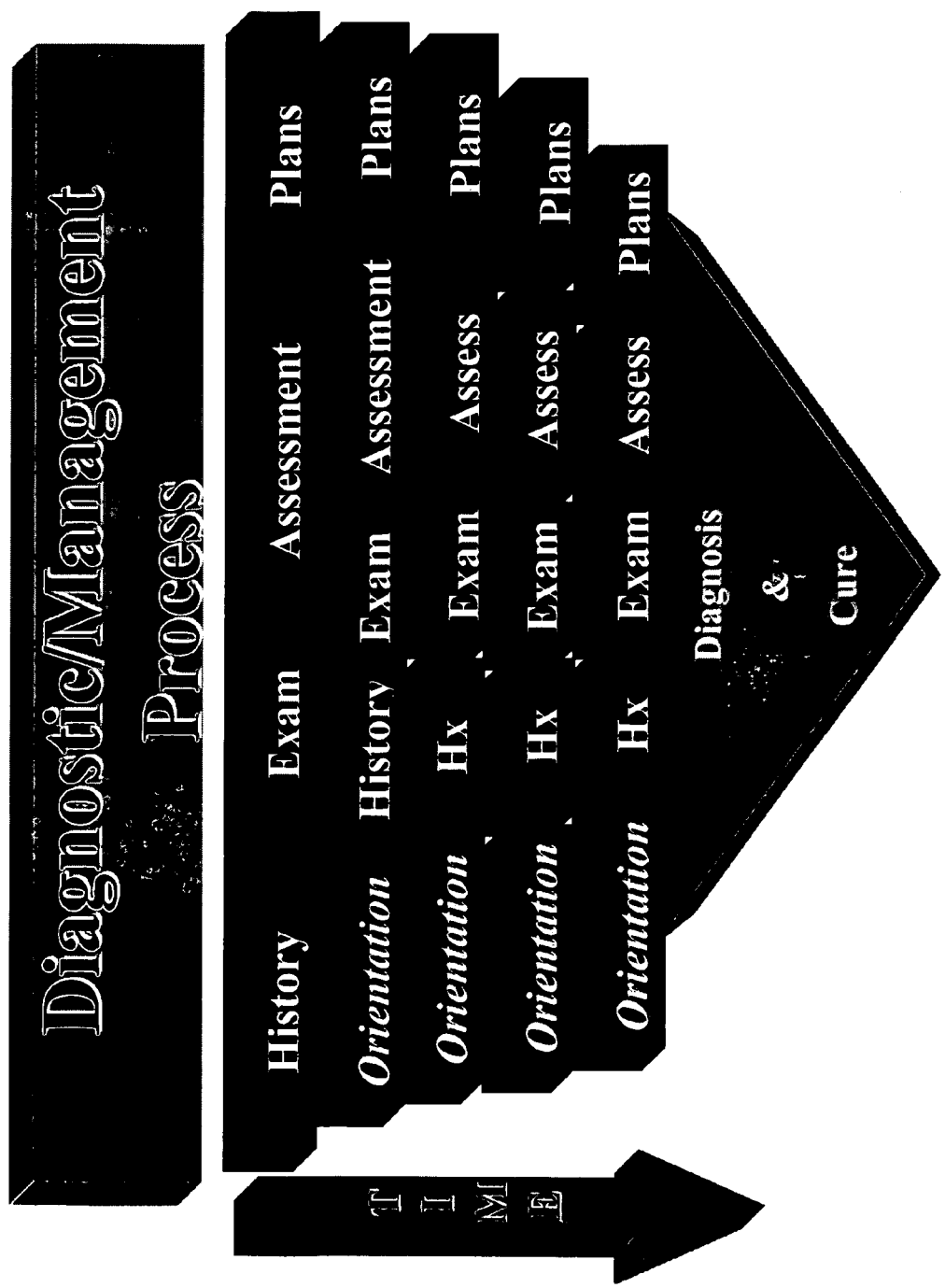

FIG. 63. Diagnostic/management process.

Figure 64:
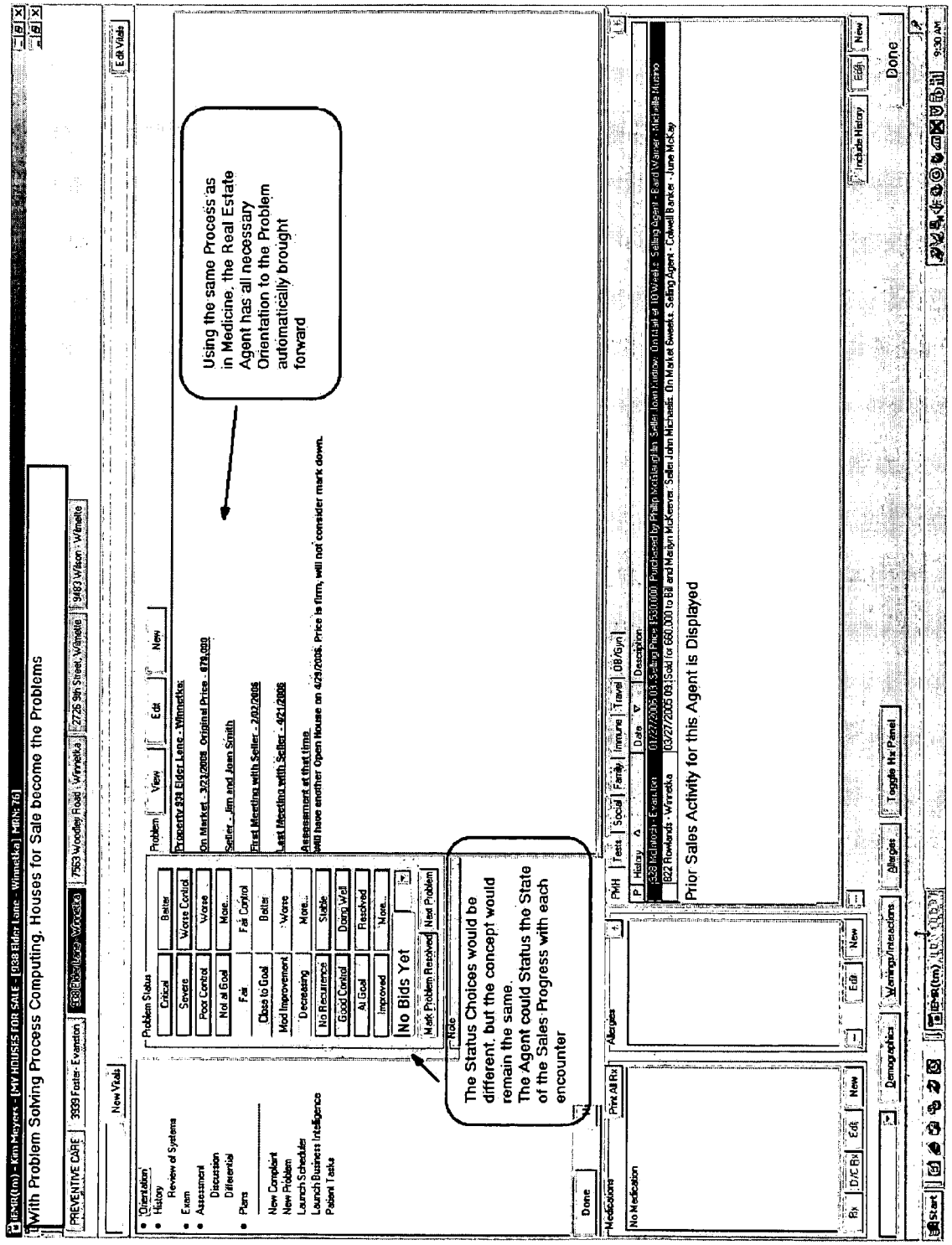

FIG. 64. Using the same process as in medicine, the real estate agent has all necessary orientation to the problem automatically brought forward. The status choices would be different, but the concept would remain the same. The agent could status the state of the sales progress with each encounter.

Figure 65:
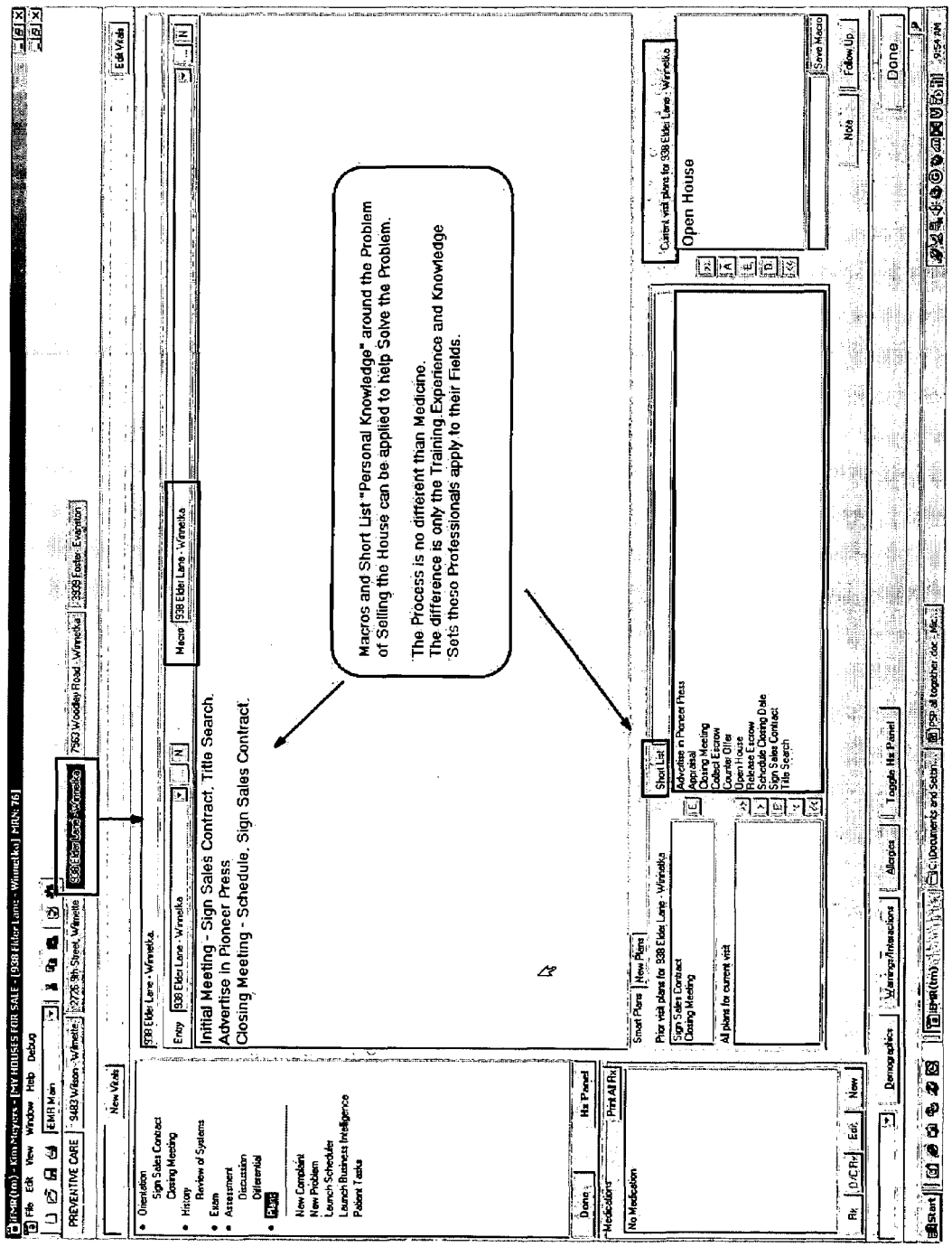

FIG. 65. Macros and short list "personal knowledge" around the problem of selling the house can be applied to help solve the problem. The process is not different than medicine. The difference is only the training experience and knowledge sets these professional apply to their fields.

Figure 66:
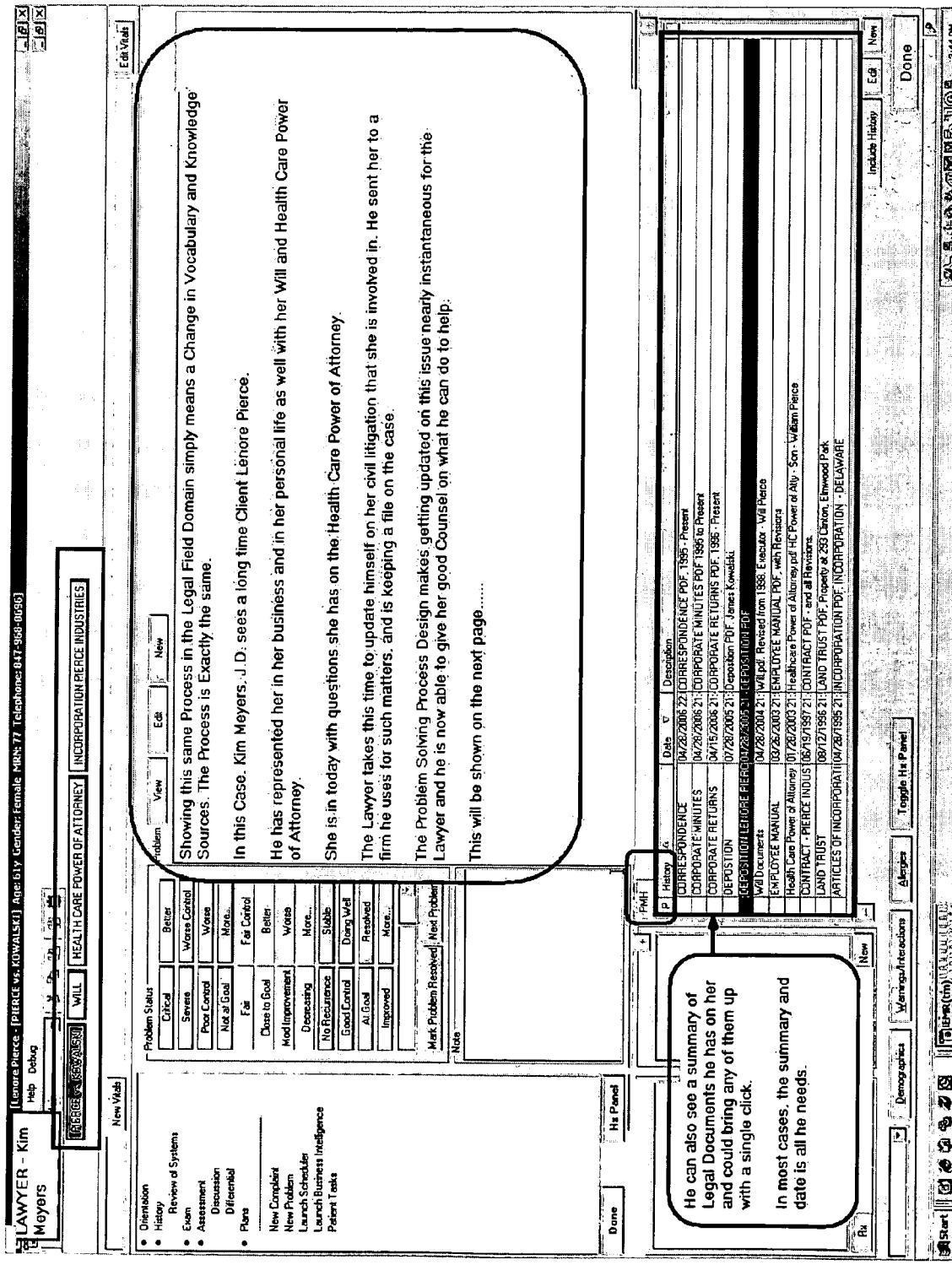

FIG. 66. Showing this same process in the legal field domain simply means a change in vocabulary and knowledge sources. The process is exactly the same. In this case, Kim Meyers, J. D. Sees a long time client, Lenore Pierce. He has represented her in her business and in her personal life as well with her will and health care power of attorney. She is in today with questions she has on the health care power of attorney. The lawyer takes this time to update himself on her civil litigation that she is involved in. He sent her to a firm he uses for such matters, and is keeping a file on the case. The problem solving process design makes getting updated on this issue nearly instantaneous for the lawyer and he is now able to give her good counsel on what he can do to help. This will be shown on the next page.

Figure 67:
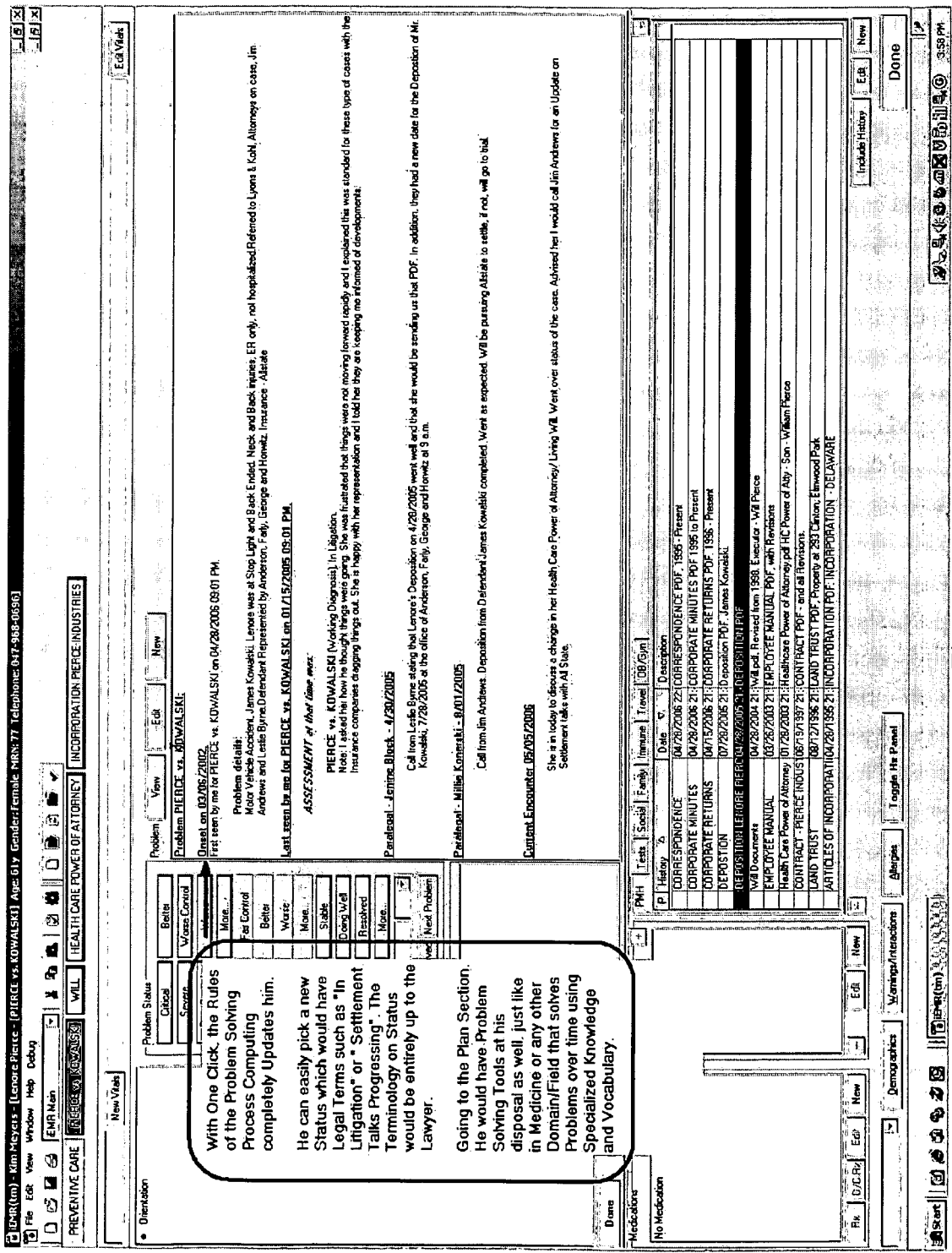

FIG. 67. With one click, the rules of the problem solving process computing completely updates him. He can easily pick a new status which would have legal terms such as "in litigation" or "settlement talks progressing". The terminology on status would be entirely up to the lawyer. Going to the plan section, he would have problem solving tools at his disposal, just like in medicine or any other domain/field that solves problems over time using specialized knowledge and vocabulary.

Figure 68:
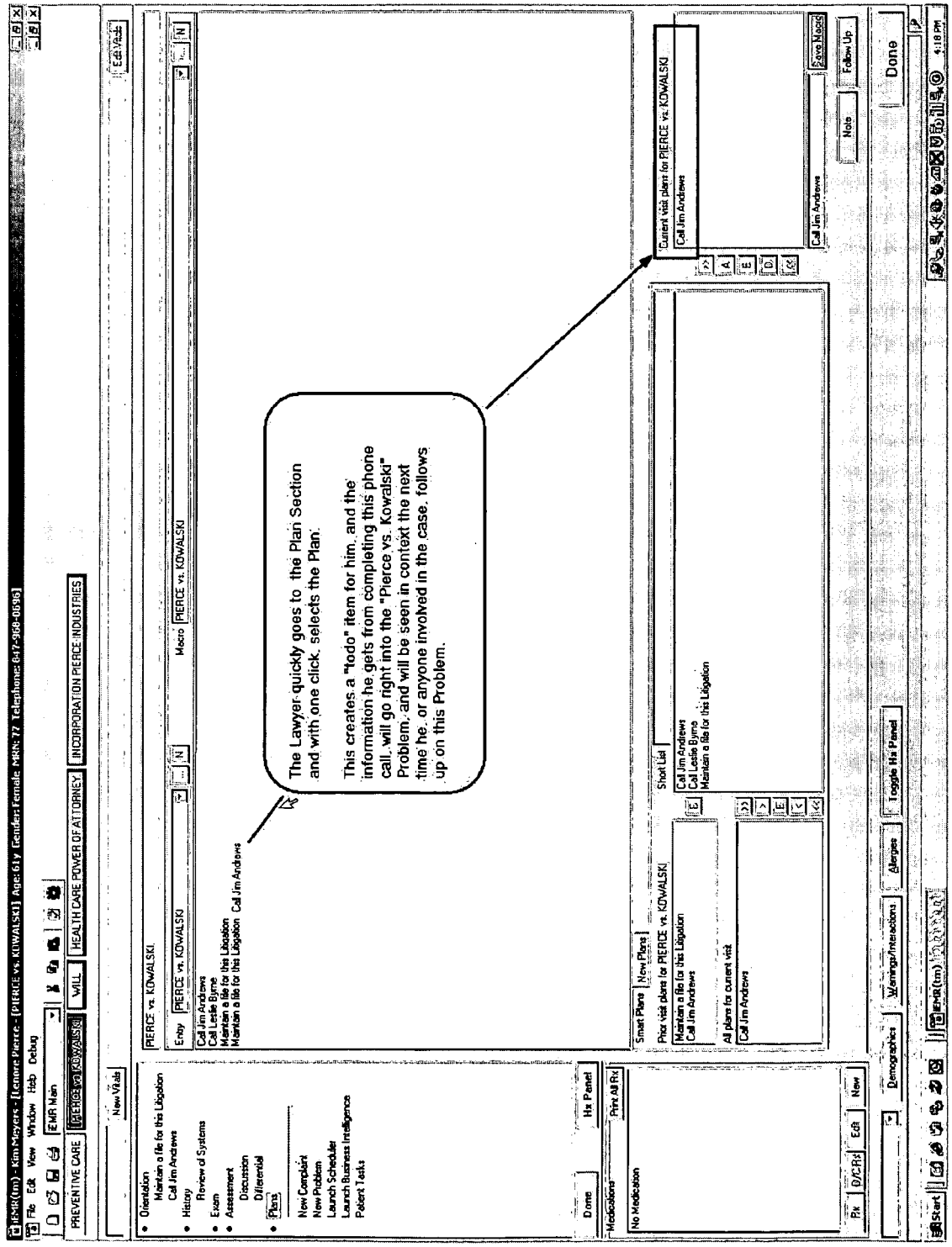

FIG. 68. The lawyer quickly goes to the plan section and with one click, selects the plan. This creates a "to do" item for him, and the information he gets from completing this phone call will go right into the "Pierce vs. Kowalski" problem, and will be seen in context the next time he, or anyone involved in the case follows up on this problem.

Figure 69:
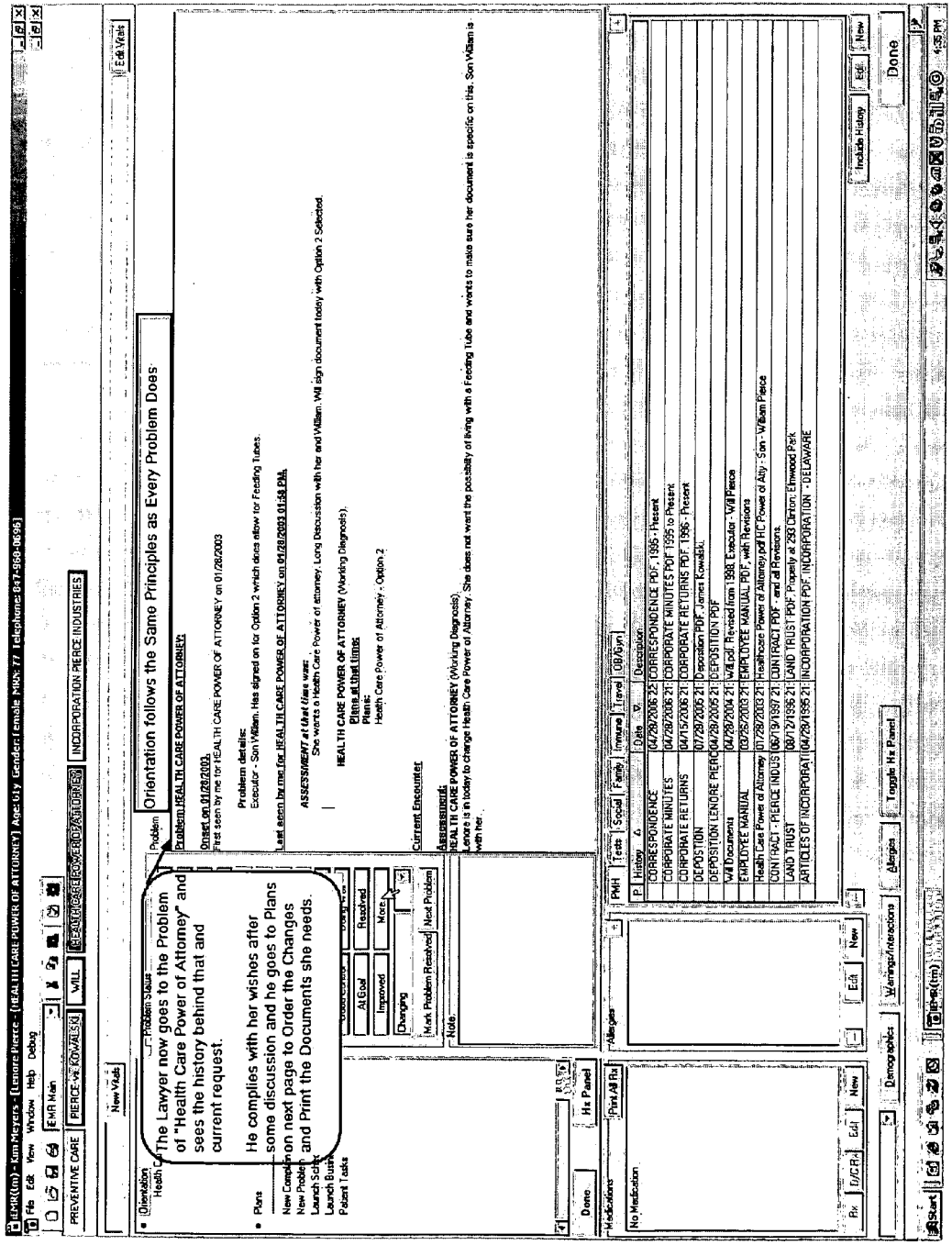

FIG. 69. The lawyer now goes to the problem of "health care power of attorney" and sees the history behind that and current request. He complies with her wishes after some discussion and he goes to plans on next page to order the changes and print the documents she needs.

Figure 70:
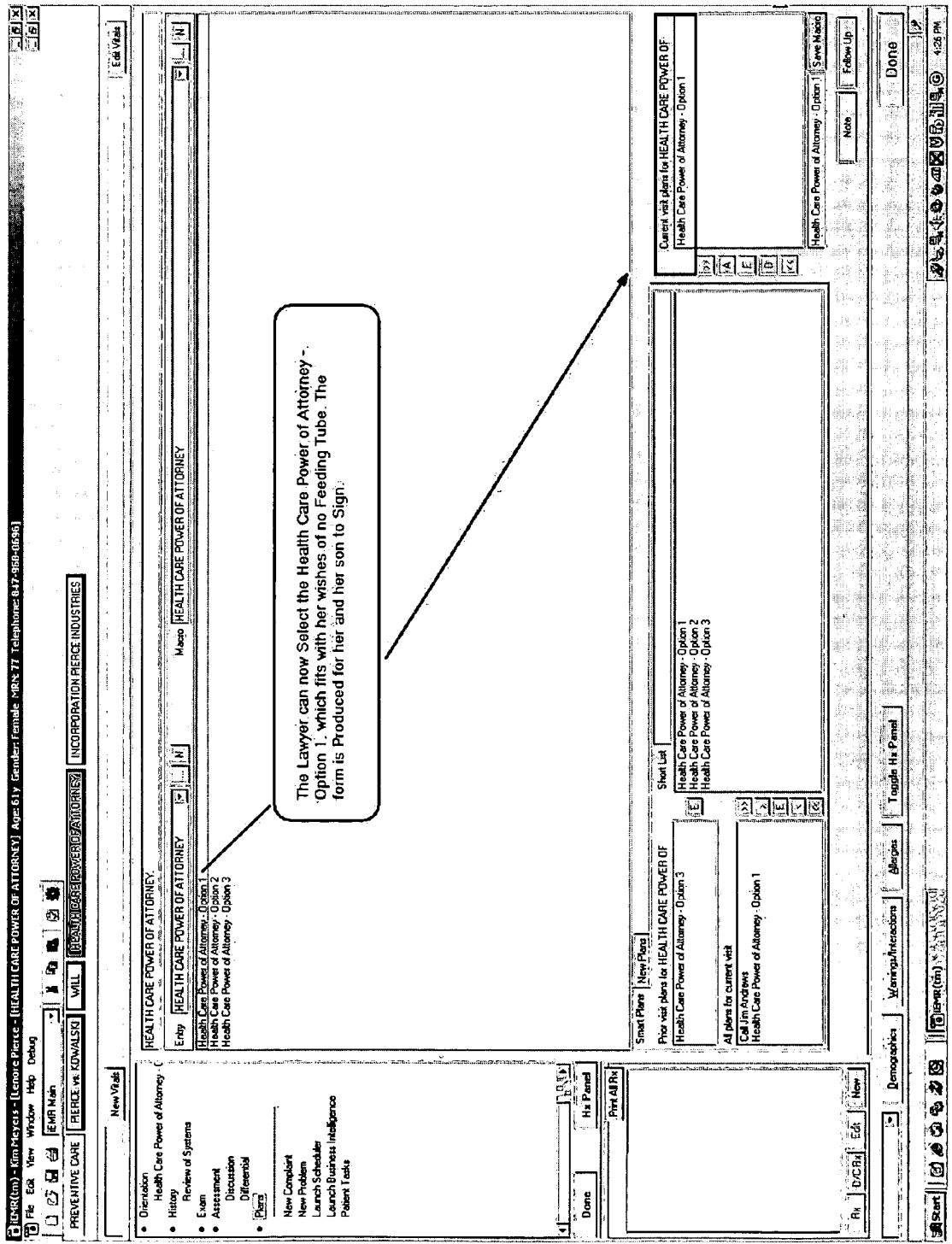

FIG. 70. The lawyer can now select the health care power of attorney option 1, which fits with her wishes of no feeding tube. The form is produced for her and her son to sign.

FIG. 71. The phone call to Jim Andrews regarding her litigation will remain on his "To Do" list until he completes this "Plan" that is now part of the Problem Solving Process. Any note made from this Phone Encounter will be nested under the "Pierce vs. Kowalski" Problem.

The patent applicant again claims that this process is broadly applicable to any problem solving domain/field. Computer programs designed around the problem solving process. PSP Computing represents a transformational technology. This will advance the human computer interface into a truly "natural human interface" and lead to efficiencies that are not reachable with current form based and Root-Tree-Branch-Leaf-Vein-Node designs.

iEMR

The problem-solving process and related EMR described in the above discussion are particularly adapted to run on an EMR system known as iEMR described in U.S. patent application Ser. No. 11/065,600 filed on Feb. 24, 2005, titled "Method for Advanced Data Management", and United States patent that application Ser. No. 09/997,723 filed on Nov. 30, 2001, titled "Advanced Data Manager" (of which the former application is a continuation-in-part), and in the paper *Expert Knowledge Base Designed Using ER-Modeling Technique*, Naeymi-Rad et al. (1986). The iEMR was developed by Intelligent Medical Objects, Inc., 60 Revere Drive, Northbrook, Ill. 60062

This application incorporates by reference U.S. application Ser. No. 11/065,600 filed on Feb. 24, 2005, titled "Method for Advanced Data Management", and U.S. application Ser. No. 09/997,723 filed on Nov. 30, 2001, titled "Advanced Data Manager" (of which the former application is a continuation-in-part), as if fully reproduced herein.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

What is claimed is:

1. A computer implemented problem solving system utilizing an information storage infrastructure and a flexible development environment for data storage, comprising:
   a stored, user modifiable program including a problem solving rule set relevant to a problem to be solved,
   a stored, user modifiable set of vocabularies related to a problem to be solved,
   at least one stored, user modifiable knowledge set relevant to a problem to be solved, and
   stored, user modifiable individual user preferences relevant to a problem to be solved, wherein said knowledge set is applied to diagnose and manage said problem, said set of vocabularies are used to name tools for said problem diagnosis and management, and said individual user preferences are used to organize said problem diagnosis and management tools; wherein said system allows a user to evaluate said problem to be solved and provides options to said user to develop a plan to manage said problem to be solved, and further wherein said rule set includes iteration of evaluations and plans, and said system orients said user to a status of said problem to be solved at each iteration to allow said user to manage said problem to be solved.

2. A computer implemented problem solving system according to claim 1, wherein said set of vocabularies, said at least one knowledge set and said individual user preferences comprise a relational database.

3. A computer implemented problem solving system according to claim 2, wherein said relational database includes a plurality of tables having a table driven infrastructure.

4. A computer implemented problem solving system according to claim 1, and further including a display screen, said computer generating a screen display including user viewable and modifiable display portions corresponding to said set of vocabularies, said at least one knowledge set and said individual user preferences.

5. A computer implemented problem solving system according to claim 1, and further including user accessible means in said screen display for retrieving net based information for adding to said set of vocabularies, said at least one knowledge set and said individual user preferences.

6. A computer implemented problem solving system according to claim 1, wherein said set of vocabularies, said at least one knowledge set and said individual user preferences may be user modified by adding, editing, and deleting elements.

7. A system according to claim 6, further comprising a program capable of tracking said adding, editing, and deleting with user, date, and data value information.

8. A system according to claim 6, further comprising a program for processing user requests to modify using rules governing relationships among the elements of said set of vocabularies, said at least one knowledge set and said individual user preferences.

9. A computer implemented problem solving method utilizing an information storage infrastructure and a flexible development environment for data storage, comprising:
generating screen displays on a display screen;
entering a problem identified by an initial assessment to said computer at a designated place in one of said screen displays;
selecting from at least one of said screen displays at least one item from at least one of:
a stored, user modifiable set of vocabularies related to a problem to be solved,
at least one stored, user modifiable knowledge set relevant to a problem to be solved, and
stored, user modifiable individual user preferences relevant to a problem to be solved, and entering said at least one item to said computer at a designated place in one of said screen displays,
applying said knowledge set to diagnose and manage said problem;
naming tools for said problem diagnosis and management using said set of vocabularies; and
organizing said problem diagnosis and management tools using said individual user preferences;
wherein said selecting step comprises evaluating said problem to be solved and said generating step comprises providing options to said user to develop a plan to manage said problem to be solved,
said method further comprising
orienting said user to a status of said problem to be solved by displaying iterations of evaluations and plans related to said problem to be solved.

10. A computer implemented problem solving method according to claim 9, and further including retrieving net based information for adding to said set of vocabularies, said at least one knowledge set and said individual user preferences.

11. A computer implemented problem solving method according to claim 9, and further including modifying at least one of said set of vocabularies, said at least one knowledge set and said individual user preferences.

12. A computer implemented problem solving method according to claim 11, wherein said step of modifying comprises at least one of the steps of adding, editing, and deleting an element.

13. A computer implemented problem solving method according to claim 9, wherein said step of selecting comprises at least one of the steps of retrieving, viewing, adding, and deleting.

14. A system for creating an electronic medical record using a computer implemented problem solving system having an information storage infrastructure and a flexible development environment for data storage, comprising:
a stored, user modifiable program including a problem solving rule set relevant to medical diagnosis and treatment,
a stored, user modifiable set of vocabularies related to medical diagnosis and treatment,
at least one stored, user modifiable knowledge set relevant to medical diagnosis and treatment, and
stored, user modifiable individual user preferences relevant to medical diagnosis and treatment,
wherein said knowledge set is applied to diagnose and treat a problem, said knowledge set nested by both problem and stage of diagnosis or treatment;
wherein said set of vocabularies are used to name tools for said diagnosis and treatment;
wherein said individual user preferences are used to organize said diagnosis and treatment tools;
wherein said system allows a user to determine a medical diagnosis and provides options to said user to develop a treatment, wherein said system updates said electronic medical record with information concerning said medical diagnosis and said treatment;
and further wherein said rule set includes iteration of diagnoses and treatments, and said system orients said user to a status of said medical diagnosis and treatment at each iteration to allow said user to manage said treatment.

15. A system according to claim 14, and further including:
means for generating screen displays on a display screen;
means for entering a problem identified by an initial assessment to said computer at a designated place in one of said screen displays;
means for selecting from at least one of said screen displays at least one item from at least one of said stored, user modifiable set of vocabularies related to medical diagnosis and treatment, said at least one stored, user modifiable knowledge set relevant to medical diagnosis and treatment, and said stored, user modifiable individual user preferences relevant to medical diagnosis and treatment, and
means for entering said at least one item to said computer at a designated place in one of said screen displays.

16. A system according to claim 14, wherein said set of vocabularies, said at least one knowledge set and said individual user preferences comprise a relational database.

17. A solving system according to claim 16, wherein said relational database includes a plurality of tables having a table driven infrastructure.

18. A system according to claim 14, and further including a display screen, said computer generating a screen display including user viewable and modifiable display portions corresponding to said set of vocabularies, said at least one knowledge set and said individual user preferences.

19. A system according to claim 14, and further including user accessible means in said screen display for retrieving net based information for adding to said set of vocabularies, said at least one knowledge set and said individual user preferences.

20. A system according to claim 14, wherein said set of vocabularies, said at least one knowledge set and said individual user preferences may be user modified by adding, editing, and deleting elements.

21. A system according to claim 20, further comprising a program capable of tracking said adding, editing, and deleting with user, date, and data value information.

22. A system according to claim 20, further comprising a program for processing user requests to modify using rules governing relationships among the elements of said set of vocabularies, said at least one knowledge set and said individual user preferences.

23. A system according to claim 14, further comprising a program for processing user requests so that with one click a diagnostic test can be ordered and clear instructions are written on how to schedule it and get to the testing facility; in addition, medical necessity is cleared, and any needed prescription is written.

24. A system according to claim 14, further comprising a program for processing user requests so that upon entering an order, all needed forms and documentation are automatically generated.

25. A system according to claim 14, further comprising a program for creating a screen display including a problem bar, comprising a plurality of individual tabs near the top of the page, and arranged in order of relative importance.

26. A system according to claim 25, wherein said tabs are color coded to delineate the importance/severity of the problems.

* * * * *